United States Patent
Rombouts et al.

(10) Patent No.: US 8,778,919 B2
(45) Date of Patent: Jul. 15, 2014

(54) CYCLIC ANILINO—PYRIDINOTRIAZINES

(75) Inventors: Frederik Jan Rita Rombouts, Antwerp (BE); Christopher John Love, Deurne (BE); Kristof Van Emelen, Sint-Niklaas (BE); Sven Franciscus Anna Van Brandt, Nijlen (BE); Tongfei Wu, Turnhout (BE)

(73) Assignee: Janssen Pharmaceutica NV, Beerse (BE)

( * ) Notice: Subject to any disclaimer, the term of this patent is extended or adjusted under 35 U.S.C. 154(b) by 1367 days.

(21) Appl. No.: 11/993,237

(22) PCT Filed: Jun. 26, 2006

(86) PCT No.: PCT/EP2006/063555
§ 371 (c)(1),
(2), (4) Date: Dec. 20, 2007

(87) PCT Pub. No.: WO2007/003525
PCT Pub. Date: Jan. 11, 2007

(65) Prior Publication Data
US 2010/0222574 A1 Sep. 2, 2010

(30) Foreign Application Priority Data
Jun. 30, 2005 (EP) ..................................... 05105927

(51) Int. Cl.
*A61K 31/33* (2006.01)
*C07D 487/00* (2006.01)
*C07D 255/02* (2006.01)

(52) U.S. Cl.
USPC .......................... 514/183; 540/471; 540/474

(58) Field of Classification Search
None
See application file for complete search history.

(56) References Cited

U.S. PATENT DOCUMENTS

| | | | | |
|---|---|---|---|---|
| 4,442,278 A * | 4/1984 | Giants | ........................ | 526/261 |
| 7,067,507 B2 * | 6/2006 | Pulley et al. | ................. | 514/183 |
| 2004/0116388 A1 | 6/2004 | Armistead et al. | | |
| 2004/0209895 A1 | 10/2004 | Luecking et al. | | |

FOREIGN PATENT DOCUMENTS

| | | | |
|---|---|---|---|
| WO | WO 02/083654 A1 | 10/2002 | |
| WO | WO 2004/009562 A1 | 1/2004 | |
| WO | WO 2004/037814 A1 | 5/2004 | |
| WO | WO 2004/089286 A2 | 10/2004 | |

OTHER PUBLICATIONS

Kaidanovich et al. Expert Opinion on Therapeutic Targets, 2002, 6(5), 555-561.*

Kypta. Expert Opinion on Therapeutic Patents, 2005, 15(10), 1315-1331.*

Coghlan, M.P., et al., "Selective small molecule inhibitors of glycogen synthase kinase-3 modulate glycogen metabolism and gene transcription", Chemistry & Biology, (2000), vol., 7, pp. 793-803.

Cohen, P., et al., "The renaissance of GSK3", Nature Reviews: Molecular Cell Biology, (2001), vol. 2, pp. 769-776.

D.A., et al., "Selective small-molecule inhibitors of glycogen synthase kinase-3 activity protect primary neurons from death", Journal of Neurochemistry, (2001), vol. 77, pp. 94-102.

Davies, S.P., et al., "Specificity and mechanism of action of some commonly used protein kinase inhibitors", Biochem J., (2000), vol. 351, pp. 95-105.

Embi, N., et al., "Glycogen Synthase Kinase-3 from Rabbit Skeletal Muscle Separation from Cyclic-AMP-Dependent Protein Kinase and Phosporylase Kinase", Eur. J. Biochem., (1980), vol. 107, pp. 519-527.

Gennaro Remington's Pharmaceutical Sciences, 19th ed., Mack Publishing Company, Part 8: Pharmaceutical Preparations and Their Manufacture (1990).

Greene, T.W., et al., "Protective Groups in Organic Synthesis", 3rd ed., Wiley-Interscience (1999).

(Continued)

*Primary Examiner* — Noble Jarrell

(57) ABSTRACT

The present invention concerns the compounds of formula (I), the N-oxide forms, the pharmaceutically acceptable addition salts and the stereochemically isomeric forms thereof, wherein m represents 1, n represents 1, Z represents N or C, in particular N; —$X^1$— represents $C_{1-4}$alkyl, in particular methyl; —$X^2$— represents —$C_{1-4}$alkyl- or —$C_{1-4}$alkyl-$NR^7$—, in particular propyl, -ethyl-$NR^7$— or -propyl-$NR^7$—; —Y— represents —$NR^2$—$C_{1-6}$alkyl-CO—$NR^4$—, -$Het^1$-$C_{1-6}$alkyl-CO—$NR^5$— or -$Het^2$-CO—$NR^6$— and wherein the —$C_{1-6}$alkyl-linker of —$NR^2$—$C_{1-6}$alkyl-CO—$NR^4$— or -$Het^1$-$C_{1-6}$alkyl-CO—$NR^5$— is optionally substituted with one or where possible two or more substituents selected from hydroxy, halo and phenyl; $R^1$ represents hydrogen, chloro, fluoro or bromo; $R^2$ represents —$C_{1-4}$alkyl-, in particular ethyl or methyl; $R^7$ represents hydrogen; $R^8$ represents hydrogen; $R^4$, $R^5$ and $R^6$ represent hydrogen; $Het^1$ is selected from piperazinyl or piperidinyl, in particular -piperazinyl; $Het^2$ selected from pyrrolidinyl or piperidinyl, in particular pyrrolidinyl wherein said pyrrolidinyl is optionally substituted with hydroxy.

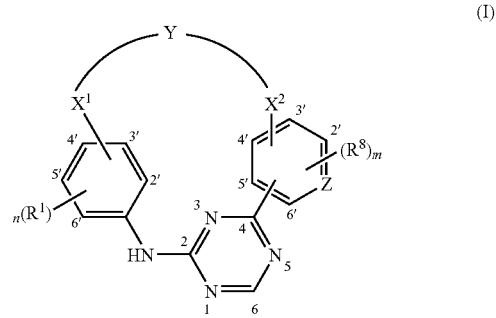

10 Claims, No Drawings

(56) References Cited

OTHER PUBLICATIONS

Kuo, G., et al., "Synthesis and Identification of [1,3,5]Triazine-pyridine Biheteroaryl as a Novel Series of Potent Cyclin-Dependent Kinase Inhibitors", J.Med.Chem., (2005), vol. 48, pp. 4535-4546.

Norman, P., "Emerging Fundamental Themes in Modern Medicinal Chemistry", Drug News Perspect, (2001), vol. 14, No. 4, pp. 242-247.

International Search Report for corresponding Patent Application No. PCT/EP2006/063555 mailed Feb. 21, 2008.

* cited by examiner

CYCLIC ANILINO—PYRIDINOTRIAZINES

CROSS REFERENCE TO RELATED APPLICATIONS

This application is a national stage application of Patent Application No. PCT/EP2006/063555, filed Jun. 26, 2006, which application claims priority from EPO Patent Application No. 05105927.7, filed Jun. 30, 2005, both of which are hereby incorporated by reference in their entirety.

Glycogen synthase kinase-3 (GSK-3) is a serine/threonine protein kinase first discovered as one of a number of kinases capable of phosphorylating and inactivating glycogen synthase, the regulatory enzyme of glycogen synthesis in mammals (Embi. et al., Eur. J. Biochem., 107, 519-527 (1980)). Existing in two isoforms, GSK-3α and GSK-3β, GSK-3 phosphorylates a wide variety of proteins in vitro. The diversity of these proteins suggests a role for GSK-3 in the control of cellular metabolism, growth and development.

Type I diabetes is characterized by a lack of insulin resulting from the destruction of insulin producing cells in the pancreas. Type II diabetes is characterized by defective insulin secretion and action. The binding of insulin to its receptor initiates a cascade of events resulting in the phosphorylation and inhibition of GSK-3, contributing to the insulin-induced stimulation of glycogen and protein synthesis. Inhibitors of GSK-3 have been shown to mimick the actions of insulin (Coghlan et al., Chem. Biol., 7, 793-803, (2000)), including the ability to lower blood glucose levels in vivo (Norman, Drug NewsPerspect., 14, 242-247 (2001)). These recent discoveries suggest that inhibitors of GSK-3 have a potential in the treatment of diabetes.

Alzheimer's disease is characterized by the micro-tubule-associated protein Tau existing in an abnormally hyperphosphorylated state (Cohen and Frame, Nature Reviews: Molecular Cell Biology, 2, 769-776 (October 2001)). GSK-3 phosphorylates many of the hyperphosphorylated sites on Tau in vitro, preventing it from binding to microtubules, making it available to undergo the aberrant filament assembly that may underlie the neuronal degradation observed in Alzheimer's disease and other neurological disorders.

Inhibitors of GSK-3, such as insulin and lithium ions, have been shown to induce a partial dephosphorylation of Tau in neuronal cells (Cross et al., J. Neurochem., 77, 94-102 (2001)). These discoveries suggest that the inhibitors of GSK-3 have a potential role in the treatment of neurodegenerative disorders such as Alzheimer's disease.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential. This population of stem cells expresses a higher level of non-cadherin associated β-catenin, which may contribute to their higher proliferative potential. Moreover, transgenic mice overexpressing a truncated β-catenin in the skin undergo de novo hair-follicle morphogenesis, which normally is only established during embryogenesis. For β-catenin it is known that it is phosphorylated by GSK-3, hence the ectopic application of GSK-3 inhibitors may therefore be therapeutically useful in the treatment of baldness and in restoring hair growth following chemotherapy-induced alopecia.

One of the other proteins regulated by GSK-3β phosphorylation is the signalling protein NF-κB. Studies on fibroblasts from GSK-3β knockout mouse indicate that inhibition of GSK-3 may be useful in treating inflammatory disorders or diseases throught the negative regulation of NF-κB activity. These diseases include autoimmune diseases and inflammatory diseases such as allergies and asthma, multiple sclerosis (MS), rheumatoid arthritis (RA), arteriosclerosis, arthritis or Inflammatory Bowel Disease (IBD).

Where GSK-3 was originally identified as a proline-directed serine/threonine kinase that phosphorylates glycogen synthase, it has now been demonstrated that GSK-3 phosphorylates numerous proteins in vitro such as the type-11 subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-Myc transcription factor, Tau protein and β-catenin. This diversity of proteins which may be phosphorylated by GSK-3 implies that GSK-3 is implicated in numerous metabolic and regulatory processes in cells.

GSK-3 inhibitors may therefore be useful in the prevention or treatment of diseases mediated through GSK-3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacutesclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. GSK3 inhibitors can also be used to inhibit sperm motility and can therefore be used as male contraceptives.

In particular, the compounds of the present invention are useful in the prevention or treatment of Alzheimer's disease; diabetes, in particular type 2 diabetes (non insulin dependent diabetes); bipolar disorder; cancer; pain, in particular neuropathic pain; depression; inflammatory diseases including allergies and asthma, MS, RA, arteriosclerosis, arthritis or IBD. More in particular, the compounds of the present invention are useful in the prevention or treatment of diabetes, in particular type 2 diabetes (non insulin dependent diabetes); pain, in particular neuropathic pain; depression; inflammatory diseases including MS, RA or IBD.

This invention relates to anilino-(pyridino)triazine derived macrocycles of formula (I) that have been found to have kinase inhibitory activity and will for example, be of value in the treatment of cell proliferation related disorders including cancer, psoriasis, benign prostatic hypertrophy, arteriosclerosis and restenosis. In particular, the compounds of the present invention were found to have an GSK3 inhibitory activity and are accordingly useful in methods of treatment of the human or animal body, for example in the manufacture of medicaments for use in the prevention or treatment of diseases mediated through GSK-3 activity supra. The invention also relates to processes for the manufacture of said anilino-(pyridino) triazine derivatives, to pharmaceutical compositions containing them and to their use in the manufacture of medicaments of use in the prevention or treatment of diseases mediated through GSK-3 activity.

This invention concerns compounds of formula (I)

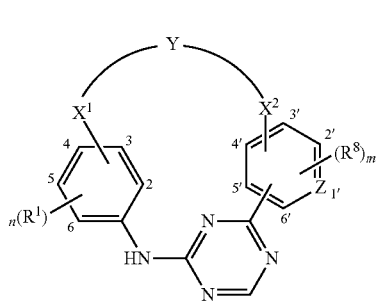

the N-oxide forms, the pharmaceutically acceptable addition salts and the stereochemically isomeric forms thereof, wherein m represents an integer from 1 to 4; n represents an integer from 1 to 4;

Z represents N or C;

Y represents $-NR^2-C_{1-6}alkyl-CO-NR^4-$, $-C_{1-4}alkyl-NR^9-C_{1-4}alkyl$, $C_{1-6}alkyl-CO-Het^{10}-$, $-Het^{11}-CO-C_{1-6}alkyl-$, $-Het^{12}-C_{1-6}alkyl-$, $-CO-Het^{13}-C_{1-6}alkyl-$, $-CO-NR^{10}-C_{1-6}alkyl-$, $-Het^1-C_{1-6}alkyl-CO-NR^5-$, or $-Het^2-CO-NR^6-$ wherein the $-C_{1-6}alkyl$-linker in $-NR^2-C_{1-6}alkyl-CO-NR^4-$ or $-Het^1-C_{1-6}alkyl-CO-NR^5-$ is optionally substituted with one or where possible two or more substituents selected from hydroxy, methoxy, aminocarbonyl, halo, phenyl, indolyl, methylsulfide, thiol, hydroxyphenyl, cyanophenyl, amino and hydroxycarbonyl;

$X^1$ represents a direct bond, $C_{1-4}alkyl$, $C_{1-4}alkyloxy$-, $C_{1-4}alkyl-CO-$, $C_{2-4}alkenyl$, $C_{2-4}alkynyl$, or $C_{1-4}alkyl-NR^3-$, wherein said $C_{1-4}alkyl$ or $C_{2-4}alkenyl$ is optionally substituted with one or where possible two or more halo substituents;

$X^2$ represents a direct bond, $C_{1-4}alkyl$, $C_{1-4}alkyloxy$-, $C_{1-4}alkyl-CO-$, $C_{2-4}alkenyl$, $C_{2-4}alkynyl$, or $C_{1-4}alkyl-NR^7-$, wherein said $C_{1-4}alkyl$ or $C_{2-4}alkenyl$ is optionally substituted with one or where possible two or more halo substituents;

$R^1$ and $R^8$ each independently represent hydrogen, $Het^{14}$, cyano, halo, hydroxy, $C_{1-6}alkoxy$-, $C_{1-6}alkyl$-, mono- or di($C_{1-4}alkyl$)amino-carbonyl-, mono- or di($C_{1-4}alkyl$)amino-sulfonyl, $C_{1-6}alkoxy$-substituted with halo or $R^1$ represents $C_{1-6}alkyl$ substituted with one or where possible two or more substituents selected from hydroxy or halo;

$R^2$ and $R^9$ each independently represents hydrogen, $C_{1-4}alkyl$, $C_{2-4}alkenyl$, $Het^3$, $Het^4$-$C_{1-4}alkyl$-, $Het^5$-$C_{1-4}alkylcarbonyl$-, mono- or di($C_{1-4}alkyl$)amino-$C_{1-4}alkyl$-carbonyl- or phenyl optionally substituted with one or where possible two or more substituents selected from hydrogen, hydroxy, amino or $C_{1-4}alkyloxy$-;

$R^3$ and $R^7$ each independently represent hydrogen, $C_{1-4}alkyl$, $Het^6$, $Het^7$-$C_{1-4}alkyl$-, $C_{2-4}alkenylcarbonyl$-optionally substituted with $Het^8$-$C_{1-4}alkylaminocarbonyl$-, $C_{2-4}alkenylsulfonyl$-, $C_{1-4}alkyloxyC_{1-4}alkyl$- or phenyl optionally substituted with one or where possible two or more substituents selected from hydrogen, hydroxy, amino or $C_{1-4}alkyloxy$-;

$R^4$, $R^5$, $R^6$ and $R^{10}$ each independently represent hydrogen or $C_{1-4}alkyl$ optionally substituted with hydroxy, $Het^9$ or $C_{1-4}alkyloxy$;

$Het^1$ and $Het^2$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^1$ and $Het^2$ are optionally substituted with amino, hydroxy, $C_{1-4}alkyl$, hydroxy-$C_{1-4}alkyl$-, phenyl, phenyl-$C_{1-4}alkyl$-, $C_{1-4}alkyl$-oxy-$C_{1-4}alkyl$-mono- or di($C_{1-4}alkyl$)amino- or amino-carbonyl-;

$Het^3$ and $Het^6$ each independently represent a heterocycle selected from pyrrolidinyl or piperidinyl wherein said $Het^3$ and $Het^6$ are optionally substituted with one or where possible two or more substituents selected from $C_{1-4}alkyl$, $C_{3-6}cycloalkyl$, hydroxy-$C_{1-4}alkyl$-, $C_{1-4}alkyloxyC_{1-4}alkyl$ or polyhydroxy-$C_{1-4}alkyl$-;

$Het^4$, $Het^7$ and $Het^9$ each independently represent a heterocycle selected from morpholinyl, pyrrolidinyl, piperazinyl or piperidinyl wherein said $Het^4$, $Het^7$ and $Het^9$ are optionally substituted with one or where possible two or more substituents selected from $C_{1-4}alkyl$, $C_{3-6}cycloalkyl$, hydroxy-$C_{1-4}alkyl$-, $C_{1-4}alkyloxyC_{1-4}alkyl$ or polyhydroxy-$C_{1-4}alkyl$-;

$Het^5$ represents a heterocycle selected from morpholinyl, pyrrolidinyl, piperazinyl or piperidinyl wherein said $Het^5$ is optionally substituted with one or where possible two or more substituents selected from $C_{1-4}alkyl$, $C_{3-6}cycloalkyl$, hydroxy-$C_{1-4}alkyl$-, $C_{1-4}alkyloxyC_{1-4}alkyl$ or polyhydroxy-$C_{1-4}alkyl$-;

$Het^{10}$, $Het^{11}$ and $Het^{13}$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^{10}$, $Het^{11}$ and $Het^{13}$ are optionally substituted with amino, hydroxy, $C_{1-4}alkyl$, hydroxy-$C_{1-4}alkyl$-, phenyl, phenyl-$C_{1-4}alkyl$-, $C_{1-4}alkyl$-oxy-$C_{1-4}alkyl$-, amino-carbonyl- or mono- or di($C_{1-4}alkyl$)amino-;

$Het^{12}$ represents a heterocycle selected from pyrrolidinyl, piperidinyl, piperazinyl, pyridinyl, pyrimidinyl, pyrazinyl, imidazolidinyl or pyrazolidinyl wherein said $Het^{12}$ is optionally substituted with amino, hydroxy, $C_{1-4}alkyl$, hydroxy-$C_{1-4}alkyl$-, phenyl, phenyl-$C_{1-4}alkyl$-, $C_{1-4}alkyl$-oxy-$C_{1-4}alkyl$-; mono- or di($C_{1-4}alkyl$)amino- or amino-carbonyl-;

$Het^{14}$ represents a heterocycle selected from morpholinyl; pyrrolidinyl; piperazinyl; imidazolyl; pyrrolyl; 2,3,4-triazapyrrolyl; 1,2,3-triazolyl; pyrazolyl; or piperidinyl wherein said $Het^{14}$ is optionally substituted with one or where possible two or more substituents selected from $C_{1-4}alkyl$, $C_{3-6}cycloalkyl$, hydroxy-$C_{1-4}alkyl$-, $C_{1-4}alkyloxyC_{1-4}alkyl$ or polyhydroxy-$C_{1-4}alkyl$-; in particular $Het^{14}$ represents a heterocycle selected from morpholinyl; pyrrolidinyl; pyrrolyl; 2,3,4-triazapyrrolyl; piperazinyl or piperidinyl wherein said $Het^{14}$ is optionally substituted with one or where possible two or more substituents selected from $C_{1-4}alkyl$, $C_{3-6}cycloalkyl$, hydroxy-$C_{1-4}alkyl$-, $C_{1-4}alkyloxyC_{1-4}alkyl$ or polyhydroxy-$C_{1-4}alkyl$-; more I particular $Het^{14}$ represents a heterocycle selected from morpholinyl; pyrrolidinyl; piperazinyl or piperidinyl wherein said $Het^{14}$ is optionally substituted with one or where possible two or more substituents selected from $C_{1-4}alkyl$, $C_{3-6}cycloalkyl$, hydroxy-$C_{1-4}alkyl$-, $C_{1-4}alkyloxyC_{1-4}alkyl$ or polyhydroxy-$C_{1-4}alkyl$-.

As used in the foregoing definitions and hereinafter, halo is generic to fluoro, chloro, bromo and iodo;

$C_{1-4}alkyl$ defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;

$C_{1-6}alkyl$ is meant to include $C_{1-5}alkyl$ and the higher homologues thereof having 6 carbon atoms such as, for example hexyl, 1,2-dimethylbutyl, 2-methylpentyl and the like;

$C_{2-4}$alkenyl defines straight and branched chain hydrocarbon radicals containing one double bond and having from 2 to 4 carbon atoms such as, for example vinyl, 2-propenyl, 3-butenyl, 2-butenyl and the like;

$C_{2-6}$alkynyl defines straight and branched chain hydrocarbon radicals containing one triple bond and having from 2 to 6 carbon atoms such as, for example, ethynyl, 2-propynyl, 3-butynyl, 2-butynyl, 2-pentynyl, 3-pentynyl, 3-methyl-2-butynyl, 3-hexynyl and the like;

$C_{3-6}$cycloalkyl is generic to cyclopropyl, cyclobutyl, cyclopentyl and cyclohexyl;

$C_{1-4}$alkyloxy defines straight or branched saturated hydrocarbon radicals such as methoxy, ethoxy, propyloxy, butyloxy, 1-methylethyloxy, 2-methylpropyloxy and the like;

$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;

polyhydroxy-$C_{1-4}$alkyl is generic to a $C_{1-4}$alkyl as defined hereinbefore, having two, three or were possible more hydroxy substituents, such as for example trihydroxymethyl;

polyhalo-$C_{1-4}$alkyl is generic to a $C_{1-4}$alkyl as defined hereinbefore, having two, three or were possible more halo substituents, such as for example trifluoromethyl;

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove are meant to comprise the therapeutically active non-toxic acid addition salt forms that the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, trifluoroacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

A first group of compounds according to the present invention consists of those compounds of formula (I) wherein one or more of the following restrictions apply;

m represents an integer from 1 to 4; n represents an integer from 1 to 4;

Z represents N or C;

Y represents —$NR^2$—$C_{1-6}$alkyl-CO—$NR^4$—, -$Het^1$-$C_{1-6}$alkyl-CO—$NR^5$—, or -$Het^2$-CO—$NR^6$— wherein the —$C_{1-6}$alkyl-linker in —$NR^2$—$C_{1-6}$alkyl-CO—$NR^4$— or -$Het^1$-$C_{1-6}$alkyl-CO—$NR^5$— is optionally substituted with one or where possible two or more substituents selected from hydroxy, halo, phenyl, indolyl, methylsulfide, thiol, hydroxyphenyl, amino and hydroxycarbonyl;

$X^1$ represents a direct bond, $C_{1-4}$alkyl, $C_{2-4}$alkenyl, $C_{2-4}$alkynyl, or $C_{1-4}$alkyl-$NR^3$—, wherein said $C_{1-4}$alkyl or $C_{2-4}$alkenyl is optionally substituted with one or where possible two or more halo substituents;

$X^2$ represents a direct bond, $C_{1-4}$alkyl, $C_{2-4}$alkenyl, $C_{2-4}$alkynyl, or $C_{1-4}$alkyl-$NR^7$—, wherein said $C_{1-4}$alkyl or $C_{2-4}$alkenyl is optionally substituted with one or where possible two or more halo substituents;

$R^1$ and $R^8$ each independently represent hydrogen, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl)amino-sulfonyl, $C_{1-6}$alkoxy-substituted with halo or $R^1$ represents $C_{1-6}$alkyl substituted with one or where possible two or more substituents selected from hydroxy or halo;

$R^2$ represents hydrogen, $C_{1-4}$alkyl, $Het^3$, $Het^4$-$C_{1-4}$alkyl-, $Het^5$-$C_{1-4}$alkylcarbonyl-, mono- or di($C_{1-4}$alkyl)amino-$C_{1-4}$alkyl-carbonyl- or phenyl optionally substituted with one or where possible two or more substituents selected from hydrogen, hydroxy, amino or $C_{1-4}$alkyloxy-;

$R^3$ and $R^7$ each independently represent hydrogen, $C_{1-4}$alkyl, $Het^6$, $Het^7$-$C_{1-4}$alkyl-, $C_{2-4}$alkenylcarbonyl-optionally substituted with $Het^8$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^4$, $R^5$ and $R^6$ each independently represent hydrogen or $C_{1-4}$alkyl optionally substituted with hydroxy, $Het^9$ or $C_{1-4}$alkyloxy;

$Het^1$ and $Het^2$ each independently represent a heterocycle selected from pyrrolidinyl, piperidinyl, piperazinyl, pyridinyl, pyrimidinyl, pyrazinyl, imidazolidinyl or pyrazolidinyl wherein said $Het^1$ is optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

$Het^3$, $Het^6$ and $Het^9$ each independently represent a heterocycle selected from morpholinyl, pyrrolidinyl, piperazinyl or piperidinyl wherein said $Het^3$, $Het^6$ and $Het^9$ are optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^4$ and $Het^7$ each independently represent a heterocycle selected from morpholinyl, pyrrolidinyl, piperazinyl or piperidinyl wherein said $Het^4$ and $Het^7$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^5$ represents a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-.

A second group of compounds according to the present invention consists of those compounds of formula (I) wherein one or more of the following restrictions apply;

m represents 1; n represents 1; Z represents N or C, in particular N;

Y represents —$NR^2$—$C_{1-6}$alkyl-CO—$NR^4$—, —$C_{1-4}$alkyl-$NR^9$—$C_{1-4}$alkyl-, $C_{1-6}$alkyl-CO-$Het^{10}$-, -$Het^{11}$-CO—$C_{1-6}$alkyl-, -$Het^{12}$-$C_{1-6}$alkyl-, —CO-$Het^{13}$-$C_{1-6}$alkyl-, —CO—$NR^{10}$—$C_{1-6}$alkyl-, -$Het^1$-$C_{1-6}$alkyl-CO—$NR^5$—, -$Het^2$-CO—$NR^6$— wherein the —$C_{1-6}$alkyl-linker in —$NR^2$—$C_{1-6}$alkyl-CO—$NR^4$— or -$Het^1$-$C_{1-6}$alkyl-CO—$NR^5$— is optionally substituted with one or where possible two or more substituents selected from hydroxy, methoxy, aminocarbonyl, halo, cyanophenyl and phenyl;

$X^1$ represents a direct bond, —$C_{1-4}$alkyl-, $C_{1-4}$alkyloxy- or $C_{1-4}$alkyl-$NR^3$;

$X^2$ represents a direct bond, $C_{1-4}$alkyl, $C_{1-4}$alkyloxy-, $C_{1-4}$alkyl-CO—, $C_{2-4}$alkenyl, $C_{2-4}$alkynyl or $C_{1-4}$alkyl-$NR^7$— wherein said $C_{2-4}$alkenyl is optionally substituted with one or where possible two or more halo substituents;

$R^1$ represents hydrogen, $Het^{14}$ or halo;

$R^2$ represents hydrogen, $C_{1-4}$alkyl, $C_{2-4}$alkenyl or $Het^4$-$C_{1-4}$alkyl-;

$R^3$ and $R^7$ each independently represent hydrogen or $C_{1-4}$alkyl;

$R^8$ represents hydrogen;

$R^9$ represents hydrogen or $C_{1-4}$alkyl; in particular $R^9$ represents, hydrogen, methyl, ethyl or isopropyl; mor in particular hydrogen, methyl or ethyl;

$R^4$, $R^5$, $R^6$ and $R^{10}$ each independently represent hydrogen or $C_{1-4}$alkyl;

$Het^1$ and $Het^2$ each independently represent pyrrolidinyl, piperidinyl or piperazinyl wherein said $Het^1$ or $Het^2$ is optionally substituted with hydroxy; in particular $Het^1$ represents pyrrolidinyl or piperazinyl and $Het^2$ represents piperidinyl, piperazinyl or pyrrolidinyl wherein said pyrrolidinyl is optionaly substituted with hydroxy;

$Het^4$ represents piperazinyl optionally substituted with $C_{1-4}$alkyl;

$Het^{10}$, $Het^{11}$, $Het^{12}$ and $Het^{13}$ each independently represent pyrrolidinyl, piperidinyl or piperazinyl wherein said $Het^{10}$, $Het^{11}$, $Het^{12}$ and $Het^{13}$ are optionally substituted with hydroxy; in particular $Het^{10}$, $Het^{11}$, $Het^{12}$ and $Het^{13}$ represent piperazinyl;

$Het^{14}$ represents morpholinyl; pyrrolidinyl; pyrrolyl; 1,2,3-triazolyl; 2,3,4-triazapyrrolyl; piperidinyl or piperazinyl wherein said $Het^{14}$ is optionally substituted with $C_{1-4}$alkyl; in particular $Het^{14}$ represents morpholinyl; pyrrolidinyl; piperidinyl or piperazinyl; more in particular $Het^{14}$ represents morpholinyl.

A third group of compounds according to the present invention consists of those compounds of formula (I) wherein one or more of the following restrictions apply;

m represents 1; n represents 1; Z represents N or C, in particular N;

Y represents —$NR^2$—$C_{1-6}$alkyl-CO—$NR^4$—, -$Het^1$-$C_{1-6}$alkyl-CO—$NR^5$—, -$Het^2$-CO—$NR^6$— wherein the —$C_{1-6}$ alkyl-linker in —$NR^2$—$C_{1-6}$alkyl-CO—$NR^4$— or -$Het^1$-$C_{1-6}$alkyl-CO—$NR^5$— is optionally substituted with one or where possible two or more substituents selected from hydroxy, halo and phenyl;

$X^1$ represents —$C_{1-4}$alkyl- or $C_{1-4}$alkyl-$NR^3$;

$X^2$ represents a $C_{1-4}$alkyl, $C_{2-4}$alkenyl, $C_{2-4}$alkynyl or $C_{1-4}$alkyl-$NR^7$— wherein said $C_{2-4}$alkenyl is optionally substituted with one or where possible two or more halo substituents;

$R^1$ represents hydrogen or halo;

$R^8$ represents hydrogen;

$R^2$ represents hydrogen, $C_{1-4}$alkyl, or $Het^4$-$C_{1-4}$alkyl-;

$R^3$ and $R^7$ each independently represent hydrogen or $C_{1-4}$alkyl;

$R^4$, $R^5$ and $R^6$ each independently represent hydrogen or $C_{1-4}$alkyl;

$Het^1$ and $Het^2$ each independently represent pyrrolidinyl, piperidinyl or piperazinyl wherein said $Het^1$ or $Het^2$ is optionally substituted with hydroxy;

$Het^4$ represents piperazinyl optionally substituted with $C_{1-4}$alkyl.

A further group of compounds according to the present invention consists of those compounds of formula (I) wherein one or more of the following restrictions apply;

—$X^1$— represents $C_{1-4}$alkyl, in particular methyl;

—$X^2$— represents —$C_{1-4}$alkyl- or —$C_{1-4}$alkyl-$NR^7$—, in particular propyl, -ethyl-$NR^7$— or -propyl-$NR^7$—;

—Y— represents-$NR^2$—$C_{1-6}$alkyl-CO—$NR^4$—, -$Het^1$-$C_{1-6}$alkyl-CO—$NR^5$— or -$Het^2$-CO—$NR^6$— and wherein the —$C_{1-6}$alkyl-linker of —$NR^2$—$C_{1-6}$alkyl-CO—$NR^4$— or -$Het^1$-$C_{1-6}$alkyl-CO—$NR^5$— is optionally substituted with one or where possible two or more substituents selected from hydroxy, halo and phenyl;

$R^1$ represents hydrogen, chloro, fluoro or bromo;

$R^2$ represents —$C_{1-4}$alkyl-, in particular ethyl or methyl;

$R^7$ represents hydrogen;

$R^8$ represents hydrogen;

$R^4$, $R^5$ and $R^6$ represent hydrogen;

$Het^1$ is selected from piperazinyl or piperidinyl, in particular -piperazinyl;

$Het^2$ selected from pyrrolidinyl or piperidinyl, in particular pyrrolidinyl wherein said pyrrolidinyl is optionally substituted with hydroxy.

A fourth group of compounds according to the present invention consists of those compounds of formula (I) wherein one or more of the following restrictions apply;

m represents 1; n represents 1; Z represents N or C, in particular N;

Y represents —NR$^2$—C$_{1-6}$alkyl-CO—NR$^4$—, -Het$^{11}$-CO—C$_{1-6}$alkyl-, —CO-Het$^{13}$-C$_{1-6}$alkyl-, —CO—NR$^{10}$—C$_{1-6}$alkyl-, -Het$^1$-C$_{1-6}$alkyl-CO—NR$^5$—, or -Het$^2$-CO—NR$^6$— wherein the —C$_{1-6}$alkyl-linker in —NR$^2$—C$_{1-6}$alkyl-CO—NR$^4$— or -Het$^1$-C$_{1-6}$alkyl-CO—NR$^5$— is optionally substituted with hydroxy;

X$^1$ represents —C$_{1-4}$alkyl-, C$_{1-4}$alkyloxy- or C$_{1-4}$alkyl-NR$^3$;

X$^2$ represents a direct bond, C$_{1-4}$alkyl, C$_{1-4}$alkyloxy or C$_{1-4}$alkyl-NR$^7$—;

R$^1$ represents hydrogen or halo;

R$^8$ represents hydrogen or halo;

R$^2$ represents hydrogen, C$_{1-4}$alkyl, or Het$^4$-C$_{1-4}$alkyl-;

R$^3$ and R$^7$ each independently represent hydrogen or C$_{1-4}$alkyl;

R$^4$, R$^5$, R$^6$ and R$^{10}$ each independently represent hydrogen or C$_{1-4}$alkyl;

Het$^1$ and Het$^2$ each independently represent pyrrolidinyl, piperidinyl or piperazinyl wherein said Het$^1$ or Het$^2$ is optionally substituted with hydroxy;

Het$^4$ represents piperazinyl optionally substituted with C$_{1-4}$alkyl;

Het$^{11}$ represents piperidinyl or piperazinyl; in particular piperazinyl;

Het$^{13}$ represents piperidnyl or piperazinyl; in particular piperazinyl.

It is also an object of the present invention to provide those compounds of formula (I) wherein one or more of the following restrictions apply;

m represents 1; n represents 1; Z represents N or C;

Y represents —C$_{1-4}$alkyl-NR$^9$—C$_{1-4}$alkyl-, —NR$^2$—C$_{1-6}$alkyl-CO—NR$^4$—, -Het$^1$-C$_{1-6}$alkyl-CO—NR$^5$— or Het$^2$-CO—NR$^6$— wherein the C$_{1-6}$alkyl linker in —Y— is optionally substituted with one or where possible two or more substituents selected from hydroxy, halo or phenyl;

X$^1$ represents C$_{1-4}$alkyl or C$_{1-4}$alkyloxy-; in particular ethyl or ethoxy;

X$^2$ represents C$_{1-4}$alkyl, C$_{1-4}$alkyloxy, or —NR$^7$—C$_{1-4}$alkyl; in particular propyl, —NR$^7$-ethyl- or NR$^7$-propyl-;

R$^1$ represents hydrogen, chloro, fluoro or bromo;

R$^2$ represents hydrogen, C$_{1-4}$alkyl or C$_{2-4}$alkenyl;

R$^4$ represents hydrogen; R$^5$ represents hydrogen or C$_{1-4}$alkyl;

R$^6$ represents hydrogen or C$_{1-4}$alkyl; R$^7$ represents hydrogen or C$_{1-4}$alkyl;

R$^8$ represents hydrogen, chloro, fluoro or bromo;

R$^9$ represents hydrogen or C$_{1-4}$alkyl;

Het$^1$ represents piperazinyl or piperidinyl;

Het$^2$ represents pyrrolidinyl, piperidinyl or piperazinyl wherein said Het$^2$ is optionally substituted with hydroxy.

In a further embodiment of the present invention the compounds of formula (I) are selected from the group consisting of;

14-methyl-3,5,7,14,17,22,27-heptaazatetracyclo [19.3.1.1~2,6~0.1~8,12~]heptacosa-1(25),2(27),3,5,8 (26),9,11,21,23-nonaen-19-yn-16-one;

(19Z)-19-chloro-14-methyl-3,5,7,14,17,22,27-heptaazatetracyclo[19.3.1.1~2,6~0.1~8,12~]heptacosa-1(25),2(27), 3,5,8(26),9,11,19,21,23-decaen-16-one;

14-methyl-3,5,7,14,17,22,27-heptaazatetracyclo [19.3.1.1~2,6~0.1~8,12~]heptacosa-1(25),2(27),3,5,8 (26),9,11,21,23-nonaen-16-one;

1,8,10,12,17,22,26,32-octaazapentacyclo[24.2.2.1~3, 7~0.1~9,13~0.1~14,18~]tritriaconta-3(33),4,6,9(32),10, 12,14(31),15,17-nonaen-23-one;

1,8,10,12,17,22,25,31-octaazapentacyclo[23.2.2.1~3, 7~0.1~9,13~0.1~14,18~]dotriaconta-3(32),4,6,9(31),10, 12,14(30),15,17-nonaen-23-one;

17-methyl-3,5,7,14,17,22,27-heptaazatetracyclo [19.3.1.1~2,6~0.1~8,12~]heptacosa-1(25),2(27),3,5,8 (26),9,11,21,23-nonaen-15-one;

18-methyl-3,5,7,15,18,23,28-heptaazatetracyclo [20.3.1.1~2,6~0.1~8,12~]octacosa-1(26),2(28),3,5,8(27), 9,11,22,24-nonaen-16-one;

14-methyl-3,5,7,14,17,20,22,27-octaazatetracyclo [19.3.1.1~2,6~0.1~8,12~]heptacosa-1(25),2(27),3,5,8 (26),9,11,21,23-nonaen-16-one;

14-methyl-3,5,7,14,17,21,23,28-octaazatetracyclo [20.3.1.1~2,6~0.1~8,12~]octacosa-1(26),2(28),3,5,8(27), 9,11,22,24-nonaen-16-one;

18-ethyl-3,5,7,15,18,23,28-heptaazatetracyclo[20.3.1.1~2, 6~0.1~8,12~]octacosa-1(26),2(28),3,5,8(27),9,11,22,24-nonaen-16-one;

5-chloro-1,8,10,12,17,22,30-heptaazapentacyclo [22.2.2.1~3,7~0.1~9,13~0.1~14,18~]hentriaconta-3(31), 4,6,9(30),10,12,14(29),15,17-nonaen-23-one;

5-chloro-1,8,10,12,17,22,25,31-octaazapentacyclo [23.2.2.1~3,7~0.1~9,13~0.1~14,18~]dotriaconta-3(32),4, 6,9(31),10,12,14(30),15,17-nonaen-23-one;

10-chloro-14-methyl-3,5,7,14,17,22,27-heptaazatetracyclo [19.3.1.1~2,6~0.1~8,12~]heptacosa-1(25),2(27),3,5,8 (26),9,11,21,23-nonaen-16-one;

10-chloro-14-ethyl-3,5,7,14,17,22,27-heptaazatetracyclo [19.3.1.1~2,6~0.1~8,12~]heptacosa-1(25),2(27),3,5,8 (26),9,11,21,23-nonaen-16-one;

22-oxa-3,5,7,14,19,31-hexaazapentacyclo[21.2.2.2~14, 17~0.1~2,6~0.1~8,12~]hentriaconta-2,4,6(31),8,10,12 (30),23,25,26-nonaen-18-one;

13-oxa-3,5,7,16,21,26-hexaazatetracyclo[18.3.1.1~2, 6~0.1~8,12~]hexacosa-1(24),2,4,6(26),8,10,12(25),20, 22-nonaen-15-one;

13-oxa-3,5,7,16,19,22,27-heptaazatetracyclo[19.3.1.1~2, 6~0.1~8,12~]heptacosa-1(25),2,4,6(27),8,10,12(26),21, 23-nonaen-17-one, 19-methyl-;

1,5,10,12,14,21,24,30-octaazapentacyclo[22.2.2.1~4, 8~0.1~9,13~0.1~15,19~]hentriaconta-4,6,8(31),9,11,13 (30),15,17,19(29)-nonaen-23-one, 21-methyl-;

21-oxa-1,6,11,13,15,24,30-heptaazapentacyclo[22.2.2.1~5, 9~0.1~10,14~0.1~16,20~]hentriaconta-5,7,9(31),10,12, 14(30),16,18,20(29)-nonaen-23-one;

13,9-metheno-19,15-nitrilo-14H-pyrido[3,2-g][1,3,5,9,12, 15]hexaazacycloheneicosin-5(6H)-one, 1,2,3,4,7,8-hexahydro-7-(2-propenyl)-;

1,8,10,12,22,25,31-heptaazapentacyclo[23.2.2.1~3, 7~0.1~9,13~0.1~14,18~]dotriaconta-3,5,7(32),9,11,13 (31),14,16,18(30)-nonaen-23-one, 17-fluoro-;

3,5,7,14,17,22,27-heptaazatetracyclo[19.3.1.1~2,6~0.1~8, 12~]heptacosa-1(25),2,4,6(27),8,10,12(26),21,23-nonaen-16-one, 14-(1-methylethyl)-;

3,5,7,14,17,27-hexaazatetracyclo[19.3.1.1~2,6~0.1~8,12~] heptacosa-1(25),2,4,6(27),8,10,12(26),21,23-nonaen-15-one, 22-fluoro-17-methyl-;

3,5,7,14,17,27-hexaazatetracyclo[19.3.1.1~2,6~0.1~8,12~] heptacosa-1(25),2,4,6(27),8,10,12(26),21,23-nonaen-16-one, 10-chloro-22-fluoro-15-(hydroxymethyl)-, (15S)—;

3,5,7,14,17,21,28-heptaazatetracyclo[20.3.1.1~2,6~0.1~8, 12~]octacosa-1(26),2,4,6(28),8,10,12(27),22,24-nonaen-16-one, 15-(phenylmethyl)-, (15S)—;

11,7-metheno-6,2-nitrilo-1H-1,3,5,15,18-benzopentaazacycloheneicosin-17(12H)-one, 13,14,15,16,18,19-hexahydro-16-methyl-, (16R)—;

3,5,7,14,17,23,27-heptaazatetracyclo[19.3.1.1~2,6~0.1~8, 12~]heptacosa-1(25),2,4,6(27),8,10,12(26),21,23-nonaen-16-one;

1,8,10,12,16,22,25,31-octaazapentacyclo[23.2.2.1~3, 7~0.1~9,13~0.1~14,18~]dotriaconta-3,5,7(32),9,11,13 (31),14,16,18(30)-nonaen-23-one;

3,5,7,14,17,23,27-heptaazatetracyclo[19.3.1.1~2,6~0.1~8, 12~]heptacosa-1(25),2,4,6(27),8,10,12(26),21,23-nonaen-16-one, 15-(hydroxymethyl)-, (15S)—;

3,5,7,14,18,21,26-heptaazatetracyclo[18.3.1.1~2,6~0.1~8, 12~]hexacosa-1(24),2,4,6(26),8,10,12(25),20,22-nonaen-17-one, 14-methyl-;

3,5,7,14,17,22,27-heptaazatetracyclo[19.3.1.1~2,6~0.1~8, 12~]heptacosa-1(25),2,4,6(27),8,10,12(26),21,23-nonaen-16-one, 14,17-dimethyl-;

3,5,7,14,18,24,29-heptaazatetracyclo[21.3.1.1~2,6~0.1~8, 12~]nonacosa-1(27),2,4,6(29),8,10,12(28),23,25-nonaen-17-one, 14-methyl-(HCl-salt);

3,5,7,14,17,22,27-heptaazatetracyclo[19.3.1.1~2,6~0.1~8, 12~]heptacosa-1(25),2,4,6(27),8,10,12(26),21,23-nonaen-16-one, 15-(hydroxymethyl)-, (15S)—;

including the N-oxide forms, the pharmaceutically acceptable addition salts and the stereochemically active forms thereof.

In an even further embodiment the compounds of formula (I) are selected from the trifluoroacetic acid salts of;

18-ethyl-3,5,7,15,18,23,28-heptaazatetracyclo[20.3.1.1~2, 6~0.1~8,12~]octacosa-1(26),2(28),3,5,8(27),9,11,22,24-nonaen-16-one;

14-methyl-3,5,7,14,17,21,23,28-octaazatetracyclo [20.3.1.1~2,6~0.1~8,12~]octacosa-1(26),2(28),3,5,8(27), 9,11,22,24-nonaen-16-one;

1,8,10,12,17,22,25,31-octaazapentacyclo[23.2.2.1~3, 7~0.1~9,13~0.1~14,18~]dotriaconta-3(32),4,6,9(31),10, 12,14(30),15,17-nonaen-23-one;

14-methyl-3,5,7,14,17,20,22,27-octaazatetracyclo [19.3.1.1~2,6~0.1~8,12~]heptacosa-1(25),2(27),3,5,8 (26),9,11,21,23-nonaen-16-one;

14-methyl-3,5,7,14,17,22,27-heptaazatetracyclo [19.3.1.1~2,6~0.1~8,12~]heptacosa-1(25),2(27),3,5,8 (26),9,11,21,23-nonaen-16-one;

1,8,10,12,22,25,31-heptaazapentacyclo[23.2.2.1~3, 7~0.1~9,13~0.1~14,18~]dotriaconta-3,5,7(32),9,11,13 (31),14,16,18(30)-nonaen-23-one, 17-fluoro-;

3,5,7,14,17,22,27-heptaazatetracyclo[19.3.1.1~2,6~0.1~8, 12~]heptacosa-1(25),2,4,6(27),8,10,12(26),21,23-nonaen-16-one, 14-(1-methylethyl)-;

3,5,7,14,17,27-hexaazatetracyclo[19.3.1.1~2,6~0.1~8,12~] heptacosa-1(25),2,4,6(27),8,10,12(26),21,23-nonaen-15-one, 22-fluoro-17-methyl-;

3,5,7,14,17,27-hexaazatetracyclo[19.3.1.1~2,6~0.1~8,12~] heptacosa-1(25),2,4,6(27),8,10,12(26),21,23-nonaen-16-one, 10-chloro-22-fluoro-15-(hydroxymethyl)-, (15S)—;

3,5,7,14,17,23,27-heptaazatetracyclo[19.3.1.1~2,6~0.1~8, 12~]heptacosa-1(25),2,4,6(27),8,10,12(26),21,23-nonaen-16-one;

1,8,10,12,16,22,25,31-octaazapentacyclo[23.2.2.1~3, 7~0.1~9,13~0.1~14,18~]dotriaconta-3,5,7(32),9,11,13 (31),14,16,18(30)-nonaen-23-one;

3,5,7,14,17,23,27-heptaazatetracyclo[19.3.1.1~2,6~0.1~8, 12~]heptacosa-1(25),2,4,6(27),8,10,12(26),21,23-nonaen-16-one, 15-(hydroxymethyl)-, (15S)—; or 1,8,10,12,17,22,26,32-octaazapentacyclo[24.2.2.1~3, 7~0.1~9,13~0.1~14,18~]tritriaconta-3(33),4,6,9(32),10, 12,14(31),15,17-nonaen-23-one.

Other special group of compounds are:

those compounds of formula (I) wherein —$X^1$— represents $C_{1-4}$alkyl, in particular methyl;

those compounds of formula (I) wherein —$X^1$— represents —$C_{1-4}$alkyloxy-, in particular ethoxy or propyloxy;

those compounds of formula (I) wherein —$X^2$— represents —$C_{1-4}$alkyl-, in particular propyl;

those compounds of formula (I) wherein —$X^2$— represents —$C_{1-4}$alkyloxy-, in particular ethoxy or propyloxy;

those compounds of formula (I) wherein —$X^2$— represents —$C_{1-4}$alkyl-$NR^7$—, in particular -ethyl-$NR^7$— and -propyl-$NR^7$—;

those compounds of formula (I) wherein Y represents $C_{1-4}$alkyl-$NR^9$—$C_{1-4}$alkyl- and $R^9$ represents hydrogen or ethyl;

those compounds of formula (I) wherein —Y— represents-$NR^2$—$C_{1-6}$alkyl-CO—$NR^4$— wherein said $C_{1-6}$alkyl linker is optionally substituted with one or where possible two or more substituents selected from hydroxy, halo and phenyl; in particular those compounds of formula (I) wherein —Y— represents-$NR^2$—$C_{1-6}$alkyl-CO—$NR^4$—; wherein $R^2$ represent hydrogen, ethyl, isopropyl, 2-propenyl or methyl and wherein $R^4$ represents hydrogen or methyl; more in particular those compounds of formula (I) wherein —Y— represents —$NR^2$—$C_{1-6}$alkyl-CO—$NR^4$—; $R^2$ represent hydrogen, ethyl or methyl and wherein $R^4$ represents hydrogen or methyl;

those compounds of formula (I) wherein —Y— represents -$Het^1$-$C_{1-6}$alkyl-CO—$NR^5$— with $Het^1$ selected from piperazinyl or piperidinyl; $R^5$ represents hydrogen or methyl and wherein the $C_{1-6}$alkyl linker is optionally substituted with one or where possible two or more substituents selected from hydroxy, halo and phenyl; in particular Y represents -piperazinyl-ethyl-CO—$NR^5$—;

those compounds of formula (I) wherein —Y— represents -$Het^2$-CO—$NR^6$— with $Het^2$ selected from pyrrolidinyl, piperazinyl or piperidinyl and $R^6$ from hydrogen or methyl, in particular $Het^2$ represents pyrrolidinyl wherein said pyrrolidinyl is optionally substituted with hydroxy;

those compounds of formula (I) wherein $Het^1$ represents piperazinyl or piperidinyl;

those compounds of formula (I) wherein $Het^2$ represents pyrrolidinyl, piperidinyl or piperazinyl, wherein said $Het^2$ is optionally substituted with hydroxy;

those compounds of formula (I) wherein $R^1$ represents hydrogen, chloro, fluoro or bromo.

those compounds of formula (I) wherein $R^8$ represents hydrogen, chloro, fluoro or bromo.

those compounds of formula (I) wherein $R^2$ represents hydrogen, —$C_{1-4}$alkyl- or $C_{2-4}$alkenyl, in particular hydrogen, enthyl, methyl or 2-propenyl or $R^2$ represents hydrogen or —$C_{1-4}$alkyl, more in particular hydrogen, ethyl or methyl;

those compounds of formula (I) wherein the —$C_{1-6}$alkyl-linker in —Y— is optionally substituted with one or where possible two or more substituents selected from hydroxy and phenyl.

In a further embodiment of the present invention the $X^1$ substituent is at position 3, the $R^1$ substituent represents hydrogen or halo and is at position 5, the triazine ring is attached to the Z comprising ring at position 4' and the $X^2$ substituent is at position 2' of the structure of formula (I). In an even further embodiment, for those compounds of formula (I) wherein Z represents C, the $X^1$ substituent is at position 3, the $R^1$ substituent represents hydrogen or halo and is at position 5, the triazine ring is attached to the Z comprising ring at position 4', the $X^2$ substituent is at position 2' and the $R^8$ substituent is at position 1'.

In another embodiment of the present invention the $X^1$ substituent is at position 3, the $R^1$ substituent represents hydrogen or halo and is at position 5, the triazine ring is attached to the Z comprising ring at position 5' and the $X^2$ substituent is at position 3' of the structure of formula (I). In an even further embodiment, for those compounds of formula (I) wherein Z represents C, the $X^1$ substituent is at position 3, the $R^1$ substituent represents hydrogen or halo and is at position 5, the triazine ring is attached to the Z comprising ring at position 5', the $X^2$ substituent is at position 3' and the $R^8$ substituent is at position 1'.

The compounds of this invention can be prepared by any of several standard synthetic processes commonly used by those skilled in the art of organic chemistry and include both solution phase and solid phase chemistry techniques. As will be exemplified in more detail in the exemplary part hereinafter, the compounds of the present invention are generally prepared from aniline-4-pyridyltriazines of formula II or III in a 3 steps reaction comprising;

Scheme 1

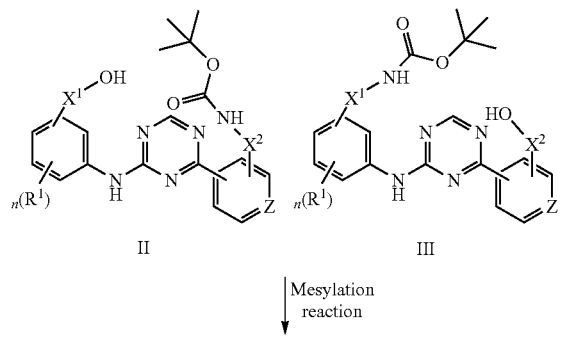

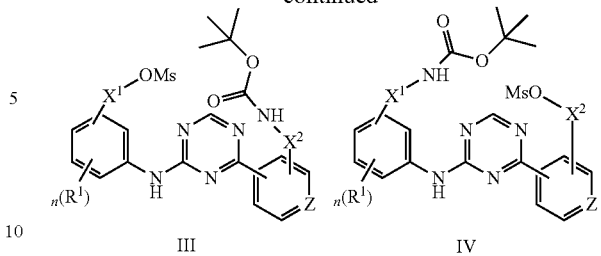

wherein Z, n, $X^1$, $X^2$ and $R^1$ are defined as for the compounds of formula (I) hereinbefore.

i) in a first step a conversion of the alcohol in a better leaving group, such as for example, by mesylation with $MeSO_2Cl$ (MsCl) to yield the corresponding mesylates of formulas IV and V. This mesylation reaction is typically performed in an appropriate reaction inert solvent such as for example $CH_3CN$ or DMF in the presence of a base such as pyridine or N,N-diisopropylethylamine (DIPEA), by stirring the reaction mixture for 5-30 minutes, in particular 5 to 15 minutes at room temperature;

ii) amination of the thus obtained mesylate with an appropriate amino acid ester of general formula (V) yields the intermediates of general formulas VI or VII. This ammination reaction is typically performed in a reaction inert solvent such as for example $CH_3CN$ or DMF in the presence of a base such as dimethylamine or N,N-diisopropylethylamine (DIPEA) and stirring said reaction mixture overnight at an elevated temperature in the range of 50-70° C., typically 60-65° C. Excess of amine is finally removed from the reaction mixture using polymer supported amine scavengers such as polymer supported isocyanate (PS-NCO) or polymer supported methylisatoic anhydride (PM-MIA);

Scheme 2

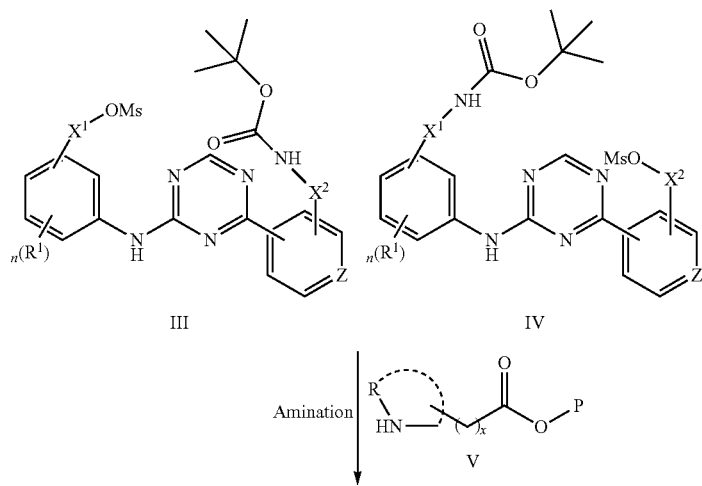

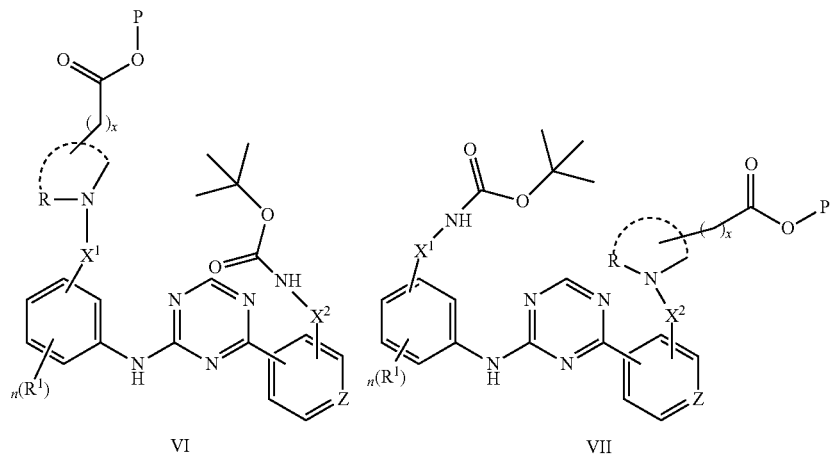

VI VII wherein n, Z, $X^1$, $X^2$ and $R^1$ are defined as for the compounds of formula (I) hereinbefore, and wherein x represents 0, 1, 2 or 3; P represents a protective group such as for example methylcarbonyl, t-butyl, methyl, ethyl, benzyl or trialkylsilyl groups; R represents $R^2$ as defined for the compounds of formula (I) or together with the Nitrogen atom to which it is attached form the heterocycles $Het^1$ or $Het^2$ as defined for the compounds of formula (I).

iii) deprotection and ring closure of the intermediates of formulas VII or VIII finally provides the compounds of the present invention. The deprotection reaction is usually done using TFA under art known conditions, for example in TFA/DCM/TIS (49:49:2) optionally using trimethylsilyl triflate (TMSOTf), for example 1M TMSOTf/1,5M 2,6-lutidine in DCM. The final ring closure or macrolactamization reaction is done using art known conditions, such as for example by slow addition of the open precursor to a reaction mixture comprising the peptide coupling reagent O-Benzotriazole-N,N,N',N'-tetramethyl-uronium-hexafluoro-phosphate (HBTU) and stirring said reaction mixture for at least 1 hour at room temperature.

Scheme 3

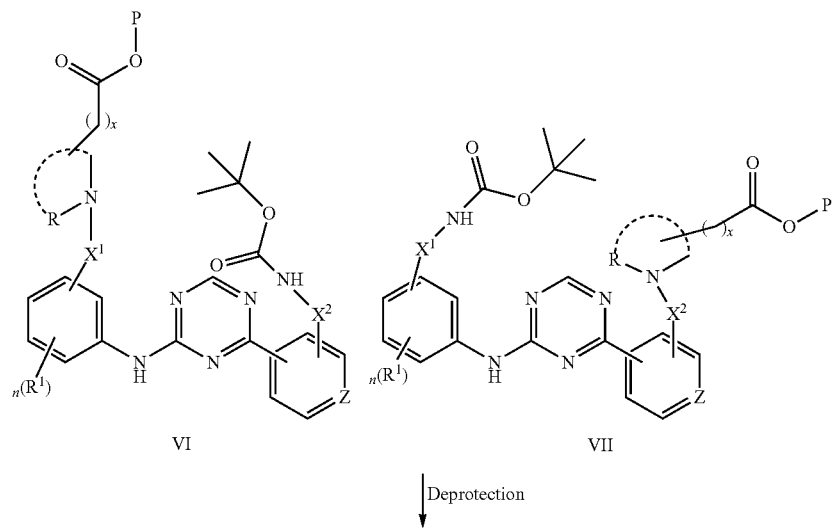

VI VII

Deprotection

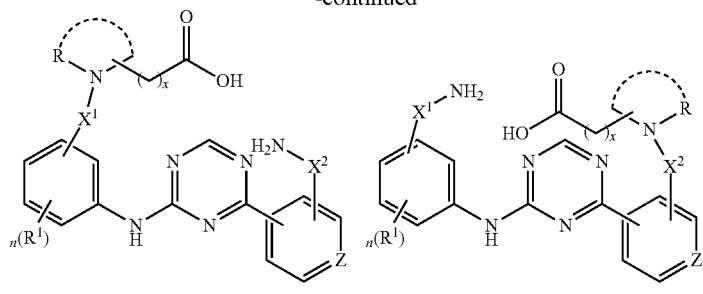

VII    IX

↓ macrolactamization

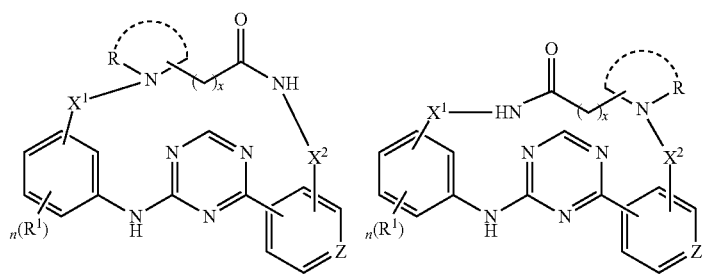

I$^a$    I$^b$ wherein n, Z, $X^1$, $X^2$ and $R^1$ are defined as for the compounds of formula (I) hereinbefore, and wherein x represents 0, 1, 2 or 3; P represents a protective group such as for example methylcarbonyl, t-butyl, methyl, ethyl, benzyl or trialkylsilyl groups; R represents $R^2$ as defined for the compounds of formula (I) or together with the Nitrogen atom to which it is attached form the heterocycles Het$^1$ or Het$^2$ as defined for the compounds of formula (I).

The aniline-triazines as used herein are prepared;

for those compounds where Z represents N and the triazine ring is attached to the Z comprising ring at position 4' and the $X^2$ substituent at position 2' of the structure of formula (I), from the previously described 2-chloro-4-(2-chloro-4-pyridinyl)1,3,5-triazine[333737-06-7] and for other compounds where Z represents N and the triazine ring is attached to the Z comprising ring at position 4' and the $X^2$ substituent at position 2' of the structure of formula (I), from 4-(4-chloro-[1,3,5]triazin-2-yl)-pyridine-2-carboxylic acid methyl ester that is obtained from the commercially available 4-cyano-pyridine-2-carboxylic acid methyl ester as provided in example A18 hereinafter and for those compounds where Z represents N and the triazine ring is attached to the Z comprising ring at position 3' and the $X^2$ substituent is at position 2' of the structure of formula (I), from the previously described 2-chloro-4-(2-chloro-pyridin-3-yl)-[1,3,5]triazine[333736-95-1] and for those compounds where Z represents N and the triazine ring is attached to the Z comprising ring at position 5' and the $X^2$ substituent is at position 3' of the structure of formula (I), from 2-(5-bromo-pyridin-3-yl)-4-chloro-[1,3,5]triazine that is obtained from the commercially available 5-bromonicotinonitrile as provided in example A26 hereinafter and for those compounds where Z represents C, $X^2$ represents $C_{1-4}$alkyl-, and the triazine ring is attached to the Z comprising ring at position 4' and the $X^2$ substituent is at position 2' of the structure of formula (I), from 2-chloro-4-(2-bromophenyl)1,3,5-triazine or 2-(3-bromo-4-fluoro-phenyl)-4-chloro-[1,3,5]triazine that is obtained from the commercially available 3-bromobenzonitrile or 3-bromo-4-fluorobenzonitrile as provided respectively in example A9 or A22 hereinafter and for those compounds where Z represents C, $X^2$ represents $C_{1-4}$alkyl-NH— with NH directly bound to the triazine ring, and the triazine ring is attached to the Z comprising ring at position 4' and the $X^2$ is at position 2' of the structure of formula (I), from 2-chloro-4-(3-nitro-phenyl)-[1,3,5]triazine that is obtained from the commercially available 1-cyano-3-nitrobenzene as provided respectively in example A12 hereinafter and for those compounds where Z represents C, $X^2$ represents $C_{1-4}$alkyloxy- with O directly bound to the triazine ring, and the triazine ring is attached to the Z comprising ring at position 4' and the $X^2$ is at position 1' of the structure of formula (I), from {2-[4-(4-Chloro-[1,3,5]triazin-2-yl)-phenoxy]-ethyl}-carbamic acid tert-butyl ester that is obtained from the commercially available 4-hydroxybenzonitrile as provided respectively in example A16 hereinafter and by introducing the appropriate aniline of general formula (X) to the highly reactive chloro on the triazine under art known conditions, for example by stirring in $CHCl_3$ in the presence of 2 eq. DIPEA, yielding the anilino-aryltriazines of formula (3)

Scheme 4

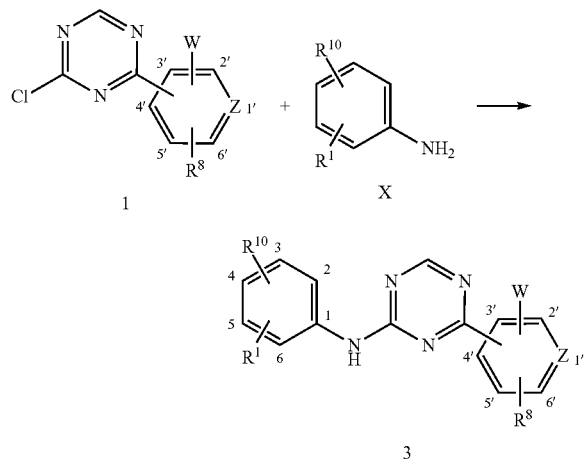

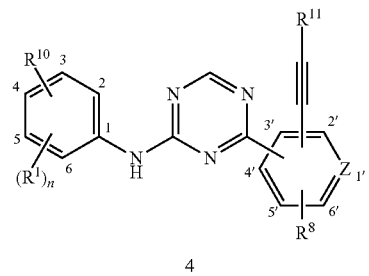

| Intermediate | R10 | triazine attached to | Z | W | R1 | R8 |
|---|---|---|---|---|---|---|
| 3a | 3-CH2OH | 4' | N | 2'-Cl | H | H |
| 3b | 3-CH2OH | 4' | N | 2'-Cl | 5-Cl | H |
| 3c | 3-CH2NHBoc | 4' | N | 2'-Cl | H | H |
| 3d | 3-(CH2)2NHBoc | 4' | N | 2'-Cl | H | H |
| 3e | 3-CH2OH | 4' | C | 2'-Br | H | H |
| 3f | 3-CH2OH | 4' | C | 2'-NO2 | H | H |
| 3g | 3-CH2OH | 4' | C | 1'-O(CH2)2NHBoc | H | H |
| 3h | 3-OCH2CO2tBu | 4' | N | 2'-Cl | H | H |
| 3i | 3-O(CH2)2NHBoc | 4' | N | 2'-CO2Me | H | H |
| 3j | 3-CH2OH | 3' | N | 2'-Cl | H | H |
| 3k | 3-CH2OH | 4' | C | 2'-Br | H | 1'-F |
| 3l | 3-CH2NHBoc | 4' | C | 2'-Br | H | 1'-F |
| 3m | 3-CH2OH | 4' | C | 2'-Br | 5-Cl | 1'-F |
| 3n | 2-CH2NHBoc | 4' | C | 2'-Br | H | H |
| 3o | 3-CH2OH | 5' | N | 3'-Br | H | H |

Boc as used herein corresponds with t-butyloxycarbonyl-; tBu as used herein corresponds with t-Butyl For compounds 3 where W is a halogen, the Sonogashira reaction was used for the synthesis of intermediates of formula II or III where $X_2$ is a $C_{3-4}$alkyl. The Sonogashira reaction consists of the palladium-catalysed coupling of the appropriate alkynyl to the aryl-halogenides to yield the alkynylarenes of formula (4). This reaction is performed under art known conditions such as for example by heating the appropriate alkynyl in the presence of $Pd(PPh_3)_2Cl_2$, $PPh_3$, CuI and $Et_2NH$ at 60° C. for 24 hours under $N_2$ atmosphere.

Particular intermediates made accordingly are summarized in Table 2 below.

TABLE 2

| Intermediate | From | R10 | triazine attached to | Z | R1 | R8 | R11 |
|---|---|---|---|---|---|---|---|
| 4a | 3a | 3-CH2OH | 4' | N | H | H | CH2NHBoc |
| 4b | 3a | 3-CH2OH | 4' | N | H | H | CH2NMeBoc |
| 4c | 3a | 3-CH2OH | 4' | N | H | H | (CH2)2NHBoc |
| 4d | 3b | 3-CH2OH | 4' | N | 5-Cl | H | CH2NHBoc |
| 4e | 3c | 3-CH2NHBoc | 4' | N | H | H | CH2OH |
| 4f | 3d | 3-(CH2)2NHBoc | 4' | N | H | H | CH2OH |
| 4g | 3e | 3-CH2OH | 4' | C | H | H | CH2NHBoc |
| 4h | 3h | 3-OCH2CO2tBu | 4' | N | H | H | CH2NHBoc |
| 4i | 3k | 3-CH2OH | 4' | C | H | 1'-F | CH2NHBoc |
| 4j | 3l | 3-CH2NHBoc | 4' | C | H | 1'-F | CH2OH |
| 4k | 3m | 3-CH2OH | 4' | C | 5-Cl | 1'-F | CH2NHBoc |
| 4l | 3n | 2-CH2NHBoc | 4' | C | 2'-Br | H | CH2OH |
| 4m | 3o | 3-CH2OH | 5' | N | 3'-Br | H | CH2NHBoc |

For those compounds where $X^2$ is further limited to $C_{3-4}$alkyl, the thus obtained compounds of general formula (4) were reduced under art known conditions typically using hydrogenolysis with 10% Pd/C or 5% Pt/C as catalyst in an alkaline solvent such as MeOH/NEt3 or THF/NEt3 to compounds of general formula (5).

Scheme 5

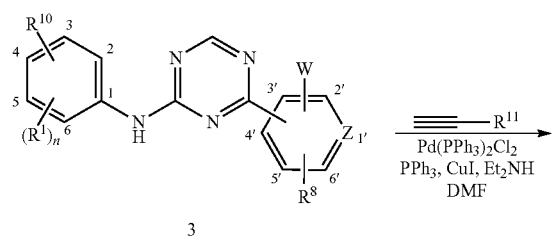

Scheme 6

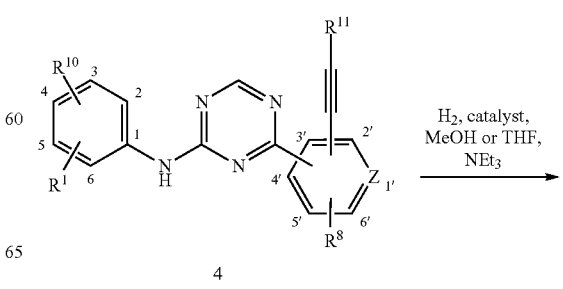

-continued

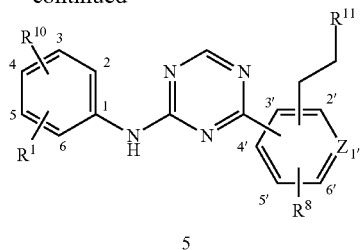

5

Particular intermediates made accordingly are summarized in Table 3.

TABLE 3

| Intermediate | From | R¹⁰ | triazine attached to | Z | R¹ | R⁸ | R¹¹ |
|---|---|---|---|---|---|---|---|
| 5a | 4a | 3-CH₂OH | 4' | N | H | H | CH₂NHBoc |
| 5b | 4b | 3-CH₂OH | 4' | N | H | H | CH₂NMeBoc |
| 5b | 4c | 3-CH₂OH | 4' | N | H | H | (CH₂)₂NHBoc |
| 5c | 4d | 3-CH₂OH | 4' | N | 5-Cl | H | CH₂NHBoc |
| 5f | 4g | 3-CH₂OH | 4' | C | H | H | CH₂NHBoc |
| 5h | 4i | 3-CH₂OH | 4' | C | H | 1'-F | CH₂NHBoc |
| 5i | 4j | 3-CH₂NHBoc | 4' | C | H | 1'-F | CH₂OH |
| 5j | 4k | 3-CH₂OH | 4' | C | 5-Cl | 1'-F | CH₂NHBoc |
| 5k | 4l | 2-CH₂NHBoc | 4' | C | H | H | CH₂OH |
| 5l | 4m | 3-CH₂OH | 5' | N | H | H | CH₂NHBoc |

The amine substitution for those compounds of formula II where the triazine ring is attached to the Z comprising ring at position 4' and $X^2$ is —$C_{1-4}$alkyl-$NR^7$ at position 2' can for example be obtained by stirring the 2-chloropyridyl (3a) in an appropriate amine (6a) as solvent under reflux conditions, such as for 1 hour to overnight at 100-180° C., more specific reaction conditions are provided in the examples hereinafter.

Scheme 7

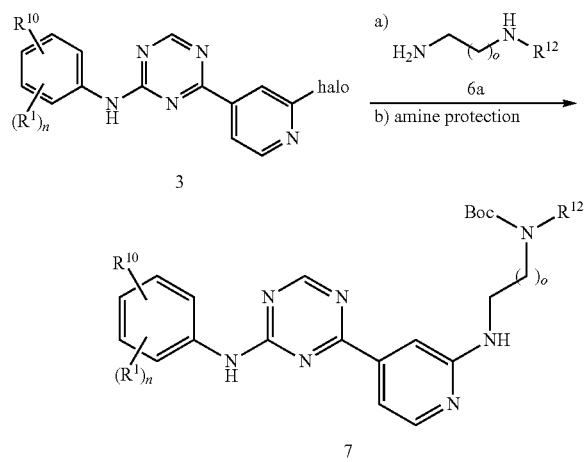

Scheme 7.
a) $R^{12}$—HN(CH₂)ₙCH₂NH₂
(solv.), reflux, overnight (o = 1) or 160° C., 1 h (o = 2)
b) Boc₂O, DCM/MeOH, 4 h.
wherein o is 0, 1, 2, or 3; wherein R¹ and R¹⁰ are defined as for the intermediates of formula (X) hereinbefore, and where R¹² corresponds to R⁴, R⁵ or R⁶ as defined for the compounds of formula (I) hereinbefore.

Similarly, compounds of formula II where the triazine ring is attached to the Z comprising ring at position 3' and $X^2$ is $C_{1-4}$alkyl-$NR^7$ at position 2' can for example be obtained by stirring the 2-chloropyridyl (3k) in an appropriate amine (6b) as solvent under microwave irradiation conditions, such as for 1-3 hour to overnight at 100-140° C., more specific reaction conditions are provided in the examples hereinafter.

Scheme 8

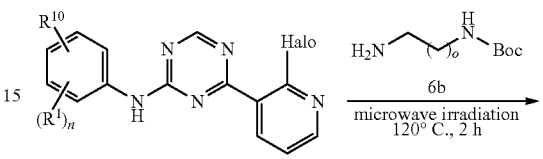

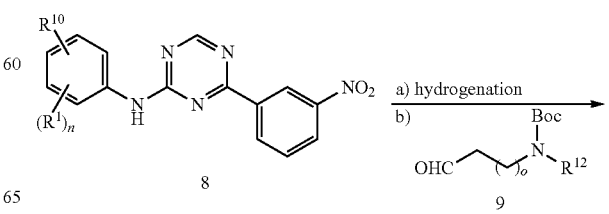

Scheme 8.
wherein o is 0, 1, 2, or 3; wherein R¹ and R¹⁰ are defined as for the intermediates of formula (X) hereinbefore, and where R¹² corresponds to R⁴, R⁵ or R⁶ as defined for the compounds of formula (I) hereinbefore.

Alternatively, for those compounds of formula (I) where Z represents C and $X^2$ is —$C_{1-4}$alkyl-$NR^7$, the aniline-triazine derivatives (10) are prepared from the nitro-derivatives (8) after hydrogenation under art known conditions, for example using hydrogenolysis with 10% Pd/C or 5% Pt/C as catalyst in an alkaline solvent such as MeOH/NEt₃ or THF/NEt₃, and a reductive alkylation using the appropriate aldehyde (9) under art known conditions, for example using NaBH₄ and titanium (iv)isopropoxide as reducing agents in ethanol or 1,2-dichloroethane as solvent.

Scheme 8

-continued

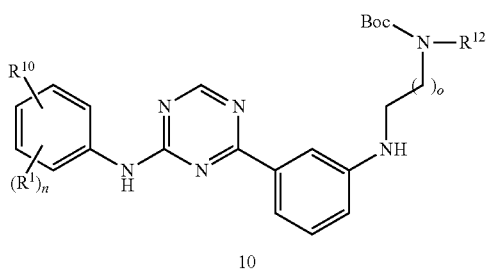

10

Scheme 8.
a) $H_2$, catalyst, MeOH or THF, $NEt_3$
b) $NaBH_4$, titanium(iv)isopropoxide/1,2-dichloroethane 3,5 h.
wherein o is 0, 1, 2, or 3; wherein $R^1$ and $R^{10}$ are defined as for the intermediates of formula (X) hereinafter and wherein $R^{12}$ corresponds to $R^4$, $R^5$ or $R^6$ as defined for the compounds of formula (I) hereinbefore.

Particular intermediates made according to scheme 8 are provided in the examples A14 and A15 hereinafter.

Compounds of formula II where $X^2$ is limited to $C_2$alkyl were prepared by Stille reaction of 3a to compound 11, followed by Michael type addition of a suitable amine, for instance a mono-Bocprotected diamine to form 12, as shown in scheme 9 and exemplified under A19 hereinafter.

Scheme 9

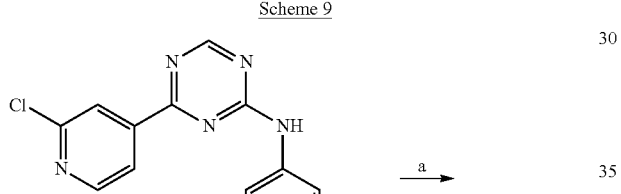

3a

-continued

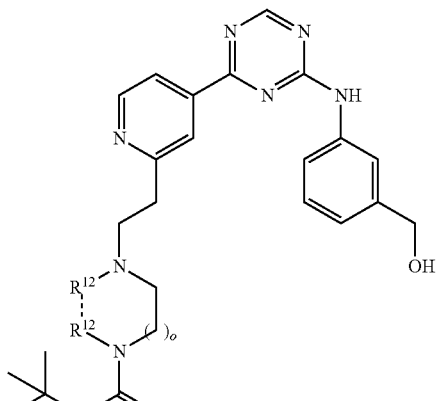

12

Scheme 9.
a) $(n-Bu)_3SnCH=CH_2$, $Pd(PPh_3)_4$, $PPh_3$, DMF, 80° C., 48 h
b) N-Boc-protected diamine (melt), 70-100° C.;
wherein both $R^{12}$ independently correspond to $R^4$, $R^5$ or $R^6$, with a possible interconnection when $R^{12}$ is methyl and o = 1, 2 as defined for the compounds of formula (I) hereinbefore.

Compounds of formula II where $X^2$ is limited to methylene were prepared via cyanation on compound 3a under art known conditions, such as heating to 80° C. in the presence of $Pd_2(dba)_3$, dppf, Zn and $Zn(CN)_2$ for 2 h, followed by reduction of the nitrile under art known conditions such as hydrogenation in the presence of Raney nickel catalyst and subsequent protection with a Boc-group providing 14, as shown in scheme 10 and exemplified under A30 hereinafter.

Scheme 10

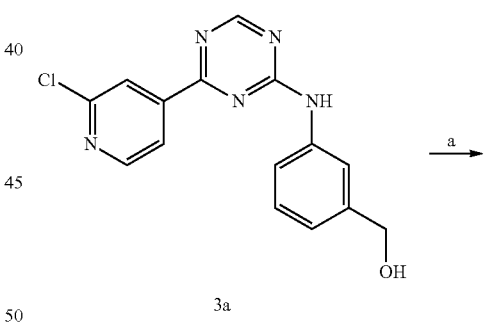

3a

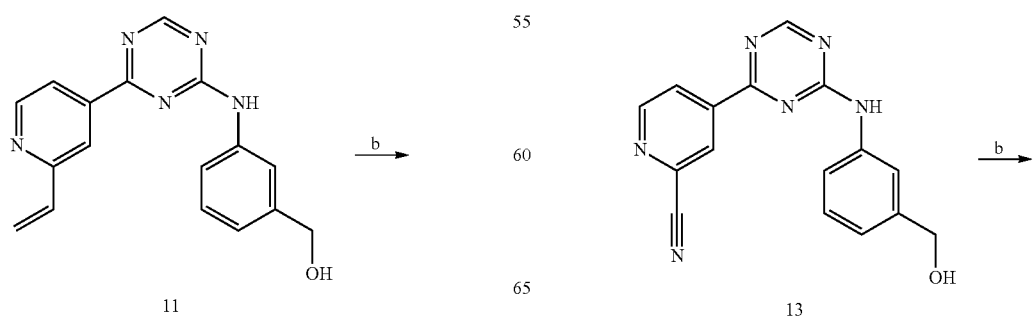

11                                         13

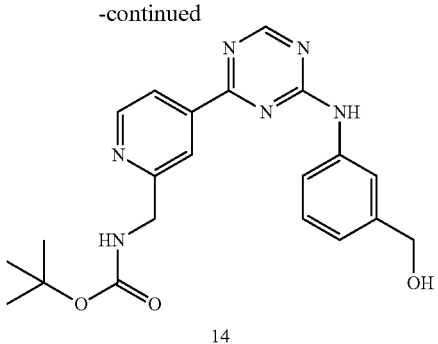

Scheme 10.
a) Pd$_2$(dba)$_3$, dppf, Zn, Zn(CN)$_2$, DMA, 80° C., 2 h;
b) (i) RaNi, MeOH/NH$_3$, H$_2$, RT, (ii) (Boc)$_2$O, CH$_2$Cl$_2$, MeOH, Na$_2$CO$_3$ 10%, r.t., 1 h.

Compounds of formula III where X$^2$ is limited to methylene were prepared via reduction of compound 3i to the corresponding alcohol 15, as shown in scheme 11 and exemplified under A18 hereinafter.

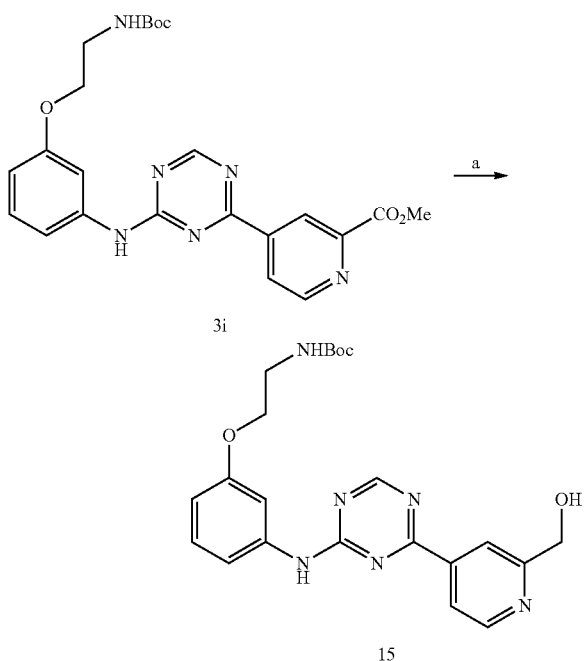

Scheme 11.
a) NaBH$_4$, CaCl$_2$, MeOH, -15 to -10° C.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include C$_{(1-6)}$ alkyl or benzyl esters.

The protection and deprotection of functional groups may take place before or after a reaction step. The use of protecting groups is fully described in 'Protective Groups in Organic Synthesis' 3$^{rd}$ edition, T W Greene & P G M Wutz, Wiley Interscience (1999).

Additionally, the N-atoms in compounds of formula (I) can be methylated by art-known methods using CH$_3$—I in a suitable solvent such as, for example 2-propanone, tetrahydrofuran or dimethylformamide.

The compounds of formula (I) can also be converted into each other following art-known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydro-carbons, e.g. toluene, ketones, e.g. 2-butanone, halogenated hydrocarbons, e.g. dichloromethane, and mixtures of such solvents.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures. However, in the synthesis of the compounds of formula (I), the present invention further provides;

a) the intermediates of formula (X)

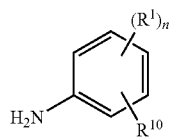

the pharmaceutically acceptable addition salts and the stereochemically isomeric forms thereof, wherein n represents an integer from 1 to 4;

$R^1$ represents hydrogen, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl)amino-sulfonyl, $C_{1-6}$alkoxy-substituted with halo or $R^1$ represents $C_{1-6}$alkyl substituted with one or where possible two or more substituents selected from hydroxy or halo;

$R^{10}$ represents hydrogen, cyano, halo, hydroxy, $C_{1-6}$alkoxy-, $C_{1-6}$alkyl-, or $C_{1-6}$alkyl substituted with one or where possible two or more residues selected from hydroxy and $NR^{13}R^{14}$;

$R^{13}$ and $R^{14}$ each independently represent hydrogen, $C_{1-6}$alkyl, $C_{1-6}$alkyloxycarbonyl, or $C_{1-6}$alkyloxycarbonyl$C_{1-4}$alkyl-.

In particular the intermediates of formula (X) wherein one or more of the following restrictions apply;

i) n represents 1;

ii) $R^1$ represents hydrogen or halo, in particular hydrogen or chloro;

iii) $R^{10}$ represents $C_{1-6}$alkyl substituted with one or where possible two or more residues selected from hydroxy and $NR^{13}R^{14}$;

iv) $R^{13}$ and $R^{14}$ each independently represent hydrogen, $C_{1-6}$alkyl, $C_{1-6}$alkyloxycarbonyl, or $C_{1-6}$alkyloxycarbonyl$C_{1-4}$alkyl-.

b) the intermediates of formula (XI)

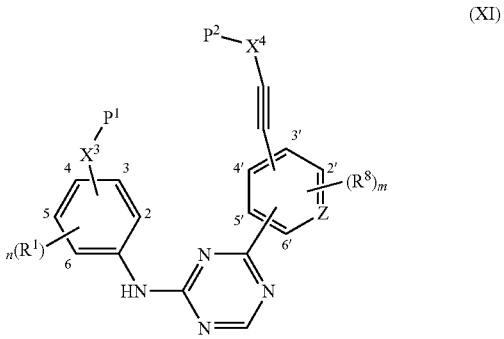

the pharmaceutically acceptable addition salts and the stereochemically isomeric forms thereof, wherein n represents an integer from 1 to 4; m represents an integer from 1 to 4;

Z represents N or C;

$P_1$ and $P_2$ each independently represent hydroxy, halo, hydroxycarbonyl-, halocarbonyl-, $C_{1-6}$alkyloxycarbonyl- or $C_{1-6}$alkyloxycarbonyl-$C_{1-4}$alkyl-;

$X^3$ represents $C_{1-6}$alkyl or $C_{1-6}$alkyl-$NR^{20}$;

$X^4$ represents $C_{1-6}$alkyl or $C_{1-6}$alkyl-$NR^{21}$;

$R^1$ and $R^8$ each independently represent hydrogen, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl)amino-sulfonyl, $C_{1-6}$alkoxy-substituted with halo or $R^1$ represents $C_{1-6}$alkyl substituted with one or where possible two or more substituents selected from hydroxy or halo;

$R^{20}$ and $R^{21}$ each independently represent hydrogen, $C_{1-4}$alkyl, $Het^{20}$, $Het^{21}$-$C_{1-4}$alkyl-, optionally substituted with $Het^{22}$-$C_{1-4}$alkylaminocarbonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$Het^{20}$ represents a heterocycle selected from pyrrolidinyl, or piperidinyl wherein said $Het^{20}$ is optionally substituted with $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{21}$ represents a heterocycle selected from pyrrolidinyl or piperidinyl wherein said $Het^{21}$ is optionally substituted with $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{22}$ represent a heterocycle selected from morpholinyl, pyrrolidinyl, piperazinyl, or piperidinyl wherein said $Het^{22}$ is optionally substituted with $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-.

In another embodiment the present invention provides the intermediates of formula (XI) wherein one or more of the following restrictions apply;

n represents 1; m represents 1; Z represents N or C, in particular N;

$P_1$ and $P_2$ each independently represent hydroxy, $C_{1-6}$alkyloxycarbonyl or $C_{1-6}$alkyloxycarbonyl-$C_{1-4}$alkyl-;

$X^3$ represents —$C_{1-4}$alkyl- or $C_{1-4}$alkyl-$NR^{20}$—;

$X^4$ represents —$C_{1-4}$alkyl- or $C_{1-4}$alkyl-$NR^{21}$—;

$R^1$ represents hydrogen, polyhalo$C_{1-4}$alkyl or halo; in particular hydrogen, trifluoromethyl, fluoro, chloro or iodo;

$R^8$ represents hydrogen, polyhalo$C_{1-4}$alkyl or halo; more in particular hydrogen;

$R^{20}$ and $R^{21}$ each independently represent hydrogen or $C_{1-4}$alkyl.

Other groups of special intermediates are:
- those intermediates of formula (XI) wherein Z represents N
- those intermediates of formula (XI) wherein $X^3$ represents methyl, ethyl-$NR^{20}$ or methyl-$NR^{20}$;
- those intermediates of formula (XI) wherein $X^4$ represents methyl, ethyl-$NR^{21}$ or methyl-$NR^{21}$;
- those intermediates of formula (XI) wherein $P^1$ represents hydroxy, $C_{1-6}$alkyloxycarbonyl or $C_{1-6}$alkyloxycarbonyl-$C_{1-4}$alkyl-, in particular hydroxy, t-butyloxycarbonyl, t-butyloxycarbonyl-methyl-;
- those intermediates of formula (XI) wherein $P^2$ represents hydroxy, $C_{1-6}$ alkyloxycarbonyl or $C_{1-6}$ alkyloxycarbonyl-$C_{1-4}$ alkyl-, in particular hydroxy, t-butyloxycarbonyl, t-butyloxycarbonyl-methyl-;
- those intermediates of formula (XI) wherein $R^{20}$ represents hydrogen or methyl;
- those intermediates of formula (XI) wherein $R^{21}$ represents hydrogen or methyl;
- those intermediates of formula (XI) wherein $R^1$ represents hydrogen, chloro, fluoro or bromo;
- those intermediates of formula (XI) wherein $R^8$ represents hydrogen.

Of particular interest are those intermediates of formula (XI) wherein the $X^3$ substituent is at position 3, the $R^1$ substituent represents hydrogen or halo and is at position 5, the triazine ring is attached to the Z comprising ring at position 4' and the alkynyl is at position 2' of the intermediate of formula (XI). For those intermediates of formula (XI) wherein Z represents C, the $R^8$ substituent is at position 1', the $X^3$ substituent is at position 3, the $R^1$ substituent represents hydrogen or halo and is at position 5, the triazine ring is attached to the Z comprising ring at position 4' and the alkynyl is at position 2' of the intermediate of formula (XI).

The intermediates of formula (XI) were found to have GSK-3 inhibitory effects and are accordingly provided for use as a medicine, in particular in the prevention or treatment of diseases mediated through GSK-3 activity supra.

It is also an object of the present invention to provide the use of the intermediates of formula (X), (XI) in the synthesis of a macrocyclic kinase inhibitor such as for the compounds of formula (I).

As described in the experimental part hereinafter, the kinase inhibitory effect and the GSK-3 inhibitory effect of the present compounds has been demonstrated in vitro, in phosphorylation assays using an appropriate peptide substrate and radiolabeled ATP as provided in more detail in example C1 & C3 hereinafter. In addition to the enzymatic assays, the cellular activity of the present compounds was demonstrated in an assay based on the capability of GSK-3 in inactivating glycogen synthase in liver cells. In this assay, example C2 hereinafter, the compounds of the present invention were shown to increase $^{14}$C-D glucose incorporation into glycogen of Chang cells.

Accordingly, the present invention provides the compounds of formula (I), the intermediates of formula (VI) and their pharmaceutically acceptable N-oxides, addition salts, quaternary amines and stereochemically isomeric forms for use in therapy. More particular in the treatment or prevention of serine/tyrosine kinase mediated diseases. The compounds of formula (I), the intermediates of formula (VI) and their pharmaceutically acceptable N-oxides, addition salts, quaternary amines and the stereochemically isomeric forms may hereinafter be referred to as compounds according to the invention.

Disorders for which the compounds according to the invention are particularly useful are cell proliferative disorders supra, diabetic complications, Alzheimer's disease, autoimmune diseases and inflammatory diseases including allergies and asthma, multiple sclerosis (MS), rheumatoid arthritis (RA), arteriosclerosis, arthritis or Inflammatory Bowel Disease (IBD).

In view of the utility of the compounds according to the invention, there is provided a method of treating a cell proliferative, diabetic complications, Alzheimer's disease, autoimmune diseases and inflammatory diseases including allergies and asthma, multiple sclerosis (MS), rheumatoid arthritis (RA), arteriosclerosis, arthritis or Inflammatory Bowel Disease (IBD), the method comprising administering to an animal in need of such treatment, for example, a mammal including humans, a therapeutically effective amount of a compound according to the present invention.

Said method comprising the systemic or topical administration of an effective amount of a compound according to the invention, to animals, including humans. One skilled in the art will recognize that a therapeutically effective amount of the kinase inhibitors of the present invention is the amount sufficient to induce the kinase inhibitory effect and that this amount varies inter alia, depending on the concentration of the compound in the therapeutic formulation, and the condition of the patient. Generally, an amount of kinase inhibitor to be administered as a therapeutic agent for treating cell proliferative disorder such as atheriosclerosis, restenosis and cancer, will be determined on a case by case by an attending physician.

Generally, a suitable dose is one that results in a concentration of the kinase inhibitor at the treatment site in the range of 0.5 nM to 200 µM, and more usually 5 nM to 10 µM. To obtain these concentrations, a patient in need of treatment likely will be administered between 0.01 mg/kg to 500 mg/kg body weight, in particular from 10 mg/kg to 250 mg/kg body weight. As noted above, the above amounts may vary on a case-by-case basis. In these methods of treatment the compounds according to the invention are preferably formulated prior to admission. As described herein below, suitable pharmaceutical formulations are prepared by known procedures using well known and readily available ingredients.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.01 mg/kg to 500 mg/kg body weight, in particular from 10 mg/kg to 250 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18th ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

EXPERIMENTAL PART

Hereinafter, the term 'P' means product, 'MP-NCO' means macroporous isocyanate resin, 'DIPEA' means N-ethyl-N-(1-methylethyl)-2-propanamine, 'DMF' means N,N-dimethylformamide, 'CH$_2$Cl$_2$' means dichloromethane, 'CH$_3$CN' means acetonitrile, 'TIS' means tris(1-methylethyl)silane, 'TFA' means trifluoroacetic acid, 'Et$_3$N' means triethylamine, 'EtOAc' means ethyl acetate, 'HBTU' means 1-[bis(dimethylamino)methylene]-1H-benzotriazoliumhexafluorophosphate(1-)3-oxide, 'MeOH' means methanol, 'MgSO$_4$' means magnesium sulphate, 'DIPE' means diisopropyl ether, 'NaBH$_4$' means sodium tetrahydroborate(–1), 'Cs$_2$CO$_3$' means cesium carbonate, 'NaOCH$_3$' means methanol, sodium salt, 'H$_2$N—CN' means methanediimine, 'CaCl$_2$' means calcium chloride, 'Pd(OAc)$_2$' means acetic acid palladium(2+) salt, 'NaHCO$_3$' means carbonic acid monosodium salt, 'Na$_2$CO$_3$' means carbonic acid disodium salt 'NaCl' means sodium chloride.

A. PREPARATION OF THE INTERMEDIATES

Example A1 a) Preparation of Intermediate 1

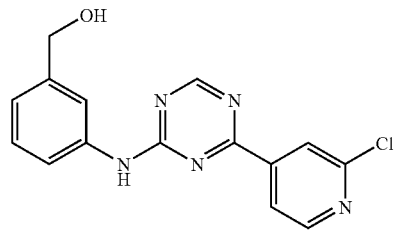 [SMILES: OCc1cccc(Nc2ncnc(-c3ccnc(Cl)c3)n2)c1]

A solution of 2-chloro-4-(2-chloro-4-pyridinyl)-1,3,5-triazine (0.02 mol) and 3-amino-benzenemethanol (0.02 mol) in trichloromethane (100 ml) was stirred at room temperature. DIPEA (0.04 mol) was added and the resultant reaction mixture was stirred for 5 hours at 60° C. (yellow precipitation resulted). DIPEA (100 ml) was added and the reaction mixture was stirred for one hour at room temperature. The precipitate was filtered off, washed with DIPEA, then with hexane, then dried (vacuum, 65° C.), yielding 4.77 g (76%; M.P.: 157.4-159.6° C.) of intermediate 1.

b) Preparation of Intermediate 2

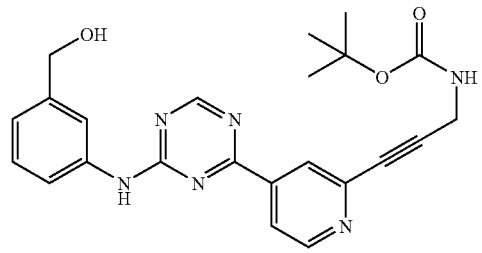 [SMILES: CC(C)(C)OC(=O)NCC#Cc1cc(-c2ncnc(Nc3cccc(CO)c3)n2)ccn1]

To a mixture of intermediate 1 (0.001 mol), 1,1-dimethylethyl ester 2-propynyl carbamic acid (0.0011 mol), N-ethylethanamine (1.5 ml), dichlorobis(triphenylphosphine)palladium (0.00005 mol), copper(I) iodide (0.00005 mol) and triphenylphosphine (0.0002 mol) in a tube, DMF (10 ml) was added. N$_2$ gas was bubbled through the mixture for 5 minutes. The tube was sealed and the mixture was stirred at 60° C. for 24 hours under N$_2$ atmosphere. Upon cooling, water and CH$_2$Cl$_2$ were added. The organic layer was separated, dried and concentrated. The residue was purified by short pad column chromatography over silica gel (eluent: CH$_2$Cl$_2$/MeOH 100/0 to 95/5). The product fractions were collected and the solvent was evaporated. The residue was crystallized from CH₃CN/MeOH. The precipitate was filtered off and dried, yielding 0.3554 g (82%; M.P.: 154.4-156.2° C.) of intermediate 2.

c) Preparation of Intermediate 3

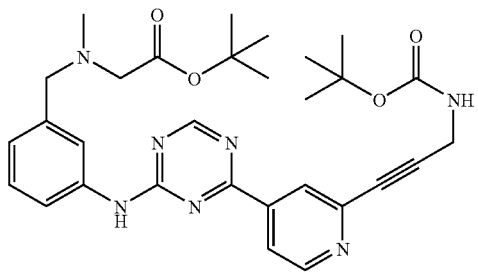 [SMILES: CN(CC(=O)OC(C)(C)C)Cc1cccc(Nc2ncnc(-c3ccnc(C#CCNC(=O)OC(C)(C)C)c3)n2)c1]

To a stirred suspension of intermediate 2 (0.00075 mol) in dry CH₃CN (10 ml), methanesulfonyl chloride (0.0009 mol) and DIPEA (0.0045 mol) were added. An extra amount of methanesulfonyl chloride (0.0002 mol) was added to effect complete mesylation. After 5 minutes, N-methylglycine 1,1-dimethylethyl ester hydrochloride (0.0015 mol) was added and the mixture was stirred at 65° C. for 3.5 hours. 1-Ethenyl-4-(isocyanatomethyl)benzene, polymer with ethenylbenzene (0.0015 mol) and CH₂Cl₂ (10 ml) were added and the reaction mixture was shaken for 5 hours at room temperature. The mixture was filtered, and the filter residue was washed with CH₂Cl₂, then with MeOH and then again with CH₂Cl₂. The filtrate's solvent was evaporated, yielding intermediate 3 (used in next reaction step without further purification).

d) Preparation of Intermediates 4a and 4b

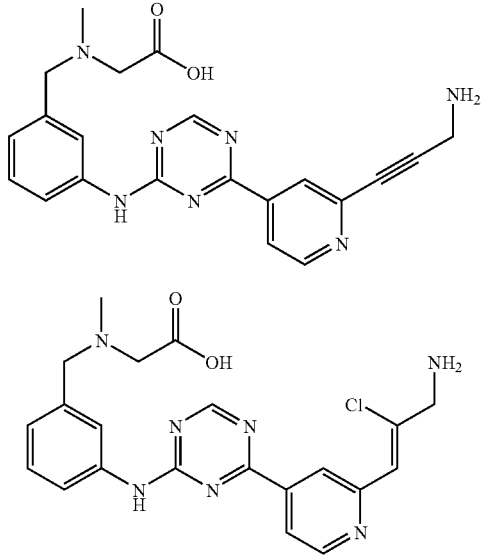

A mixture of intermediate 3 (0.00075 mol) in TFA/CH₂Cl₂/TIS (49/49/2) (15 ml) was stirred overnight at room temperature. The solvent was evaporated, yielding intermediate 4 as a TFA salt (.C₂HF₃O₂) (quantitative; LCMS 4a: 70%, 4b: 30%; used in next reaction step without further purification).

Example A2 a) Preparation of Intermediate 5

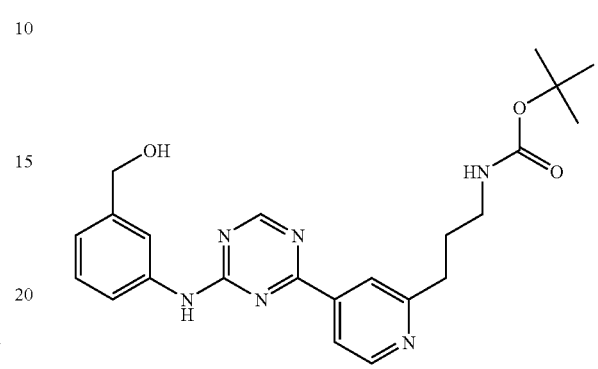

A mixture of intermediate 2 (0.0092 mol) and Et₃N (2 ml) in MeOH (150 ml) was hydrogenated overnight with Pd/C (10%) (1 g) as a catalyst in the presence of a thiophene solution (0.5 ml). After uptake of H₂ (2 equiv), the catalyst was filtered off and the filtrate was evaporated. The residue was redissolved in CH₂Cl₂ and filtered through a pad of silica gel (eluent: CH₂Cl₂/MeOH 100/0, then 94/6). The desired product fractions were collected and the solvent was evaporated, yielding 3.7406 g (93%, yellow solid; M.P.: 161.5-162.3° C.) of intermediate 5.

b) Preparation of Intermediate 6

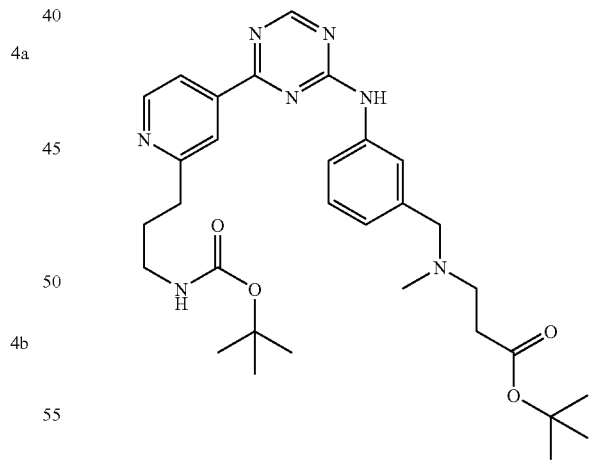

To a stirred solution of intermediate 5 (0.00025 mol) in dry CH₃CN (5 ml) was added DIPEA (6 equiv). Then, methanesulfonyl chloride (1.2 equiv) was added. After 5-15 minutes, N-methyl-β-alanine 1,1-dimethylethyl ester hydrochloric acid salt (1:1) (3 equiv) was added and the resulting solution was stirred overnight at 65° C. Then, the mixture was cooled to room temperature and CH₂Cl₂ (5 ml) was added, followed by MP-NCO (4 equiv). Upon shaking overnight the resin was filtered off and washed with CH₂Cl₂ (5 ml), MeOH (5 ml) and again CH$_2$Cl$_2$ (5 ml). Next, the mixture was concentrated, yielding crude intermediate 6 (used in next reaction step without further purification).

Intermediate 6a was prepared analogously from Intermediate 80 using 1,1-dimethylethyl ester 1-piperazinecarboxylic acid dihydrochloride.

Intermediate 6b was prepared analogously from Intermediate 112 using N-methylglycine 1,1-dimethylethyl ester hydrochloride.

Intermediate 6c was prepared analogously from Intermediate 114 using N-methyl-β-alanine 1,1-dimethylethyl ester hydrochloric acid salt.

c) Preparation of Intermediate 7

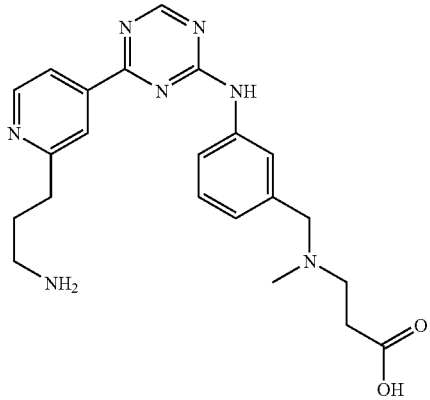 [SMILES: CN(CCC(=O)O)Cc1cccc(Nc2ncnc(-c3ccnc(CCCN)c3)n2)c1]

Intermediate 6 was dissolved in TFA/CH$_2$Cl$_2$/TIS (49/49/2) (5 ml) and shaken for 5 hours at room temperature. Next, the solvent was evaporated, yielding intermediate 7 (TFA salt, used in next reaction step without further purification).

Intermediate 7a was prepared analogously from Intermediate 6a.

Intermediate 7b was prepared analogously from Intermediate 6b.

Intermediate 7c was prepared analogously from Intermediate 6c.

Example A3 a) Preparation of Intermediate 8

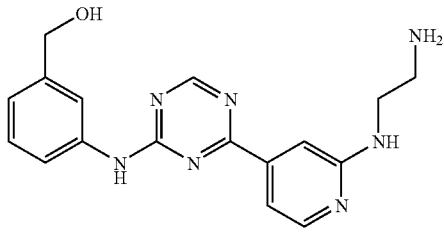 [SMILES: NCCNc1cc(-c2ncnc(Nc3cccc(CO)c3)n2)ccn1]

Intermediate 1 (0.0075 mol) was dissolved in 1,2-ethanediamine (100 ml). The solution was stirred at reflux (117-118° C.) overnight. The solvent was evaporated. Xylene was added to the residue, then co-evaporated again twice, yielding intermediate 8, which was used as such for the next reaction step.

b) Preparation of Intermediates 9 and 10

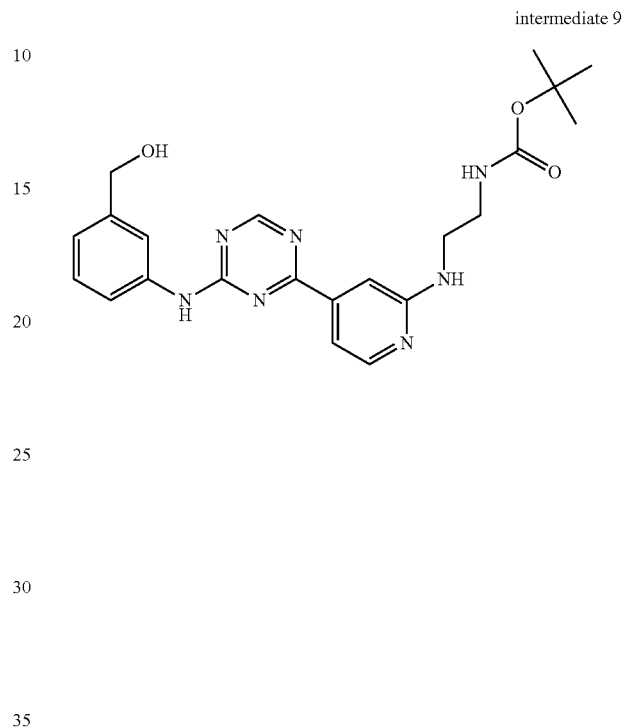

intermediate 9 intermediate 10

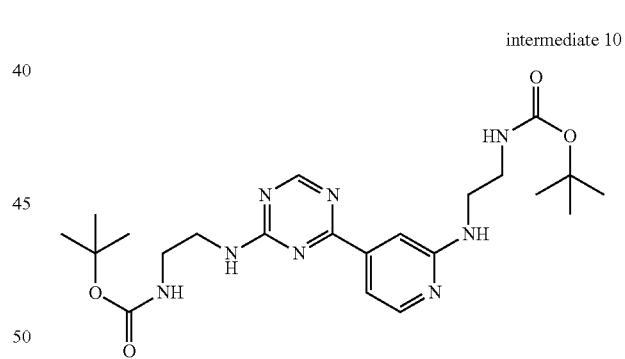

Crude intermediate 8 (0.0075 mol) was dissolved in CH$_2$Cl$_2$ (100 ml). Bis(1,1-dimethylethyl)ester dicarbonic acid (0.01125 mol) was added and the reaction mixture was stirred at room temperature. MeOH (100 ml) was added in order to obtain complete dissolution. The reaction mixture was stirred for one hour at room temperature. More bis(1,1-dimethylethyl)ester dicarbonic acid (0.01125 mol) was added and the reaction mixture was stirred over the weekend at room temperature. 7N NH$_3$/MeOH (100 ml) was added. The solvent was evaporated. The residue was purified over a pad of silica gel on a glass filter (eluent: CH$_2$Cl$_2$/EtOAc 100/0 to 0/100). The desired fractions were collected and the solvent was evaporated. The residue was purified further by reversed-phase high-performance liquid chromatography (ammonium acetate-buffer), yielding 0.62 g of intermediate 9 (19%, M.P. >315° C. (decomp.)) and 0.49 g of intermediate 10 (14%, M.P.: 184.6-184.8° C.).

c) Preparation of Intermediate 11

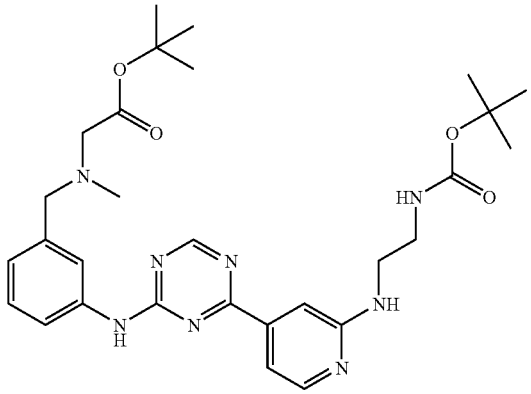 [SMILES: CN(CC(=O)OC(C)(C)C)Cc1cccc(Nc2ncnc(-c3ccnc(NCCNC(=O)OC(C)(C)C)c3)n2)c1]

To a stirred solution of intermediate 9 (0.000125 mol) in DMF (5 ml) was added DIPEA (6 equiv). Then, methanesulfonyl chloride (1.2 equiv.) was added. After 5-15 minutes, N-methylglycine 1,1-dimethylethyl ester hydrochloride (3 equiv) was added and the resulting solution was stirred overnight at 65° C. Then, the mixture was cooled to room temperature and MP-NCO (6 equiv) was added. Upon shaking overnight, the resin was filtered off and washed with DMF (4×5 ml). Next, the mixture was concentrated, yielding crude intermediate 11 (used in next reaction step without further purification).

d) Preparation of Intermediate 12

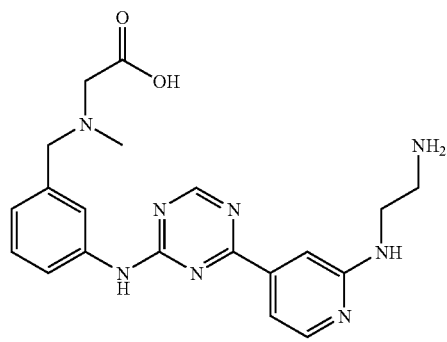 [SMILES: CN(CC(=O)O)Cc1cccc(Nc2ncnc(-c3ccnc(NCCN)c3)n2)c1]

Intermediate 11 (crude compound) was dissolved in TFA/CH$_2$Cl$_2$/TIS (49/49/2) (5 ml) and shaken for 1 hour at 40° C. Next, the solvent was evaporated, yielding crude intermediate 12 (TFA salt, used in next reaction step without further purification).

Example A4 a) Preparation of Intermediate 13

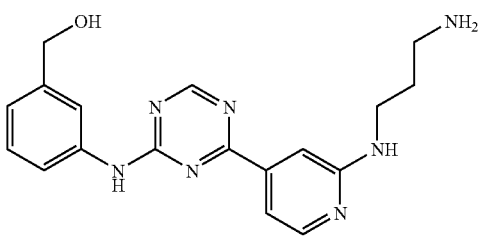 [SMILES: NCCCNc1cc(-c2ncnc(Nc3cccc(CO)c3)n2)ccn1]

Intermediate 1 (0.00768 mol) was dissolved in 1,2-propanediamine (100 ml). The solution was stirred for 2 hours at 160° C., then cooled to room temperature. The solvent was evaporated. Xylene was added to the residue, then co-evaporated again, yielding intermediate 13, which was used as such for the next reaction step.

b) Preparation of Intermediate 14

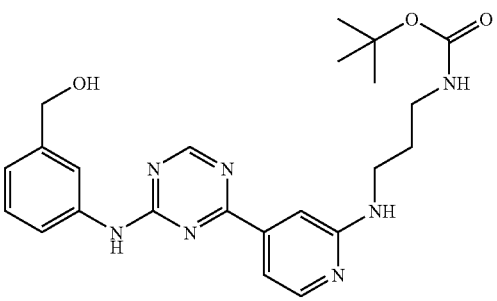 [SMILES: CC(C)(C)OC(=O)NCCCNc1cc(-c2ncnc(Nc3cccc(CO)c3)n2)ccn1]

Bis(1,1-dimethylethyl)ester dicarbonic acid (0.023 mol) was added to intermediate 13 (0.00768 mol), dissolved in CH$_2$Cl$_2$/MeOH (100 ml/100 ml). The reaction mixture was stirred for 3 hours at room temperature. More bis(1,1-dimethylethyl)ester dicarbonic acid (0.023 mol) was added and the reaction mixture was stirred for one hour at room temperature. A precipitate was removed by filtration. The filtrate was purified over a pad of silica gel on a glass filter (eluent: CH$_2$Cl$_2$/EtOAc 100/0 to 0/100). The desired fractions were collected and the solvent was evaporated. The residue was purified further by reversed-phase high-performance liquid chromatography (ammonium acetate buffer). The product precipitated from the aqueous component of the eluent. The precipitate was filtered off, washed with distilled water, and dried, yielding 0.58 g of intermediate 14 (17%; M.P. 183.5-184.5° C.).

c) Preparation of Intermediate 15

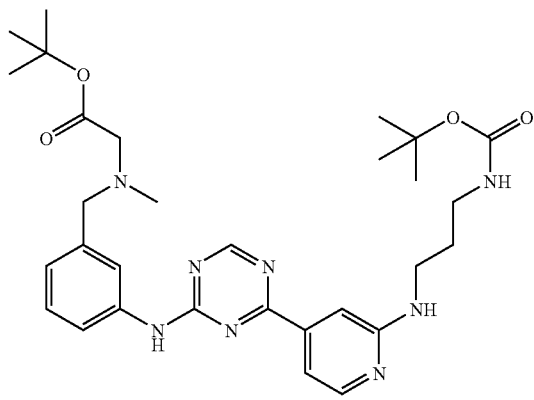 [SMILES: CN(CC(=O)OC(C)(C)C)Cc1cccc(Nc2ncnc(-c3ccnc(NCCCNC(=O)OC(C)(C)C)c3)n2)c1]

To a stirred solution of intermediate 14 (0.000125 mol) in DMF (5 ml) was added DIPEA (6 equiv). Then, methanesulfonyl chloride (1.2 equiv.) was added. After 5-15 minutes, N-methylglycine 1,1-dimethylethyl ester hydrochloride (3 equiv) was added and the resulting solution was stirred overnight at 65° C. Then, the mixture was cooled to room temperature and MP-NCO (6 equiv) was added. Upon shaking overnight, the resin was filtered off and washed with DMF (4×5 ml). Next, the mixture was concentrated, yielding crude intermediate 15 (used in next reaction step without further purification).

d) Preparation of Intermediate 16

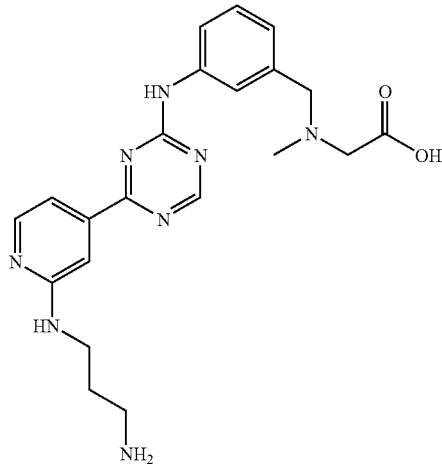 [SMILES: CN(CC(=O)O)Cc1cccc(Nc2ncnc(-c3ccnc(NCCCN)c3)n2)c1]

Intermediate 15 (crude compound) was dissolved in TFA/CH$_2$Cl$_2$/TIS (49/49/2) (5 ml) and shaken for 1 hour at 40° C.

Next, the solvent was evaporated, yielding crude intermediate 16 (TFA salt, used in next reaction step without further purification).

Example A5 a) Preparation of Intermediate 17

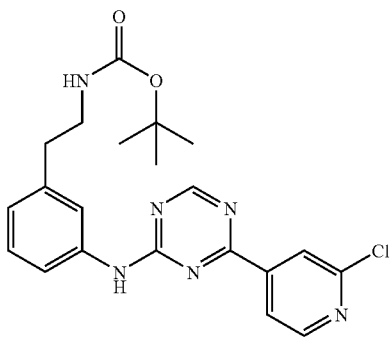 [SMILES: CC(C)(C)OC(=O)NCCc1cccc(Nc2ncnc(-c3ccnc(Cl)c3)n2)c1]

A solution of 2-chloro-4-(2-chloro-4-pyridinyl)-1,3,5-triazine (0.01 mol) and 1,1-dimethylethyl ester[2-(3-aminophenyl)ethyl]carbamic acid (0.01 mol) in trichloromethane (30 ml) was stirred at room temperature. DIPEA (0.02 mol) was added and the resultant reaction mixture was stirred overnight at 60° C. DIPEA (90 ml) was added and the reaction mixture was stirred for 2.5 hours at room temperature. The precipitate was filtered off, washed with hexane, then dried (vacuum, 65° C.), yielding 4.46 g (100%; M.P.: 144.1-147.0° C.) of intermediate 17.

b) Preparation of Intermediate 18

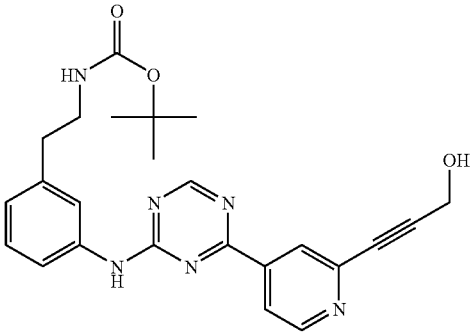 [SMILES: CC(C)(C)OC(=O)NCCc1cccc(Nc2ncnc(-c3ccnc(C#CCO)c3)n2)c1]

A mixture of intermediate 17 (0.0095 mol), N-ethylethanamine (15 ml), dichlorobis(triphenylphosphine)palladium (0.00048 mol), copper(I) iodide (0.00048 mol) and triphenylphosphine (0.00190 mol) in DMF (100 ml) was stirred at room temperature. N$_2$ gas was bubbled through the mixture for 10 minutes. 2-Propyn-1-ol (0.01425 mol) was added and the reaction mixture was stirred at 60° C. (nitrogen atmosphere) for 20 hours under N$_2$ atmosphere. Upon cooling, water (10 ml) was added. The solvent was evaporated, and the residue was redissolved in CH$_2$Cl$_2$. The solution was purified over silica gel (eluent: first CH$_2$Cl$_2$, then EtOAc). The desired product fractions were collected and the solvent was evaporated. The residue was dissolved in CH$_3$CN and kept at 0° C. overnight, resulting in precipitation of brown crystals. The precipitate was filtered off and dried, yielding 2.64 g (62%; M.P.: 155.5-158.0° C.) of intermediate 18.

c) Preparation of Intermediate 19

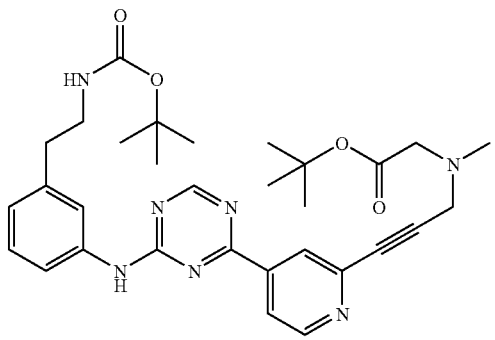 [SMILES: CN(CC#Cc1cc(-c2ncnc(Nc3cccc(CCNC(=O)OC(C)(C)C)c3)n2)ccn1)CC(=O)OC(C)(C)C]

Intermediate 18 (0.00025 mol) was dissolved in DMF (10 ml). DIPEA (0.0015 mol) was added. Methanesulfonyl chloride (0.000375 mol) was added while stirring. N-methylglycine 1,1-dimethylethyl ester hydrochloride (0.00075 mol) was added and the reaction mixture was stirred for 4.5 hours at 65° C. Then, the mixture was cooled to room temperature and MP-NCO (6 equiv) was added. Upon shaking overnight, the resin was filtered off and washed with DMF (4×5 ml). Upon evaporation of the solvent crude intermediate 19 (LCMS: 93% P) was obtained (used in next reaction step without further purification).

d) Preparation of Intermediate 20

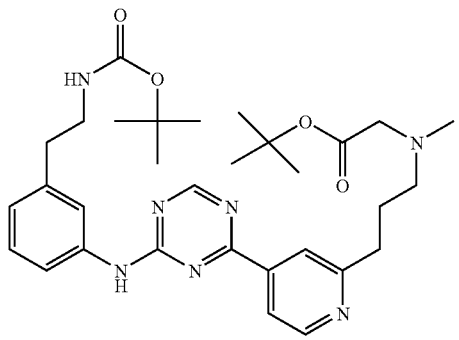 [SMILES: CN(CCCc1cc(-c2ncnc(Nc3cccc(CCNC(=O)OC(C)(C)C)c3)n2)ccn1)CC(=O)OC(C)(C)C]

A mixture of intermediate 19 (0.00025 mol) in DMF (q.s.) was hydrogenated for 4 hours at room temperature (atmospheric pressure) with Raney Nickel (q.s.) as a catalyst. After uptake of $H_2$ (2 equiv), the catalyst was filtered off and the filtrate was evaporated, yielding crude intermediate 20 (used in next reaction step without further purification).

e) Preparation of Intermediate 21

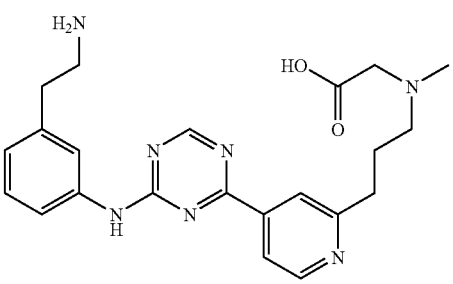 [SMILES: CN(CCCc1cc(-c2ncnc(Nc3cccc(CCN)c3)n2)ccn1)CC(=O)O]

A solution of intermediate 20 (0.00025 mol) in TFA/$CH_2Cl_2$/TIS (49/49/2) (10 ml) was stirred for 45 minutes at 45° C. The solvent was evaporated and the residue was redissolved in DMF, yielding crude intermediate 21 (TFA salt, used in next reaction step without further purification).

Example A6 a) Preparation of Intermediate 22

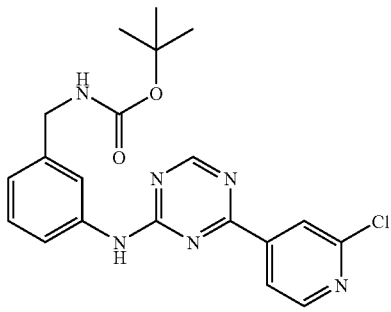 [SMILES: CC(C)(C)OC(=O)NCc1cccc(Nc2ncnc(-c3ccnc(Cl)c3)n2)c1]

A solution of 2-chloro-4-(2-chloro-4-pyridinyl)-1,3,5-triazine (0.01 mol), 1,1-dimethylethyl ester[(3-aminophenyl)methyl]carbamic acid (0.01 mol) and DIPEA (0.02 mol) in trichloromethane (40 ml) was stirred at 60° C. Extra DIPEA (120 ml) was added and the resultant reaction mixture was stirred for 75 minutes at room temperature. The precipitate was filtered off, washed with DIPEA, then with hexane, then dried (vacuum, 65° C.), yielding 4.05 g (98%; yellow crystals; M.P.: 144.0-145.6° C.) of intermediate 22.

b) Preparation of Intermediate 23

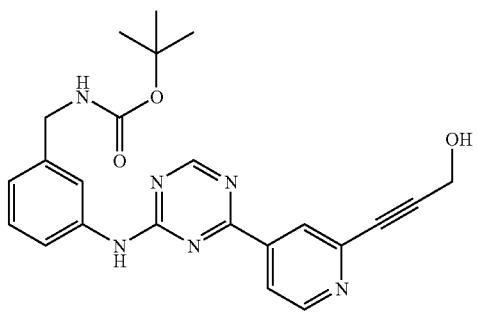 [SMILES: CC(C)(C)OC(=O)NCc1cccc(Nc2ncnc(-c3ccnc(C#CCO)c3)n2)c1]

A mixture of intermediate 22 (0.0095 mol), 2-propyn-1-ol (0.01425 mol), N-ethylethanamine (1.468 ml), dichlorobis(triphenylphosphine)palladium (0.00048 mol), copper(I) iodide (0.00048 mol) and triphenylphosphine (0.00190 mol) in DMF (100 ml) was stirred at room temperature. $N_2$ gas was bubbled through the mixture for 15 minutes. The reaction mixture was stirred at 60° C. (nitrogen atmosphere) for 24 hours. More 2-propyn-1-ol (0.01425 mol) and dichlorobis(triphenylphosphine)palladium (0.000048 mol) were added. Extra N-ethylethanamine (15 ml) was added and the reaction mixture was stirred overnight at 60° C. Upon cooling, water (15 ml) was added and the solvent was evaporated. The residue was purified over silica gel (eluent: $CH_2Cl_2$/MeOH gradient from 100/0 to 95/5), then purified further over a pad of silica gel (eluent: $CH_2Cl_2$/(7N $NH_3$/MeOH) 98/2). The desired product fractions were collected and the solvent was evaporated. The residue was crystallized from MeOH, filtered off and dried, yielding 2.22 g (54%; M.P.: 129.1-130.5° C.) of intermediate 23.

c) Preparation of Intermediate 24

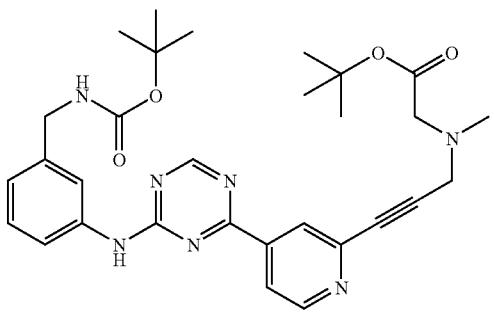 [SMILES: CN(CC#Cc1cc(-c2ncnc(Nc3cccc(CNC(=O)OC(C)(C)C)c3)n2)ccn1)CC(=O)OC(C)(C)C]

Intermediate 23 (0.00025 mol) was dissolved in DMF (10 ml). Methanesulfonyl chloride (0.000375 mol) was added. The mixture was stirred for 15 minutes at room temperature. N-methylglycine 1,1-dimethylethyl ester hydrochloride (0.000750 mol) was added while stirring. DIPEA (0.0015 mol) was added and the reaction mixture was stirred for 22 hours at 65° C. The desired product was obtained.

1-Ethenyl-4-(isocyanatomethyl)benzene, polymer with ethenylbenzene (0.001 mol) was added and the mixture was shaken for 24 hours at room temperature. The resin was filtered off, washed with DMF (20 ml) and the filtrate containing crude intermediate 24 was used as such in the next reaction step.

Intermediate 24a was prepared analogously from Intermediate 82 using N-methylglycine 1,1-dimethylethyl ester hydrochloride.

d) Preparation of Intermediate 25

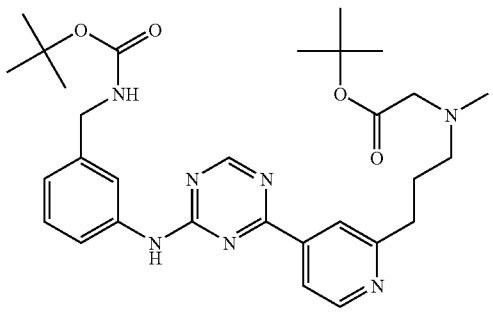 [SMILES: CN(CCCc1cc(-c2ncnc(Nc3cccc(CNC(=O)OC(C)(C)C)c3)n2)ccn1)CC(=O)OC(C)(C)C]

A mixture of intermediate 24 (0.00025 mol) in DMF (40 ml) was hydrogenated overnight with Pd/C (10%) (0.1 g) as a catalyst. After uptake of $H_2$ (2 equiv), the catalyst was filtered off and the filtrate was evaporated, yielding crude intermediate 25 (used in next reaction step without further purification).

Intermediate 25a was prepared analogously from Intermediate 24a e) Preparation of Intermediate 26

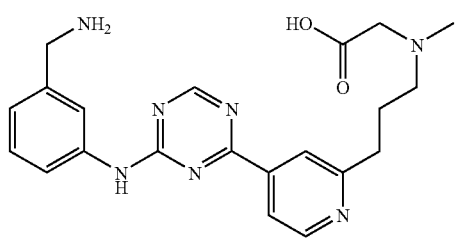 [SMILES: CN(CCCc1cc(-c2ncnc(Nc3cccc(CN)c3)n2)ccn1)CC(=O)O]

A solution of intermediate 25 (0.00025 mol) in TFA/$CH_2Cl_2$/TIS (49/49/2) (10 ml) was stirred for 60 minutes at room temperature, then for 1 hour at 50° C. The solvent was evaporated, yielding intermediate 26 (TFA salt, used in next reaction step without further purification).

Intermediate 26a was prepared analogously from Intermediate 25a

Example A7 a) Preparation of Intermediate 27

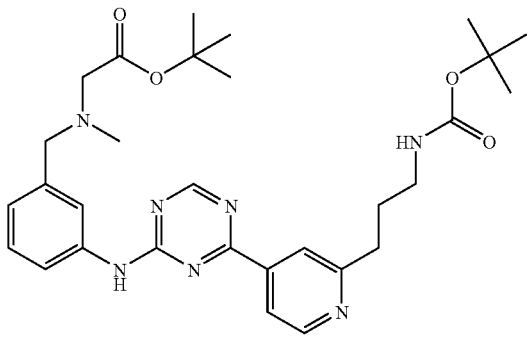 [SMILES: CN(CC(=O)OC(C)(C)C)Cc1cccc(Nc2ncnc(-c3ccnc(CCCNC(=O)OC(C)(C)C)c3)n2)c1]

Intermediate 5 (0.00229 mol) was dissolved in DMF (20 ml). DIPEA (0.01374 mol), then methanesulfonyl chloride (0.00275 mol) were added. The mixture was stirred for 5 minutes at room temperature. N-methylglycine 1,1-dimethylethyl ester hydrochloride (0.00458 mol) was added and the reaction mixture was stirred overnight at 65° C. The mixture was cooled to room temperature. MP-NCO (0.00458 mol) was added and the mixture was shaken over the weekend at room temperature. The resin was filtered off, washed with DMF (4×5 ml) and the filtrate's solvent was evaporated, yielding intermediate 27.

b) Preparation of Intermediate 28

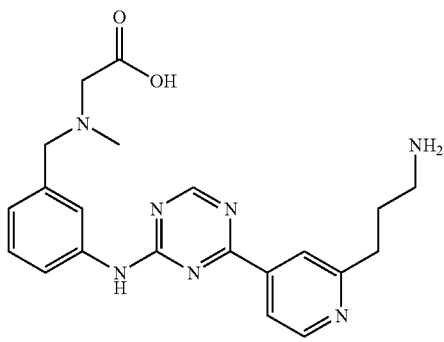 [SMILES: CN(CC(=O)O)Cc1cccc(Nc2ncnc(-c3ccnc(CCCN)c3)n2)c1]

A solution of intermediate 27 (0.00229 mol) in TFA/CH$_2$Cl$_2$/TIS (49/49/2) (20 ml) was shaken for 60 minutes at 40° C. More TFA/CH$_2$Cl$_2$/TIS (49/49/2) (10 ml) was added and the reaction mixture was shaken another hour at 40° C. The solvent was evaporated, yielding crude intermediate 28 as a TFA salt (used as such in the next reaction step).

Example A9 a) Preparation of Intermediate 31

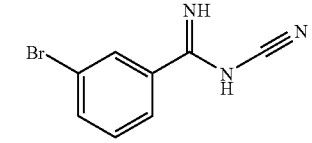 [SMILES: N#CNC(=N)c1cccc(Br)c1]

Sodium methoxide (0.30 g, 0.0055 mol) was added to a solution of 1-bromo-3-cyanobenzene (10.00 g, 0.055 mol) in methanol (55 ml), and the resulting mixture was stirred at room temperature for 4 hours. Next, cyanamide (3.46 g, 0.082 mol) was added, and the mixture was stirred overnight at r.t. Dichloromethane (200 ml) was then added and the resulting solution was washed with brine (3×200 ml). Drying on MgSO$_4$, filtration and evaporation of the solvent yielded 10.62 g of intermediate 31 (white solid, yield: 86%).

b) Preparation of Intermediate 32

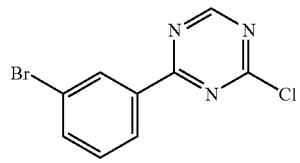 [SMILES: Clc1ncnc(-c2cccc(Br)c2)n1]

To a solution of intermediate 31 (2.63 g, 0.012 mol) in CH$_3$CN (25 ml) was slowly added 2.25 g (0.018 mol) of N-(chloromethylene)-N-methylmethanaminium chloride. After 5 minutes of stirring at room temperature, the mixture became homogeneous, and after 30 minutes a precipitate appeared. The reaction was stirred for one additional hour and then quenched by adding saturated aqueous sodium bicarbonate. The aqueous phase was extracted with dichloromethane (3×50 ml) and the combined organic layers were dried over MgSO$_4$. Filtration and evaporation of the solvent yielded 2.98 g of intermediate 32 (yellow solid, yield: 94%), which was used as such for the next reaction step.

Example A10 a) Preparation of Intermediate 33

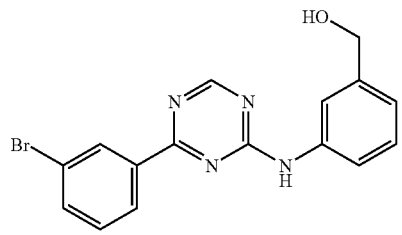 [SMILES: OCc1cccc(Nc2ncnc(-c3cccc(Br)c3)n2)c1]

3-Amino benzyl alcohol (0.27 g, 0.0022 mol) was added to a solution of intermediate 32 (0.49 g, 0.0018 mol) in 1,4-dioxane (9 ml). Then DIPEA (0.24 g, 0.0018 mol) was added and the mixture was stirred at room temperature for 3 hours. Next, 20 ml of CH$_2$Cl$_2$ and 20 ml of water were added, and the aqueous phase was extracted with CH$_2$Cl$_2$ (2×20 ml). The combined organic layers were dried over MgSO$_4$. Filtration and evaporation of the solvent yielded 0.53 g of intermediate 33 (white solid, yield: 82%), which was used as such for the next reaction step.

b) Preparation of Intermediate 34

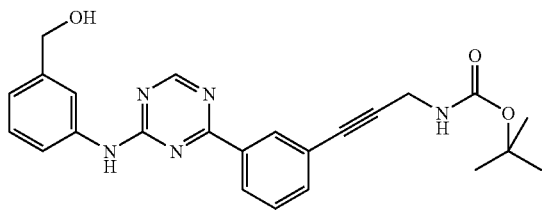 [SMILES: CC(C)(C)OC(=O)NCC#Cc1cccc(-c2ncnc(Nc3cccc(CO)c3)n2)c1]

Intermediate 33 (2.32 g, 0.0065 mol), 1,1-dimethylethyl ester 2-propynyl carbamic acid [92136-39-5] (2.52 g, 0.016 mol), dichlorobis(triphenylphosphine)palladium 0.456 g, 0.0006 mol), copper(I) iodide (0.124 g, 0.0006 mol) and triphenylphosphine (0.681 g, 0.0026 mol) were dissolved in DMF (80 ml). N$_2$ gas was bubbled through the mixture for 10 minutes, after which N-ethylethanamine (10.2 ml, 0.097 mol) was added. The reaction was then stirred at 60° C. for 18 hours under N$_2$ atmosphere. After cooling to room temperature, CH$_2$Cl$_2$ (50 ml) was added and the organic layer was washed with 3×20 ml of brine and then dried on MgSO$_4$. The solvent was evaporated and the residue was purified by flash column chromatography using CH$_2$Cl$_2$/MeOH (9:1) as eluent. Evaporation of the combined product fractions provided 2.24 g of intermediate 34 (yellow solid, 80%).

Example A11 a) Preparation of Intermediate 35

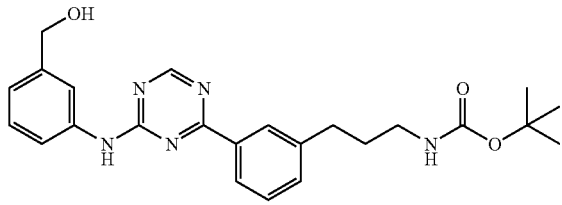 [SMILES: CC(C)(C)OC(=O)NCCCc1cccc(-c2ncnc(Nc3cccc(CO)c3)n2)c1]

A mixture of intermediate 34 (5.44 g, 0.013 mol) and Et$_3$N (2.5 ml, 0.018 mol) in MeOH (190 ml) was hydrogenated (1 atm H$_2$) for 15 hours with 10% Pd/C (0.544 g) as a catalyst. After uptake of H$_2$ (2 equiv), reaction was filtered over celite and the filtrate was concentrated. Intermediate 35 was obtained by filtration after trituration with diisopropyl ether (pale yellow solid, 5.00 g, yield: 91%).

b) Preparation of Intermediate 36

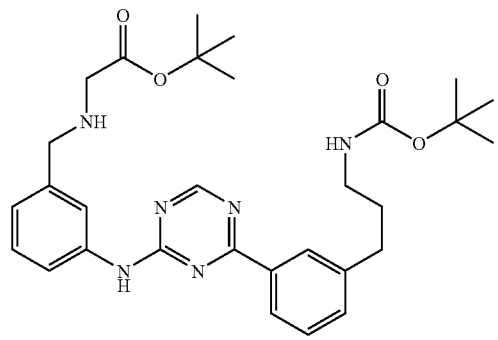 [SMILES: CC(C)(C)OC(=O)CNCc1cccc(Nc2ncnc(-c3cccc(CCCNC(=O)OC(C)(C)C)c3)n2)c1]

To a solution of intermediate 35 (1.85 g, 0.00425 mol) and DIPEA (4.33 ml, 0.0255 mol) in DMF (80 ml) was added 0.493 ml (0.00638 mol) of mesyl chloride. This mixture was stirred for 30 minutes. Next, 5 ml (0.00025 mol) of this solution was added to the amino acid ester, in casu glycine 1,1-dimethylethyl ester hydrochloride (0.00125 mol), and the resulting mixture was stirred overnight at 65° C. Then, the mixture was cooled to room temperature and 4-formylphenoxypolystyrene resin (1.00 g, 0.0021 mol) was added. Upon shaking over the weekend, the resin was filtered off and washed with MeOH and MeOH/CH$_2$Cl$_2$ alternatingly (portions of 5 ml). Evaporation of the solvent provided intermediate 36, which was used as such for the next reaction step.

Intermediate 36a was prepared analogously from Intermediate 85 using 2-amino-3-tert-butoxy-propionic acid tert-butyl ester hydrochloride.

c) Preparation of Intermediate 37

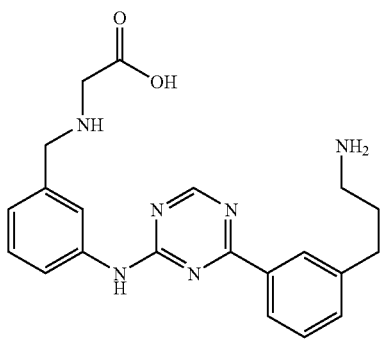 [SMILES: NCCCc1cccc(-c2ncnc(Nc3cccc(CNCC(=O)O)c3)n2)c1]

Intermediate 36 (crude compound) was dissolved in TFA/CH$_2$Cl$_2$/TIS (49/49/2) (5 ml) and shaken overnight at rt. Next, the solvent was evaporated, yielding intermediate 37 (TFA salt), which was used as such for the next reaction step.

Intermediate 37a was prepared analogously from Intermediate 36a.

Example A12 b) Preparation of Intermediate 38

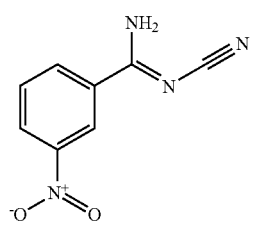

Sodium methoxide (0.35 g, 0.0064 mol) was added to a solution of 1-cyano-3-nitrobenzene (9.48 g, 0.064 mol) in methanol (64 ml), and the resulting mixture was stirred at rt for 4 hours. Next, cyanamide (4.00 g, 0.096 mol) was added, and the mixture was stirred overnight at rt. Diethyl ether (200 ml) was then added. The resulting precipitate was filtered off, washed with ether and dried, yielding 11.53 g of intermediate 38 (white solid, yield: 95%).

b) Preparation of Intermediate 39

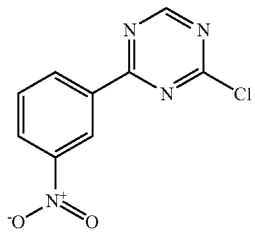

To a solution of intermediate 38 (11.53 g, 0.061 mol) in CH$_3$CN (120 ml) was slowly added 11.60 g (0.091 mol) of N-(chloromethylene)-N-methylmethanaminium chloride. After 5 minutes of stirring at rt, the mixture became homogeneous, and after 30 minutes a precipitate appeared. The reaction was stirred for one additional hour and then quenched by adding saturated aqueous sodium bicarbonate. The aqueous phase was extracted with dichloromethane (3×50 ml) and the combined organic layers were dried over MgSO$_4$. Filtration and evaporation of the solvent yielded 12.60 g of intermediate 39 (pale yellow solid, yield: 88%).

Example A13 a) Preparation of Intermediate 40

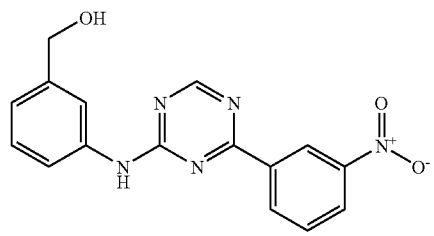 [SMILES: O=[N+]([O-])c1cccc(-c2ncnc(Nc3cccc(CO)c3)n2)c1]

3-Amino benzyl alcohol (1.19 g, 0.0096 mol) was added to a solution of intermediate 39 (1.90 g, 0.0080 mol) in 1,4-dioxane (40 ml). Then DIPEA (1.05 g, 0.0081 mol) was added and the mixture was stirred at rt for 5 hours. Next, the mixture was poured into ice-water, and the resulting precipitate was washed with water (50 ml), and then with cold diethyl ether (50 ml). Drying in vacuo yielded 2.36 g of intermediate 40 (pale yellow solid, yield: 89%).

b) Preparation of Intermediate 41

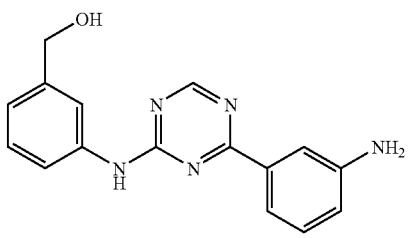 [SMILES: Nc1cccc(-c2ncnc(Nc3cccc(CO)c3)n2)c1]

To a suspension of intermediate 40 (4.52 g, 0.014 mol) in MeOH (85 ml) was added Et$_3$N (1.9 ml, 0.014 mol). The resulting mixture was hydrogenated (1 atm H$_2$) for 48 hours with 10% Pd/C (0.45 g) as a catalyst. After uptake of H$_2$ (3 equiv), 100 ml of 1,4-dioxane/MeOH (4:1) was added and the resulting solution was filtered over a bed of celite. Evaporation of the solvent provided intermediate 41 as a pale yellow solid (3.07 g, yield: 75%).

Example A14 a) Preparation of Intermediate 42

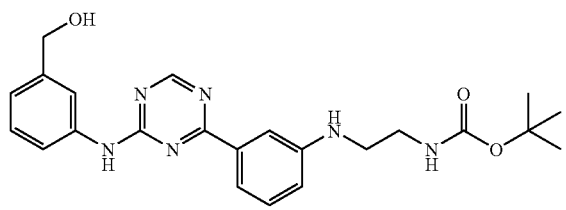 [SMILES: CC(C)(C)OC(=O)NCCNc1cccc(-c2ncnc(Nc3cccc(CO)c3)n2)c1]

A mixture of intermediate 41 (5.00 g, 0.017 mol), (2-oxo-ethyl)carbamic acid tert-butyl ester (3.26 g, 0.020 mol) and titanium(IV) isopropoxide (7.26 g, 0.026 mol) in 1,2-dichloroethane (250 ml) was stirred at room temperature for 3.5 hours. Then acetic acid (3.07 g, 0.051 mol) was added, followed by 7.95 g (0.0375 mol) of sodium triacetoxyborohydride and the resulting mixture was stirred for 15 hours at rt. Next, the reaction was quenched with aqueous saturated potassium carbonate. The organic layer was separated, and the aqueous phase extracted with CHCl₃ (3×50 ml). The combined organic layers were washed with brine (250 ml) and dried on MgSO₄. After removal of the solvent, a purification was carried out using flash column chromatography (eluent: CH₂Cl₂/MeOH/Et₃N, gradient 99:0:1 to 98:1:1). Evaporation of the combined product fractions provided crude intermediate 42, which was triturated with diisopropyl ether. Filtration and drying of the resulting solid provided 3.00 g of intermediate 42 (pale yellow solid, yield: 40%).

b) Preparation of Intermediate 43

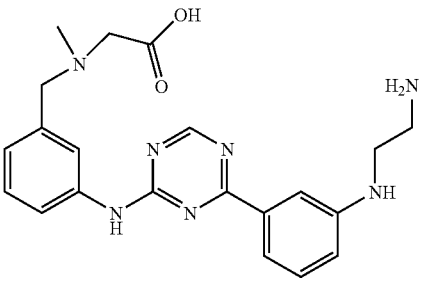 [SMILES: CN(CC(=O)O)Cc1cccc(Nc2ncnc(-c3cccc(NCCN)c3)n2)c1]

To a solution of intermediate 42 (0.982 g, 0.00225 mol) and DIPEA (2.30 ml, 0.0135 mol) in DMF (42 ml) was added 0.209 ml (0.00270 mol) of mesyl chloride. This mixture was stirred for 30 minutes. Next, 5 ml (0.00025 mol) of this solution was added to the amino acid ester, in casu N-methylglycine 1,1-dimethylethyl ester hydrochloride (0.00075 mol), and the resulting mixture was stirred overnight at 65° C. Then, the mixture was cooled to room temperature and MP-NCO (6 equiv) was added. Upon shaking overnight, the resin was filtered off and washed with DMF (2×5 ml). Evaporation of the solvent provided intermediate 43, which was used as such for the next reaction step.

Intermediate 43a was prepared analogously from Intermediate 45 using 2-amino-3-phenyl-propionic acid tert-butyl ester hydrochloride.

c) Preparation of Intermediate 44

Intermediate 43 (crude compound) was dissolved in TFA/CH₂Cl₂/TIS (49/49/2) (5 ml) and shaken overnight at rt. Next, the solvent was evaporated, yielding intermediate 44 as a TFA salt, which was used as such for the next reaction step.

Intermediate 44a was prepared analogously from Intermediate 43a

Example A15 a) Preparation of Intermediate 45

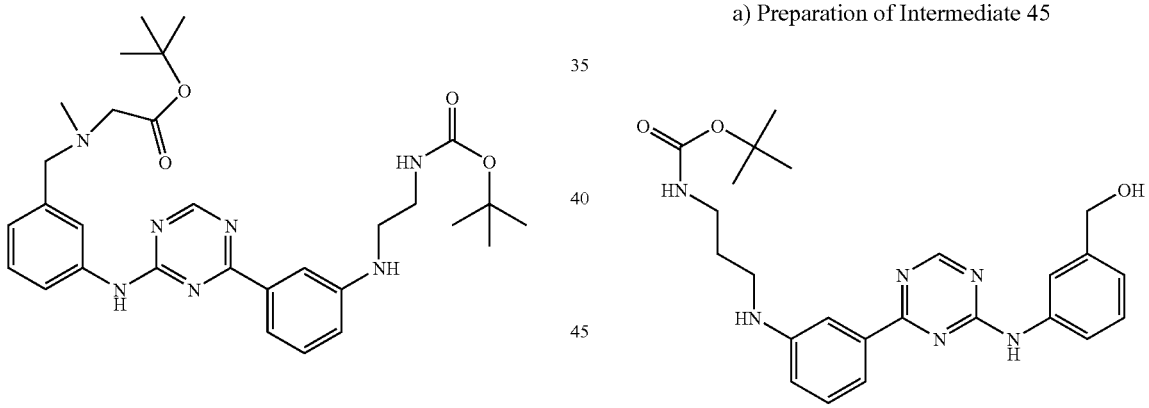

A mixture of intermediate 41 (1.60 g, 0.0055 mol), (3-oxopropyl)carbamic acid tert-butyl ester (2.38 g, 0.014 mol) and titanium(IV) isopropoxide (3.21 g, 0.011 mol) in 1,2-dichloroethane (82 ml) was stirred at room temperature for 3.5 hours. Then acetic acid (1.15 g, 0.019 mol) was added, followed by 3.14 g (0.015 mol) of sodium triacetoxyborohydride and the resulting mixture was stirred for 15 hours at rt. Next, the reaction was quenched with aqueous saturated potassium carbonate. The resulting emulsion with precipitates was filtered. The organic layer of the filtrate was separated and the filter cake was extracted with CH₂Cl₂/CHCl₃ (3×50 ml). The combined organic layers were washed with brine (250 ml) and dried on MgSO₄. After removal of the solvent, a purification was carried out using flash column chromatography (eluent: CH₂Cl₂/MeOH/NEt₃, gradient 99:0:1 to 98.8:0.2:1). Evaporation of the combined product fractions provided crude intermediate 45, which was triturated with diisopropyl ether. Filtration and drying of the resulting solid provided 0.67 g of intermediate 45 (yellow solid, yield: 27%).

Example A16 a) Preparation of Intermediate 46

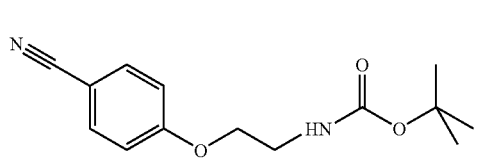 [SMILES: CC(C)(C)OC(=O)NCCOc1ccc(C#N)cc1]

Cs$_2$CO$_3$ (0.250 mol) was added to a solution of 4-hydroxybenzonitrile (0.125 mol) in DMF (380 ml), stirred at room temperature. The mixture was stirred for 30 minutes at room temperature. (2-Bromoethyl)-1,1-dimethylethyl ester carbamic acid (0.187 mol) was added and the reaction mixture was stirred overnight at room temperature. The precipitate was filtered off, washed with EtOAc, and then a mixture of EtOAc and brine was added. The layers were separated. The organic phase was washed with brine, then dried (MgSO$_4$), filtered and the solvent was evaporated. The residue was purified by flash column chromatography over silica gel (eluent: hexane/EtOAc 10/1 to 6/1). The product fractions were collected and the solvent was evaporated, yielding 23.44 g (yield 73%; white solid) of intermediate 46.

b) Preparation of Intermediate 47

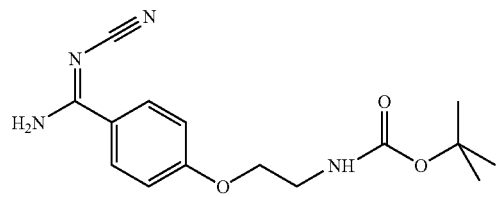 [SMILES: CC(C)(C)OC(=O)NCCOc1ccc(/C(N)=N\C#N)cc1]

NaOCH$_3$ (0.0553 mol) was added to a solution of intermediate 46 (0.0276 mol) in MeOH (83 ml). The mixture was stirred for 2 hours at room temperature. Cyanamide (0.0553 mol) was added in one portion. The reaction mixture was stirred for 48 hours at room temperature. During a period of 7 days, each day, extra NaOCH$_3$ (1 equiv) was added as well as extra cyanamide (6 equiv). The resulting precipitate was filtered off, then washed with methanol and diethyl ether. The solvent was evaporated. The residue was purified by flash column chromatography over silica gel (eluent: hexane/EtOAc 30/10 over 20/10 to 10/10). The product fractions were collected and the solvent was evaporated. The residue was dried in vacuo at room temperature, yielding 2.8 g (yield 33%; white solid) of intermediate 47.

c) Preparation of Intermediate 48

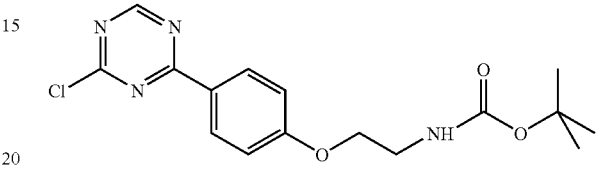

Intermediate 47 (0.0092 mol) was dissolved in CH$_3$CN (20 ml). N-(chloromethylene)-N-methyl-methanaminium chloride (0.0138 mol) was added and the reaction mixture was stirred for 1.5 hours at room temperature. The reaction was quenched by adding water. CH$_2$Cl$_2$ was added. The layers were separated The aqueous phase was extracted with CH$_2$Cl$_2$. The organic layers were combined, washed with brine, dried (MgSO$_4$), filtered and the solvent was evaporated. The residue was dried in vacuo at room temperature, yielding 1.5 g (yellow solid, used in next reaction step, without further purification) of intermediate 48.

d) Preparation of Intermediate 49

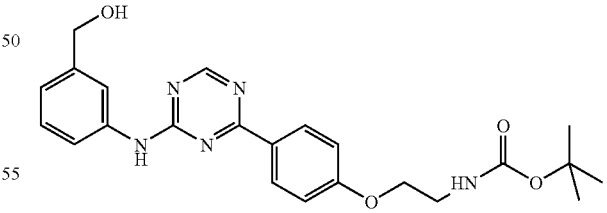

Intermediate 48 (0.0043 mol) was dissolved in 1,4-dioxane (20 ml). 3-Amino-benzenemethanol (0.0051 mol) was added. DIPEA (0.0086 mol) was added and the reaction mixture was stirred for 15 hours at room temperature. CH$_2$Cl$_2$ (20 ml) and brine (20 ml) were added. The organic phase was separated, then washed with brine, dried (MgSO$_4$), filtered and the solvent was evaporated. The residue was purified by column chromatography over silica gel (eluent: hexane/EtOAc from 3/1 to 1/1). The product fractions were collected and the solvent was evaporated. The residue was dried in vacuo at room temperature, yielding 1.5 g (38%) of intermediate 49.

e) Preparation of Intermediate 50

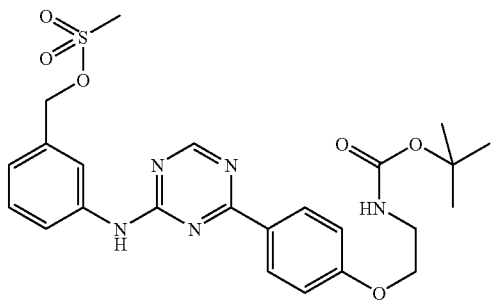 [SMILES: CC(C)(C)OC(=O)NCCOc1ccc(-c2ncnc(Nc3cccc(COS(C)(=O)=O)c3)n2)cc1]

DIPEA (2.7 ml) was added to a stirred solution of intermediate 49 (0.00265 mol) in DMF (50 ml). Methanesulfonyl chloride (0.349 ml) was added and the reaction mixture was stirred for one hour at room temperature. More methanesulfonyl chloride (0.103 ml) was added and the reaction mixture was stirred for one hour at room temperature, yielding crude reaction solution containing intermediate 50 as used in next reaction step, without further purification.

f) Preparation of Intermediate 51

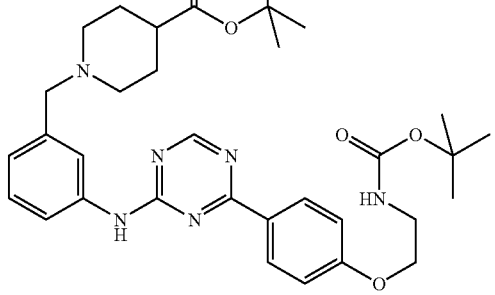

1,1-Dimethylethyl ester 4-piperidinecarboxylic acid (0.0005 mol) was added to part (5 ml) of crude reaction solution of intermediate 50 in DMF (50 ml) and DIPEA (2.7 ml). The reaction mixture was stirred overnight at 70° C. Macroporous benzyl isocyanate scavenger (0.00075 mol) was added, and the mixture was stirred overnight at room temperature. The resin was filtered off, washed with methanol, then with MeOH/CH$_2$Cl$_2$ 1/10 and the filtrate's solvent was evaporated, yielding intermediate 51 which was used as such in the next step.

g) Preparation of Intermediate 52

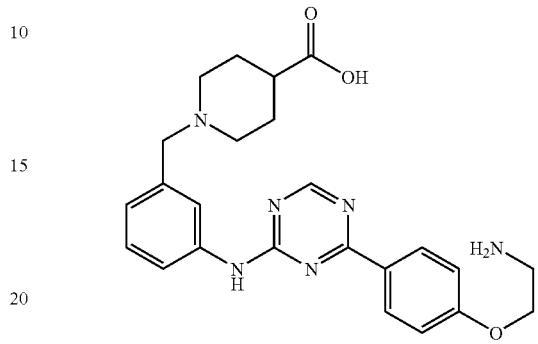

Crude intermediate 51 (max. 0.000250 mol) was taken up into TFA/CH$_2$Cl$_2$/TIS 49/49/2 (5 ml). The mixture was shaken for 5 hours at room temperature. The solvent was evaporated, yielding crude intermediate 52 (TFA salt, used in next reaction step without further purification).

Example A17 a) Preparation of Intermediate 53

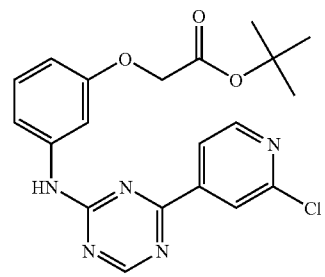 [SMILES: CC(C)(C)OC(=O)COc1cccc(Nc2ncnc(-c3ccnc(Cl)c3)n2)c1]

A mixture of 2-chloro-4-(2-chloro-4-pyridinyl)-1,3,5-triazine (0.05 mol), (3-aminophenoxy)-1,1-dimethylethyl ester acetic acid (0.05 mol), DIPEA (0.2 mol) in CHCl$_3$ (500 ml) was stirred 4 hours at 60° C. The reaction mixture was washed 2 times with H$_2$O (250 ml; aqua destillata). The separated organic layer was dried (Na$_2$SO$_4$) and the filtrate's solvent was evaporated. The residue was recrystallized from CH$_3$CN/

H$_2$O, yielding 15.30 g (74%; M.P.: 121.5° C. to 122.7° C.; NMR confirmed structure) of intermediate 53.

b) Preparation of Intermediate 54

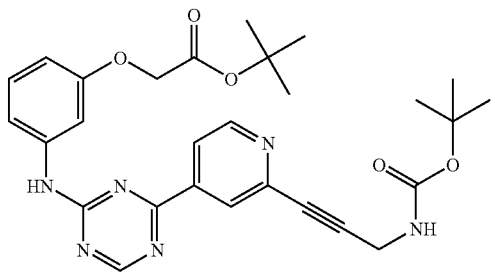 [SMILES: CC(C)(C)OC(=O)COc1cccc(Nc2ncnc(-c3ccnc(C#CCNC(=O)OC(C)(C)C)c3)n2)c1]

Intermediate 53 (0.005 mol), 2-propynyl-1,1-dimethylethyl ester carbamic acid (0.006 mol), diethylamine (0.075 mol), dichlorobis(triphenylphosphine)palladium (0.00025 mol), copper(I) iodide (0.00025 mol) and triphenylphosphine (0.001 mol) were dissolved in DMF (50 ml) and N$_2$ was bubbled in the reaction mixture for 5 minutes. The reaction mixture was stirred for 16 hours at 60° C. (nitrogen atmosphere). H$_2$O (10 ml) was added to the reaction mixture and the solvent was evaporated. The residue was purified by flash column chromatography over silica gel (eluent: CH$_2$Cl$_2$/MeOH from 100/0 to 90/10). The product fractions were collected and the solvent was evaporated. The residue was recrystallized from DIPE, yielding 1.8034 g (68%; M.P.: 161.2° C. to 162.5° C.) of intermediate 54.

c) Preparation of Intermediate 55

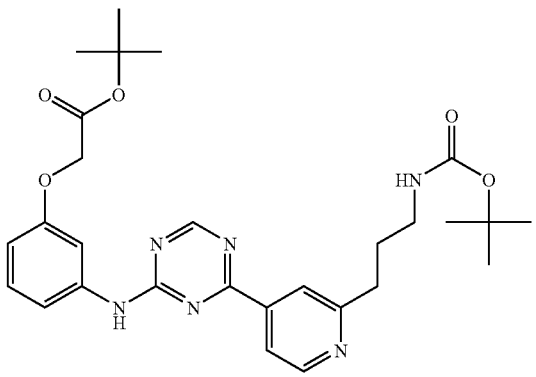 [SMILES: CC(C)(C)OC(=O)COc1cccc(Nc2ncnc(-c3ccnc(CCCNC(=O)OC(C)(C)C)c3)n2)c1]

A mixture of intermediate 54 (0.0028 mol) in THF (50 ml) was hydrogenated with Raney Nickel (catalytic quantities) as a catalyst. After 20 hours and uptake of H$_2$ (2 equiv; 140 ml), the catalyst was filtered off. The filtrate's solvent was evaporated. The residue was recrystallized from DIPE, yielding 1.3161 g (88%; M.P.: 146.5° C. to 148.4° C.) of intermediate 55.

d) Preparation of Intermediate 56

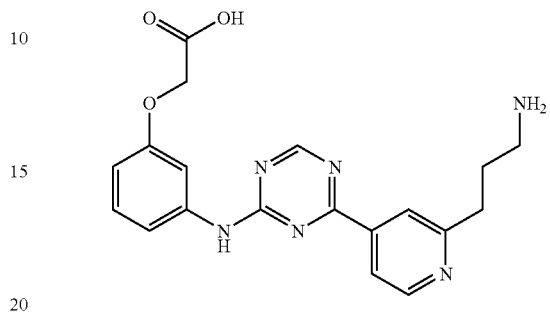

Intermediate 55 (0.002 mol) was dissolved in a mixture of TFA/CH$_2$Cl$_2$/TIS (49/49/2, 20 ml) and stirred for 2.5 hours at room temperature. The solvent was evaporated and co-evaporated 3 times with CH$_3$CN, yielding (LCMS: 94%; crude used as such in next reaction step) of intermediate 56 as a TFA salt (C$_2$HF$_3$O$_2$).

Example A18 a) Preparation of Intermediate and Intermediate 57

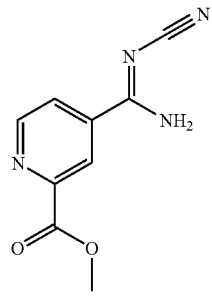

4-Cyano-2-pyridinecarboxylic acid ethyl ester (0.090 mol) in MeOH (100 ml) was stirred. NaOCH$_3$ (0.00905 mol) was stirred for one hour at room temperature and the mixture became homogenous. H$_2$N—CN (0.135 mol) was added and the reaction mixture was stirred for 5 hours at room temperature. More NaOCH$_3$ (0.5 equiv) and H$_2$N—CN (0.75 equiv) were added and the reaction mixture was stirred overnight at room temperature. The mixture was filtered. To the filtrate, more NaOCH$_3$ (0.05 equiv) was added and that mixture was stirred for 3 hours and the resulting precipitate was again filtered off. The filtrate was purified by column chromatography over silica gel (eluent: CH$_2$Cl$_2$/MeOH 30/1). The product fractions were collected and the solvent was evaporated, yielding 9 g of intermediate 57 (49%).

b) Preparation of Intermediate 58

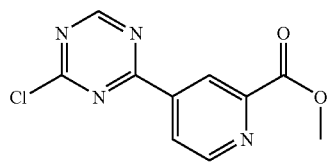 [SMILES: COC(=O)c1cc(-c2ncnc(Cl)n2)ccn1]

Intermediate 57 (0.044 mol) was suspended in $CH_2Cl_2$ (150 ml). N-(chloromethylene)-N-methyl-methanaminium chloride (0.066 mol) was added and the reaction mixture was stirred overnight at room temperature. The reaction mixture was washed with a saturated aqueous $NaHCO_3$ solution, then extracted with $CH_2Cl_2$. The separated organic layer was dried ($MgSO_4$), filtered and the solvent evaporated, yielding 10.42 g (95%) of intermediate 58.

c) Preparation of Intermediate 59

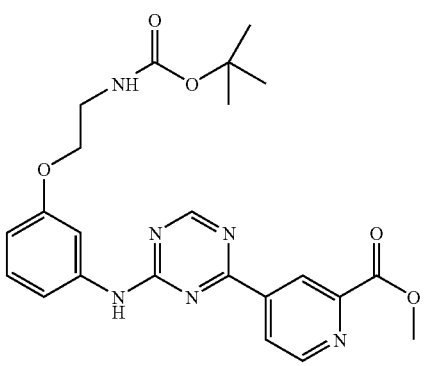 [SMILES: COC(=O)c1cc(-c2ncnc(Nc3cccc(OCCNC(=O)OC(C)(C)C)c3)n2)ccn1]

Intermediate 58 (0.021 mol) was dissolved in a mixture of 1,4-dioxane (90 ml) and $CH_2Cl_2$ (10 ml). [2-(3-Aminophenoxy)ethyl]-1,1-dimethylethyl ester carbamic acid (0.024 mol) was added. DIPEA (0.042 mol) was added and the reaction mixture was stirred overnight at room temperature. The solvent was evaporated. The residue was dissolved in $CH_2Cl_2$. The organic solution was washed with a saturated aqueous $NaHCO_3$ solution. The aqueous phase was extracted with $CH_2Cl_2$. The separated organic layer was dried ($MgSO_4$), and the solvent evaporated. The residue was purified by column chromatography over silica gel (eluent: hexane/EtOAc from 1/1 to 0/1). The product fractions were collected and the solvent was evaporated, yielding 8.50 g (87%) of intermediate 59.

d) Preparation of Intermediate 60

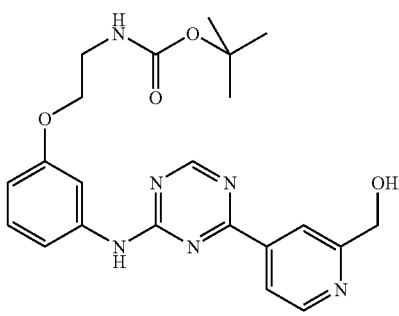 [SMILES: CC(C)(C)OC(=O)NCCOc1cccc(Nc2ncnc(-c3ccnc(CO)c3)n2)c1]

$CaCl_2$ (0.012 mol) was added to MeOH (180 ml). The mixture was stirred and cooled at −10° C., under $N_2$ atmosphere. $NaBH_4$ (0.018 mol) was added and stirring was continued for 20 minutes. A solution of intermediate 59 (0.018 mol) in MeOH (90 ml) was cooled to −10° C., then added to $CaCl_2/NaBH_4/MeOH$ at −10° C. The resultant reaction mixture was stirred, allowing the temperature to rise to room temperature. 2-Propanone was added. The solvent was evaporated. The residue was washed in 1 M NaOH, then extracted twice with $CH_2Cl_2$. The separated organic layer was dried ($MgSO_4$), filtered and the solvent evaporated. The residue was purified by column chromatography over silica gel (eluent: EtOAc/hexane 1/2, then $CH_2Cl_2$/MeOH 30/1 to 20/1). The product fractions were collected and the solvent was evaporated, yielding 5.205 g (66%) of intermediate 60.

e) Preparation of Intermediate 61

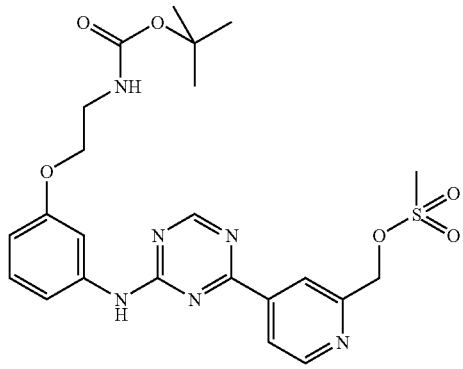 [SMILES: CC(C)(C)OC(=O)NCCOc1cccc(Nc2ncnc(-c3ccnc(COS(C)(=O)=O)c3)n2)c1]

DMF (90 ml) was added to intermediate 60 (0.00450 mol) in DIPEA (4.59 ml). Methanesulfonyl chloride (0.52 ml) was added and the reaction mixture was stirred for one hour, yielding crude reaction solution, containing intermediate 61 used in next reaction step without further purification.

f) Preparation of Intermediate 62

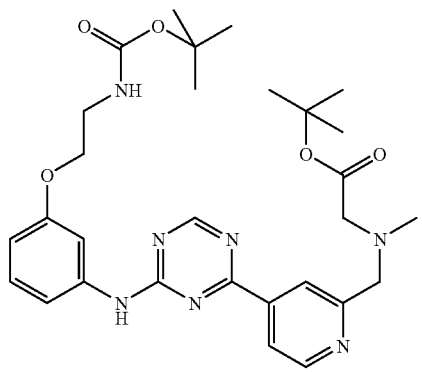 [SMILES: CN(CC(=O)OC(C)(C)C)Cc1cc(-c2ncnc(Nc3cccc(OCCNC(=O)OC(C)(C)C)c3)n2)ccn1]

Crude intermediate 61 in 5 mL DMF (0.00025 mol) and DIPEA (4.59 ml) was added to N-methylglycine 1,1-dimethylethyl ester hydrochloride (0.0005 mol). The reaction mixture was stirred overnight at 65° C. Excess macroporous benzyl isocyanate scavenger was added, and the mixture was stirred overnight at room temperature. The resin was filtered off, washed with methanol, then with methanol/$CH_2Cl_2$ 1/4 and the filtrate's solvent was evaporated, yielding intermediate 62 which was used as such in the next step.

g) Preparation of Intermediate 63

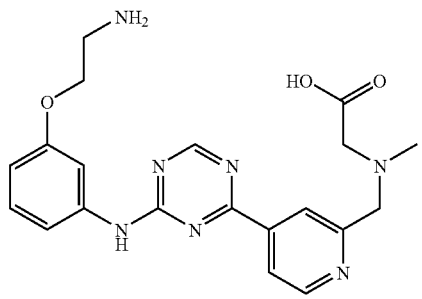 [SMILES: CN(CC(=O)O)Cc1cc(-c2ncnc(Nc3cccc(OCCN)c3)n2)ccn1]

Crude intermediate 62 (max. 0.000250 mol) was taken up into TFA/$CH_2Cl_2$/TIS 49/49/2 (5 ml). The mixture was shaken overnight at room temperature. The solvent was evaporated, yielding crude intermediate 63 (TFA salt, used in next reaction step without further purification).

Example A19 a) Preparation of Intermediate 64

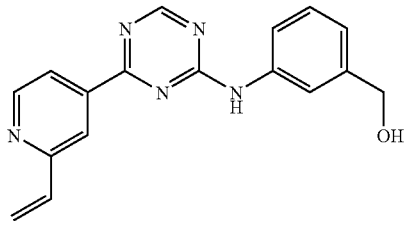 [SMILES: C=Cc1cc(-c2ncnc(Nc3cccc(CO)c3)n2)ccn1]

To a mixture of intermediate 1 (0.016 mol) in extra dry DMF (240 ml), first Pd(PPh$_3$)$_4$ (0.0008 mol) and triphenylphosphine (0.0016 mol), and then tributylethenylstannane (0.024 mol) were added. The reaction mixture was stirred for 48 hours at 80° C. The solvent was evaporated, then $CH_2Cl_2$ and water were added. The separated organic layer was dried (MgSO$_4$), filtered and the solvent was evaporated. The product was taken up in $CH_3CN$, and the resulting precipitate filtered off and dried (vacuum), yielding 3.45 g (71%) of intermediate 64.

b) Preparation of Intermediate 65

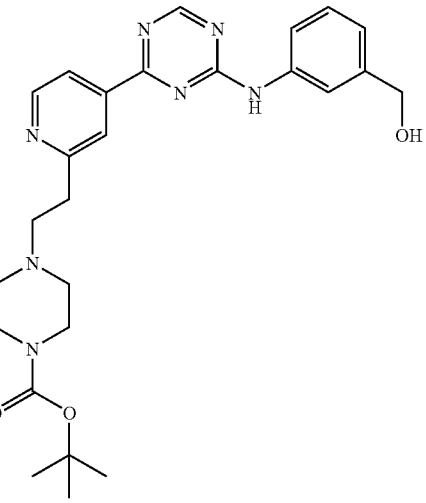

A mixture of intermediate 64 (0.00984 mol) and 1,1-dimethylethyl ester 1-piperazinecarboxylic acid (0.074 mol) was heated for 18 hours at 100° C. (melt). Next, the product was purified by column chromatography over silica gel (eluent: gradient 0 to 10% MeOH/$CH_2Cl_2$). The product fractions were collected and the solvent was evaporated. The residue was dissolved in $CH_2Cl_2$ and washed several times with $H_2O$ (3 L total). The separated organic layer was dried (MgSO$_4$), filtered and the solvent was evaporated. The product was further purified by column chromatography over silica gel (eluent: gradient $CH_2Cl_2$ to 10% MeOH/$CH_2Cl_2$). The product fractions were collected and the solvent was evaporated. The product was dissolved in $CH_2Cl_2$ and MP-NCO (0.010 mol) was added. The reaction mixture was stirred at room temperature for 1 hour. The scavenger was filtered off and the solvent was evaporated, yielding 1 g (20%) of intermediate 65.

c) Preparation of Intermediate 66

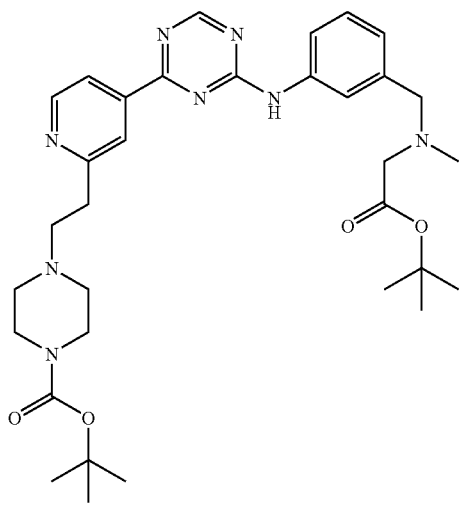 [SMILES: CN(CC(=O)OC(C)(C)C)Cc1cccc(Nc2ncnc(-c3ccnc(CCN4CCN(C(=O)OC(C)(C)C)CC4)c3)n2)c1]

DIPEA (0.014 mol) was added to a mixture of intermediate 65 (0.0010 mol) in DMF (50 ml). Then methanesulfonyl chloride (0.0031 mol) was added in small portions over 3 hours at room temperature. N-methyl-1,1-dimethylethyl ester glycine (0.003 mol) was added and the reaction mixture was stirred for 18 hours at 60° C. The mixture was cooled to room temperature and finally Macroporous benzyl isocyanate scavenger (0.006 mol) was added. The reaction mixture was stirred overnight at room temperature. The scavenger was filtered off and the solvent was evaporated. The residue was partitioned between $CH_2Cl_2$ and $H_2O$ and $Na_2CO_3$ was added. The separated organic layer was dried ($MgSO_4$), filtered and the solvent was evaporated, yielding 0.630 g (100%) of intermediate 66.

d) Preparation of Intermediate 67

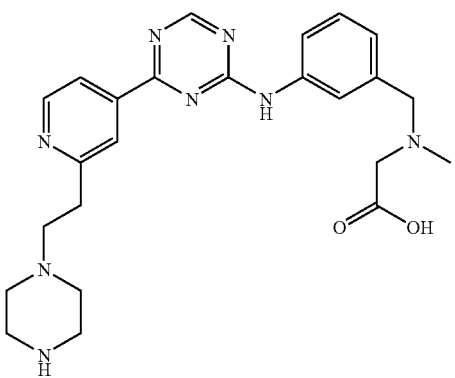 [SMILES: CN(CC(=O)O)Cc1cccc(Nc2ncnc(-c3ccnc(CCN4CCNCC4)c3)n2)c1]

A mixture of intermediate 66 (0.00102 mol) in a 50% TFA solution in $CH_2Cl_2$ (20 ml) was stirred overnight at room temperature. The solvent was evaporated and re-evaporated 2× with $CH_2Cl_2$, yielding intermediate 67 as a TFA salt (.$C_2HF_3O_2$, the product was used further without purification).

Example A20 a) Preparation of Intermediate 68

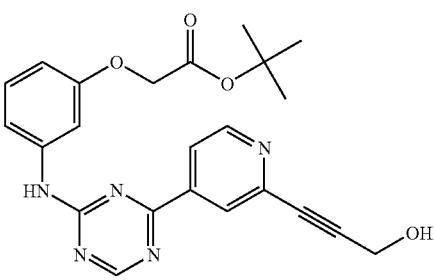 [SMILES: CC(C)(C)OC(=O)COc1cccc(Nc2ncnc(-c3ccnc(C#CCO)c3)n2)c1]

$N_2$ was bubbled for 5 minutes in a mixture of intermediate 53 (0.010 mol), 2-propyn-1-ol (0.015 mol), dichlorobis(triphenylphosphine)palladium (0.0005 mol), triphenylphosphine (0.002 mol) diethylamine (0.015 mol), and copper(I) iodide (0.0005 mol) in DMF (100 ml). The reaction mixture was stirred for 20 hours at 60° C. (nitrogen atmosphere). More 2-propyn-1-ol (0.015 mol) was added to the reaction mixture and stirred for 24 hours at 60° C. (nitrogen atmosphere). $H_2O$ (200 ml) and $CH_2Cl_2$ (200 ml) were added to the reaction mixture. The organic layer was separated and washed 2 times with brine. The separated organic layer was dried ($Na_2SO_4$), filtered and the solvent was evaporated. The residue was purified by flash column chromatography over silica gel (eluent: $CH_2Cl_2$/MeOH from 100/0 to 90/10). The product fractions were collected and the solvent was evaporated. The residue was stirred in $CH_3CN$ (60° C.) and activated carbon, then filtered over dicalite. The filtrate's solvent was evaporated and the residue was recrystallized from DIPE/$CH_3CN$. The precipitate was filtered off, yielding 1.033 g (24%; M.P.: 141.1° C. to 142.9° C.) of intermediate 68.

b) Preparation of Intermediate 69

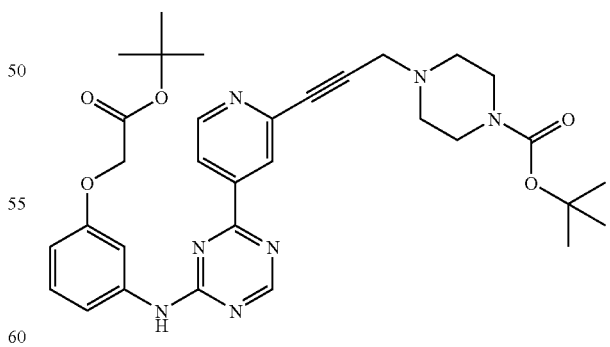

First DIPEA (0.006 mol), then methanesulfonyl chloride (0.0015 mol) were added to a solution of intermediate 68 (0.001 mol) in DMF (15 ml). The reaction mixture was stirred for 5 minutes and then 1,1-dimethylethyl ester 1-piperazinecarboxylic acid (0.0015 mol) was added. The reaction mixture was stirred for 22 hours at 65° C. The reaction mixture was cooled to room temperature and PS-NCO resin (0.001 mol) was added. The mixture was stirred overnight at room temperature, filtered and washed 4 times with DMF (5 ml). The filtrate's solvent was evaporated, yielding (crude used as such in next reaction step) intermediate 69.

c) Preparation of Intermediate 70

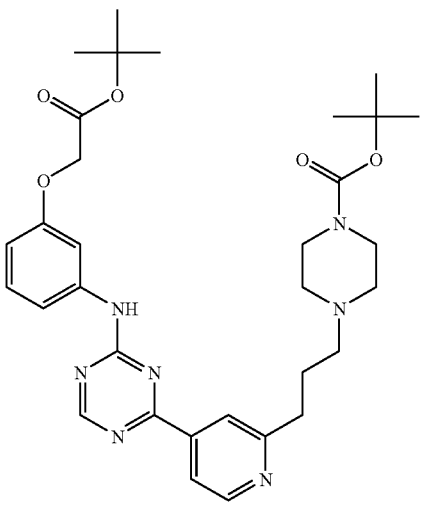 [SMILES: CC(C)(C)OC(=O)COc1cccc(Nc2ncnc(-c3ccnc(CCCN4CCN(C(=O)OC(C)(C)C)CC4)c3)n2)c1]

A mixture of crude intermediate 69 (0.001 mol) in THF (50 ml) was hydrogenated with Raney Nickel (catalytic quantities) as a catalyst. After an uptake of $H_2$ (2 equiv; 50 ml), the catalyst was filtered off. The filtrate's solvent was evaporated. The residue was purified by flash column chromatography over silica gel (eluent: $CH_2Cl_2$/MeOH from 100/0 to 90/10). The product fractions were collected and the solvent was evaporated, yielding 0.320 g (53%) of intermediate 70.

d) Preparation of Intermediate 71

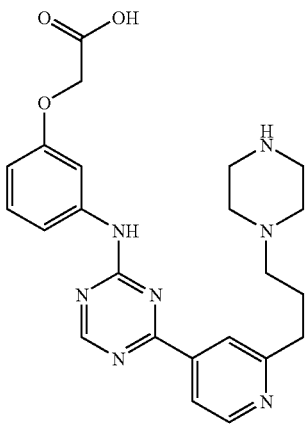 [SMILES: O=C(O)COc1cccc(Nc2ncnc(-c3ccnc(CCCN4CCNCC4)c3)n2)c1]

Intermediate 70 (0.00053 mol) was dissolved in a mixture of TFA/$CH_2Cl_2$/TIS (49/49/2, 20 ml) and stirred for 3 hours at room temperature. The solvent was evaporated, yielding (crude used as such in next reaction step) intermediate 71 as a TFA salt (.$C_2HF_3O_2$).

Example A21 a) Preparation of Intermediate 72

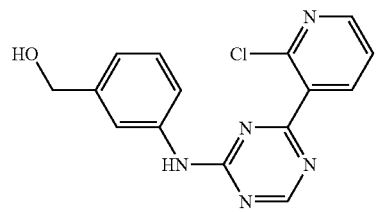 [SMILES: OCc1cccc(Nc2ncnc(-c3cccnc3Cl)n2)c1]

DIPEA (10 ml) was added at room temperature to a mixture of 2-chloro-4-(2-chloro-3-pyridinyl)-1,3,5-triazine (0.0142 mol) and 3-aminobenzenemethanol (0.0142 mol) in $CHCl_3$ (100 ml) and stirred overnight at room temperature. The precipitate was filtered off and the filter residue was dried, yielding 2.54 g (58%) of intermediate 72.

b) Preparation of Intermediate 73

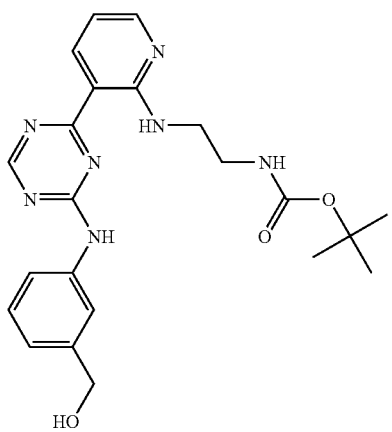 [SMILES: CC(C)(C)OC(=O)NCCNc1ncccc1-c1ncnc(Nc2cccc(CO)c2)n1]

A mixture of intermediate 72 (0.0159 mol), (2-aminoethyl)-1,1-dimethylethyl ester carbamic acid (0.047 mol) and DIPEA (10 ml) in $CH_3CN$ (50 ml) was heated in a microwave at 120° C. for 2 hours. The reaction mixture was cooled to room temperature. The solvent was evaporated. The residue was partitioned between $H_2O$ (50 ml) and EtOAc (150 ml). The separated organic layer was washed with $H_2O$ (20 ml) and then washed with brine (20 ml). This separated organic layer was dried ($Na_2SO_4$), filtered and the solvent was evaporated. The residue was dissolved in $CH_3CN$ at 45° C. Then the mixture was cooled to room temperature. The precipitate was filtered off and dried (vacuo), yielding 3.9 g (56%) of intermediate 73.

c) Preparation of Intermediate 74

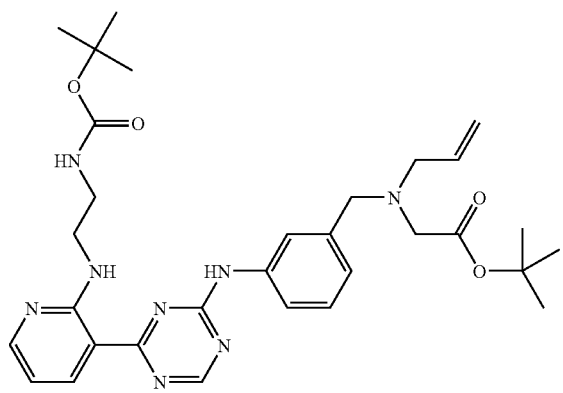 [SMILES: C=CCN(CC(=O)OC(C)(C)C)Cc1cccc(Nc2ncnc(-c3cccnc3NCCNC(=O)OC(C)(C)C)n2)c1]

Methanesulfonyl chloride (0.00086 mol) was added dropwise at room temperature to a mixture of intermediate 73 (0.00057 mol) and DIPEA (0.00342 mol) in DMF (7 ml). Then N-2-propenyl-1,1-dimethylethyl ester glycine (0.0014 mol) was added and the reaction mixture was stirred overnight at 70° C. Macroporous benzyl isocyanate scavenger (0.0025 mmol) was added and the reaction mixture was shaken overnight. The reaction mixture was filtered and the filtrate's solvent was evaporated (vacuo), yielding (crude used as such in next reaction step) intermediate 74.

d) Preparation of Intermediate 75

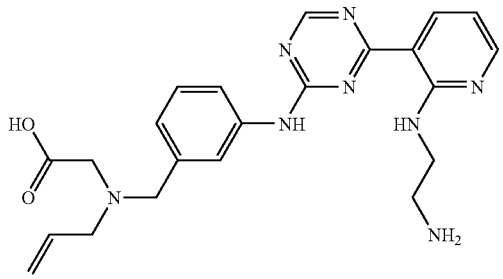 [SMILES: C=CCN(CC(=O)O)Cc1cccc(Nc2ncnc(-c3cccnc3NCCN)n2)c1]

Crude intermediate 74 (0.00057 mol) was dissolved at room temperature in CH$_2$Cl$_2$/TFA/TIS (49/49/2, 50 ml). The reaction mixture was stirred until all the intermediate 74 was consumed. The solvent was evaporated (vacuo), yielding (crude used as such in next reaction step) intermediate 75 as a TFA salt (.C$_2$HF$_3$O$_2$).

Example A22 a) Preparation of Intermediate 76

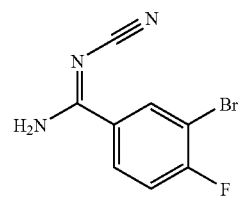 [SMILES: N#C/N=C(/N)c1ccc(F)c(Br)c1]

NaOCH$_3$ (0.1 equiv, 0.005 mol) was added to a solution of 3-bromo-4-fluorobenzonitrile (0.050 mol) in MeOH (50 ml). The mixture was stirred for 4 hours at room temperature. Cyanamide (1.5 equiv, 0.075 mol) was added and the reaction mixture was stirred overnight at room temperature. CH$_2$Cl$_2$ and brine were added. The organic layer was separated, washed with brine, dried (anhydrous MgSO$_4$), filtered and the solvent was evaporated. The residue was dried (vacuum, room temperature), yielding 10.51 g (87%; white solid) of intermediate 76.

b) Preparation of Intermediate 77

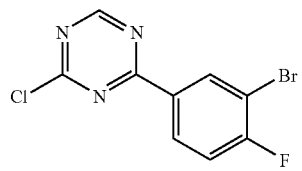 [SMILES: Fc1ccc(-c2ncnc(Cl)n2)cc1Br]

N-(chloromethylene)-N-methyl-methanaminium chloride (0.0335 mol) was added to a solution of intermediate 76 (0.0237 mol) in CH$_3$CN (50 ml). After 5 minutes of stirring, the mixture became homogeneous and in 30 minutes precipitation appeared. The reaction mixture was stirred for one additional hour. The reaction was quenched by adding a saturated aqueous NaHCO$_3$ solution. The layers were separated. The aqueous phase was extracted with CH$_2$Cl$_2$ (3×50 ml). The separated organic layer was dried (MgSO$_4$), filtered and c) Preparation of Intermediate 78

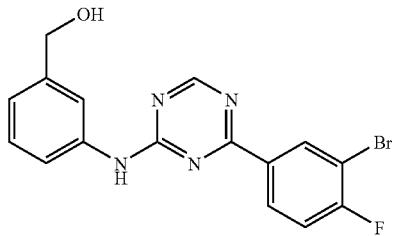 [SMILES: OCc1cccc(Nc2ncnc(-c3ccc(F)c(Br)c3)n2)c1]

3-Amino-benzenemethanol (0.0154 mol) was added in one portion to a solution of intermediate 77 (0.0128 mol) in 1,4-dioxane (65 ml). DIPEA (0.0154 mol) was added. The resultant reaction mixture was stirred for 5 hours at room temperature. $CH_2Cl_2$ (50 ml) and water (50 ml) were added. The layers were separated The aqueous phase was extracted with $CH_2Cl_2$. The organic layers were combined, dried ($MgSO_4$), filtered and the solvent was evaporated, yielding (used as such in next step) intermediate 78.

d) Preparation of Intermediate 79

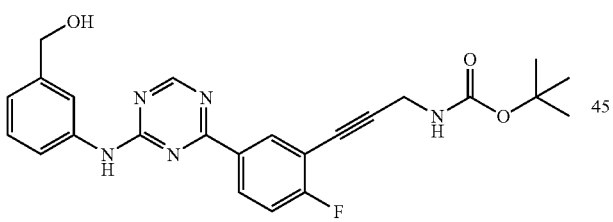

Reaction under $N_2$ atmosphere. A mixture of intermediate 78 (0.032 mol), 2-propynyl-1,1-dimethylethyl ester carbamic acid (0.080 mol), dichlorobis(triphenylphosphine)palladium (0.0032 mol), copper(I) iodide (0.0032 mol) and triphenylphosphine (0.0127 mol) in DMF (385 ml) was stirred and $N_2$ gas was allowed to bubble through for 10 minutes. Diethylamine (0.480 mol) was added and the resultant reaction mixture was stirred for 18 hours at 60° C. (nitrogen atmosphere). $CH_2Cl_2$ (50 ml) was added. The mixture was washed with brine. The brine phase was extracted with $CH_2Cl_2$ (3×50 ml). The organic layers were combined, dried ($MgSO_4$), filtered and the solvent was evaporated. The residue was dried (vacuum, room temperature), yielding 4.1 g (28%) of intermediate 79.

e) Preparation of Intermediate 80

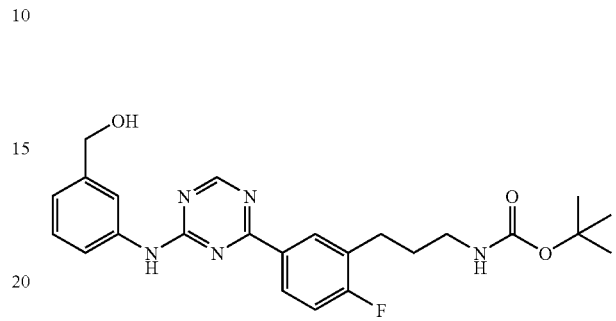

$Et_3N$ (0.0127 mol) was added to a solution of intermediate 79 (0.0091 mol) in THF (140 ml) and this mixture was hydrogenated for 48 hours at room temperature with Pt/C 10% (2 g) as a catalyst. After uptake of $H_2$ stopped, the catalyst was filtered off over a bed of Celite. The filtrate's solvent was evaporated and the residue was dried. The above procedure was repeated twice to effect complete reduction. The thus obtained residue was triturated with DIPE, the resulting precipitate filtered off, washed with DIPE, then dried, yielding 1.88 g (46%) of intermediate 80.

Example A23 a) Preparation of Intermediate 81

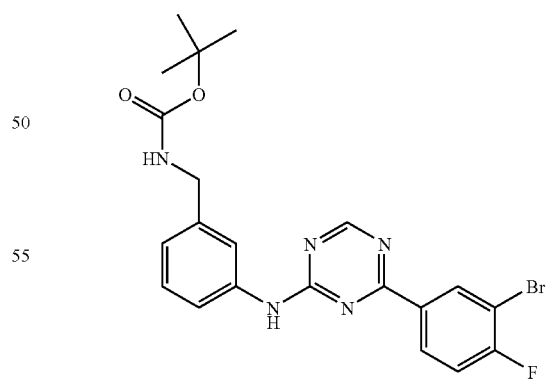

[(3-aminophenyl)methyl]-1,1-dimethylethyl ester carbamic acid (0.0286 mol) was added in one portion to a solution of intermediate 77 (0.0238 mol) in 1,4-dioxane (120 ml). DIPEA (0.0286 mol) was added. The resultant reaction mixture was stirred for 15 hours at room temperature. $CH_2Cl_2$ and brine were added. The layers were separated The organic layer was washed with brine, dried (MgSO$_4$), filtered and the solvent was evaporated. The residue was dried, yielding (47%) intermediate 81.

b) Preparation of Intermediate 82

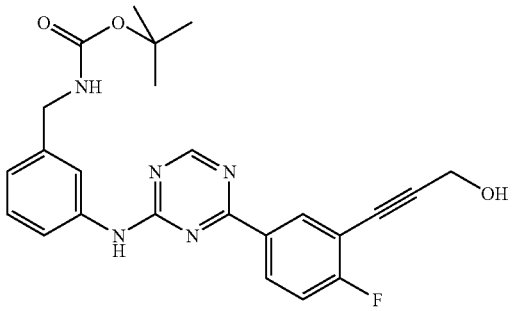 [SMILES: CC(C)(C)OC(=O)NCc1cccc(Nc2ncnc(-c3ccc(F)c(C#CCO)c3)n2)c1]

Reaction under N$_2$ atmosphere. A mixture of intermediate 81 (0.0111 mol), 2-propyn-1-ol (0.028 mol), dichlorobis(triphenylphosphine)palladium (0.00111 mol), copper(I) iodide (0.000111 mol) and triphenylphosphine (0.00447 mol) in DMF (135 ml) was stirred and N$_2$ gas was allowed to bubble through for 10 minutes. diethylamine (0.168 mol) was added and the resultant reaction mixture was stirred for 18 hours at 60° C. (nitrogen atmosphere). CH$_2$Cl$_2$ (100 ml) was added. Brine (50 ml) was added. The organic phase was washed with brine (3×50 ml). The organic layers were combined, dried (MgSO$_4$), filtered and the solvent was evaporated. The residue was purified by flash column chromatography over silica gel (eluent: gradient hexane/EtOAc 5/1 to 1/3). The product fractions were collected and the solvent was evaporated. The residue was triturated with DIPE, the resulting precipitate filtered off, washed with DIPE, then dried (vacuum, room temperature), yielding 1.36 g (27%) of intermediate 82.

Example A24 a) Preparation of Intermediate 83

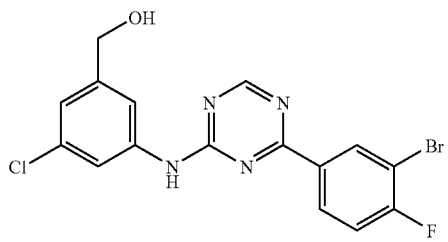 [SMILES: OCc1cc(Cl)cc(Nc2ncnc(-c3ccc(F)c(Br)c3)n2)c1]

3-Amino-5-chloro-benzenemethanol (0.0194 mol) was added in one portion to a solution of intermediate 77 (0.0162 mol) in 1,4-dioxane (80 ml). DIPEA (0.0194 mol) was added. The resultant reaction mixture was stirred for 8 hours at room temperature. CH$_2$Cl$_2$ (50 ml) and brine (50 ml) were added. The layers were separated. The organic layer was washed with brine (2×20 ml). The organic layers were combined, dried (MgSO$_4$), filtered and the solvent was evaporated, yielding 6 g (90%) of intermediate 83.

b) Preparation of Intermediate 84

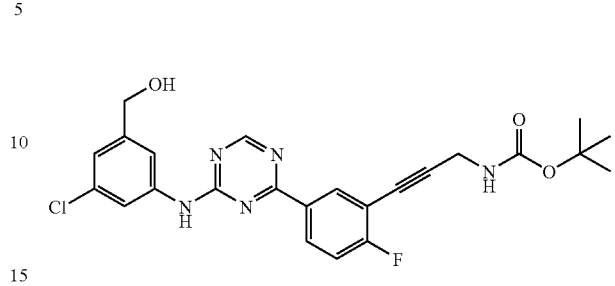

A mixture of intermediate 83 (0.0107 mol), 2-propynyl-1,1-dimethylethyl ester carbamic acid (0.0267 mol), dichlorobis(triphenylphosphine)palladium (0.00107 mol), copper(I) iodide (0.00107 mol) and triphenylphosphine (0.00428 mol) in DMF (130 ml) was stirred and N$_2$ gas was allowed to bubble through for 10 minutes. diethylamine (0.160 mol) was added and the resultant reaction mixture was stirred for 15 hours at 60° C. (nitrogen atmosphere). CH$_2$Cl$_2$ (100 ml) was added and this solution was washed with brine (3×50 ml). The organic layers were combined, dried (MgSO$_4$), filtered and the solvent was evaporated. The residue was purified by flash column chromatography over silica gel (eluent: gradient hexane/EtOAc from 5/1 to 1/1). The product fractions were collected and the solvent was evaporated. The residue was dried (vacuum, room temperature), yielding 4.16 g (80%) of intermediate 84.

c) Preparation of Intermediate 85

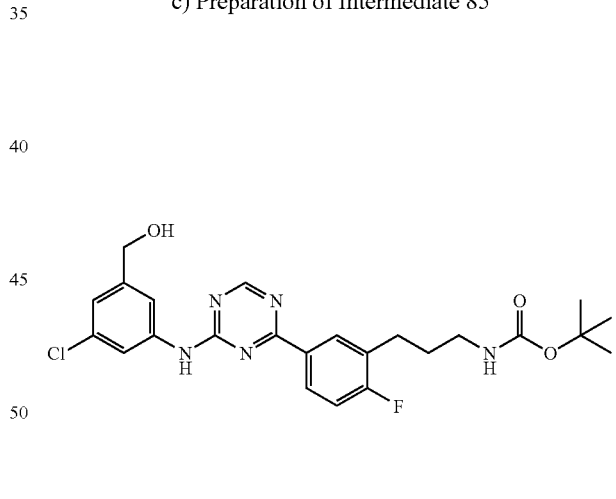

Et$_3$N (0.012 mol) was added to a solution of intermediate 84 (0.0086 mol) in THF (130 ml) and this mixture was hydrogenated for 12 hours at room temperature with Pt/C 5% (0.832 g) as a catalyst. The catalyst was filtered off over a bed of Celite. The Celite was washed with THF and the filtrate's solvent was evaporated and the residue was dried. This procedure was repeated (same quantities of all products). After uptake of H$_2$ stopped, the catalyst was filtered off over a bed of Celite. The Celite was washed with THF and the filtrate's solvent was evaporated under reduced pressure. The procedure was repeated again (3×). The residue was triturated

Example A25 a) Preparation of Intermediate 86

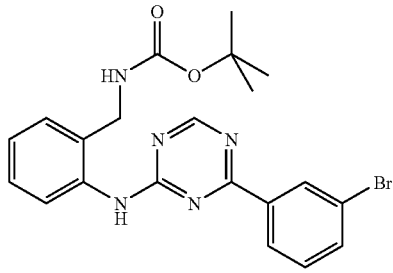 [SMILES: CC(C)(C)OC(=O)NCc1ccccc1Nc1ncnc(-c2cccc(Br)c2)n1]

[(2-aminophenyl)methyl]-1,1-dimethylethyl ester carbamic acid (0.031 mol) was added to a mixture of intermediate 32 (0.026 mol) in 1,4-dioxane (80 ml). DIPEA (0.052 mol) was added and the reaction mixture was stirred overnight. The reaction mixture was diluted with $CH_2Cl_2$ (200 ml), then washed with a saturated aqueous $NaHCO_3$ solution. The organic layer was separated, dried ($MgSO_4$), filtered and the solvent was evaporated, yielding 11.86 g of intermediate 86.

b) Preparation of Intermediate 87

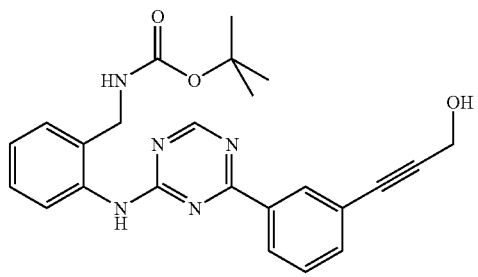 [SMILES: CC(C)(C)OC(=O)NCc1ccccc1Nc1ncnc(-c2cccc(C#CCO)c2)n1]

To a mixture of intermediate 86 (0.026 mol), copper(I) iodide (0.0026 mol), dichlorobis(triphenylphosphine)palladium (0.0026 mol) and triphenylphosphine (0.0052 mol), DMF (200 ml) was added and the mixture was stirred. Then, 2-propyn-1-ol (0.065 mol) and diethylamine (0.39 mol) were added. $N_2$ was bubbled through the mixture. The reaction mixture was stirred overnight at 60° C. (nitrogen atmosphere). More 2-propyn-1-ol (0.5 equiv), diethylamine (5 equiv), copper(I) iodide (0.10 equiv) and dichlorobis(triphenylphosphine)palladium (0.05 equiv) were added and the reaction mixture was stirred overnight at 60° C. (nitrogen atmosphere). Water (10 ml) was added. The solvent was evaporated. The residue was purified by column chromatography over silica gel (eluent: hexane/EtOAc 2/1). The product fractions were collected and the solvent was evaporated, yielding 10.2 g (91%) of intermediate 87.

c) Preparation of Intermediate 88

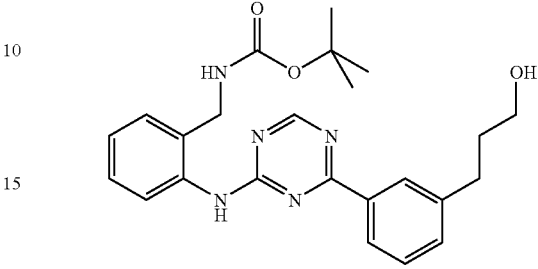

Intermediate 87 (0.00748 mol) was dissolved in $Et_3N$ (0.07485 mol) and MeOH (70 ml) under $N_2$. Pt/C 5% (2.92 g) was added and the reaction mixture hydrogenated (1 atm $H_2$) at room temperature for 24 hours. The reaction mixture was filtered over a pad of Celite and the filtrate's solvent was evaporated. The residue was taken up into $Et_3N$ (10.5 ml) and MeOH (70 ml) under $N_2$ atmosphere. Extra Pt/C 5% (2.92 g) was added and the reaction mixture was hydrogenated at room temperature for another 24 hours (1 atm $H_2$). The reaction mixture was filtered over a pad of Celite. The filtrate's solvent was evaporated. The residue was purified by flash column chromatography over silica gel (eluent: hexane/EtOAc 50/50). The product fractions were collected and the solvent was evaporated, yielding 2.11 g (65%) of intermediate 88.

d) Preparation of Intermediate 89

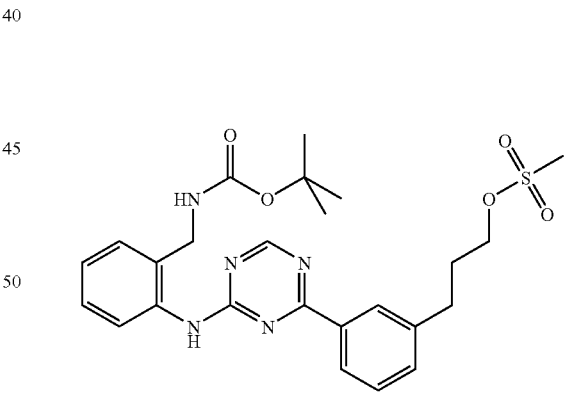

Intermediate 88 (0.00229 mol) was suspended in DIPEA (0.022 mol) and $CH_3CN$ (50 ml). A solution of methanesulfonyl chloride (0.00688 mol) in DMF (2 ml) was added. The reaction mixture was stirred for 30 minutes at room temperature. $CH_2Cl_2$ (100 ml) was added. The mixture was washed with a 1 M aqueous $Na_2CO_3$ solution (50 ml). The layers were separated. The organic layer was washed with water, dried ($MgSO_4$), filtered and the solvent was evaporated. The residue was purified by column chromatography over silica gel under DIPE, filtered off, washed with DIPE, then dried, yielding 3.26 g (78%) of intermediate 85.

(eluent: hexane/EtOAc 1/1). The product fractions were collected and the solvent was evaporated, yielding 0.870 g (75%) of intermediate 89.

e) Preparation of Intermediate 90

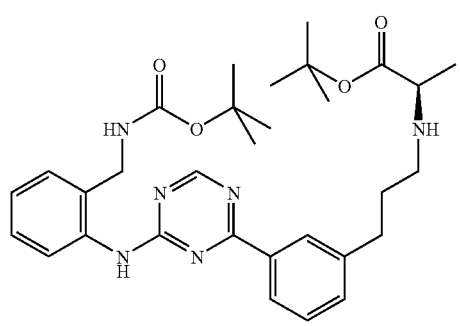 [SMILES: C[C@@H](NCCCc1cccc(-c2ncnc(Nc3ccccc3CNC(=O)OC(C)(C)C)n2)c1)C(=O)OC(C)(C)C]

Intermediate 89 (0.00021 mol) was dissolved in DMF (5 ml) and added to 1,1-dimethylethyl ester D-alanine and DIPEA (0.0015 mol) in 5 mL DMF. The resultant reaction mixture was stirred overnight at 65° C. After cooling PS-CHO (2.1 mmol/g) was added, the mixture was stirred at room temperature for 24 hours. The resins were removed by filtration, then washed with MeOH and with $CH_2Cl_2$/MeOH 4/1. The filtrate's solvent was evaporated, yielding intermediate 90 which was used in next reaction step, without further purification.

f) Preparation of Intermediate 91

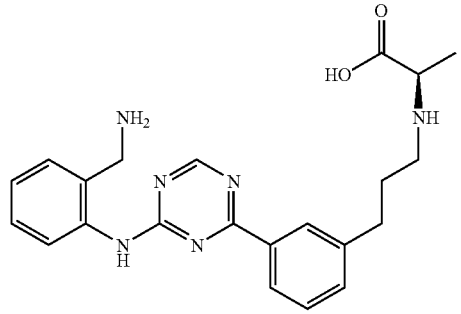 [SMILES: C[C@@H](NCCCc1cccc(-c2ncnc(Nc3ccccc3CN)n2)c1)C(=O)O]

Intermediate 90 (0.00025 mol; crude residue) was taken up in a mixture of TFA/TIS/$CH_2Cl_2$ (5 ml; 49/49/2). The reaction mixture was stirred overnight at room temperature. The solvent was evaporated, yielding crude intermediate 91 (TFA salt, used in next reaction step without further purification).

Example A26 a) Preparation of Intermediate 92

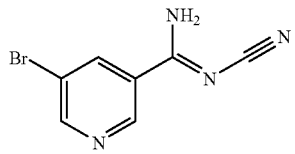 [SMILES: N#C/N=C(\N)c1cncc(Br)c1]

5-Bromo-3-pyridinecarbonitrile (0.002732 mol) was suspended in MeOH (3 ml). $NaOCH_3$ (0.0002732 mol) was added and the mixture was stirred for an hour at room temperature, and the mixture became homogeneous. $H_2N$—CN (0.004098 mol) was added and the resultant reaction mixture was stirred overnight at room temperature (after one hour, precipitation started). The resulting precipitate was filtered off, washed with diethyl ether (3×5 ml), and dried, yielding 0.513 g (83%, white solid) of intermediate 92.

b) Preparation of Intermediate 93

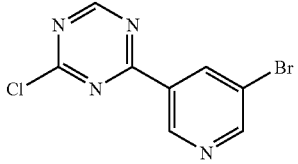 [SMILES: Clc1ncnc(-c2cncc(Br)c2)n1]

N-(chloromethylene)-N-methyl-methanaminium chloride (0.043 mol) was added to a mixture of intermediate 92 (0.028 mol) in $CH_3CN$. The mixture was stirred for 3 hours. 200 ml $CH_2Cl_2$ and 150 ml of a saturated aqueous $NaHCO_3$ soln. Phases were separated and the aqueous layer was extracted with $CH_2Cl_2$ (q.s.). The organic layer was dried ($MgSO_4$), filtered and dried, yielding 7.153 g (94%) of intermediate 93.

c) Preparation of Intermediate 94

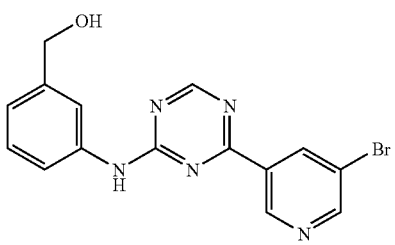 [SMILES: OCc1cccc(Nc2ncnc(-c3cncc(Br)c3)n2)c1]

DIPEA (0.4 mol) was added to a suspension of intermediate 93 (0.2 mol) and 3-aminobenzenemethanol (0.2 mol) in $CHCl_3$ (1000 ml) and stirred for 3 hours at 60° C. DIPE (1000 ml) and DIPEA (200 ml) were added to the stirring reaction mixture. The reaction mixture was cooled to room temperature and left stirring at room temperature over the weekend. $CH_2Cl_2$ (500 ml) and $Na_2CO_3$ 10% aqueous solution (500 ml)

were added. The precipitate was filtered off, washed with CH₂Cl₂ and H₂O (aqua destillata). The filter residue was crystallized from EtOH and the resulting precipitate was filtered off, yielding 20.14 g (28%) of intermediate 94.

d) Preparation of Intermediate 95

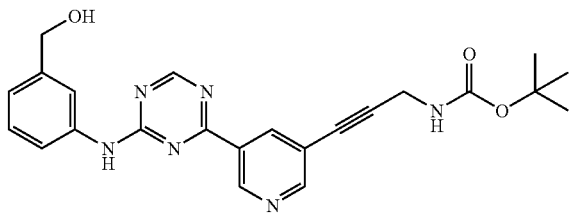 [SMILES: CC(C)(C)OC(=O)NCC#Cc1cncc(-c2ncnc(Nc3cccc(CO)c3)n2)c1]

N₂ was bubbled for 2 minutes through a mixture of intermediate 94 (0.015 mol), 2-propynyl-1,1-dimethylethyl ester carbamic acid (0.015 mol), diethylamine (0.015 mol), Pd(PPh₃)₄ (0.00075 mol) and copper(I) iodide (200 ml) in triphenylphosphine (0.0003 mol). The reaction mixture was stirred overnight at 75° C. The reaction mixture was filtered and the filtrate's solvent was evaporated. The residue was purified by column chromatography over silica gel. The product fractions were collected and the solvent was evaporated. The residue was recrystallized from CH₃CN, yielding 11.25 g (58%) of intermediate 95.

e) Preparation of Intermediate 96

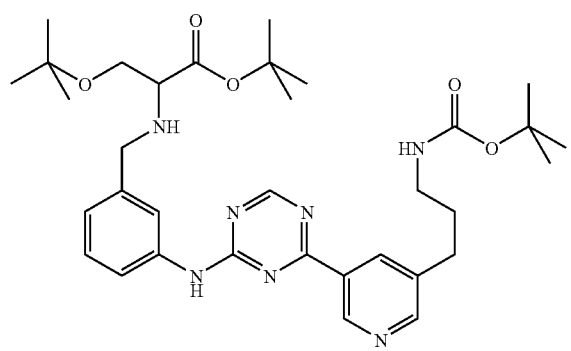 [SMILES: CC(C)(C)OCC(NCc1cccc(Nc2ncnc(-c3cncc(CCCNC(=O)OC(C)(C)C)c3)n2)c1)C(=O)OC(C)(C)C]

A mixture of intermediate 95 (0.032 mol) in MeOH (250 ml) was hydrogenated with Raney Nickel as a catalyst. After uptake of H₂ (q.s.), the catalyst was filtered off and the filtrate was evaporated. The residue, methanesulfonyl chloride (0.0384 mol) and DIPEA (0.192 mol) in DMF (150 ml) was stirred until the residue was consumed. Then [51537-21-4] (0.064 mol) was added and the reaction mixture was stirred overnight at 70° C. The solvent was evaporated. The residue was purified by column chromatography over silica gel. The product fractions were collected and the solvent was evapo-rated. The crude was used as such in next reaction step, yielding a racemic mixture as intermediate 96.

f) Preparation of Intermediate 97

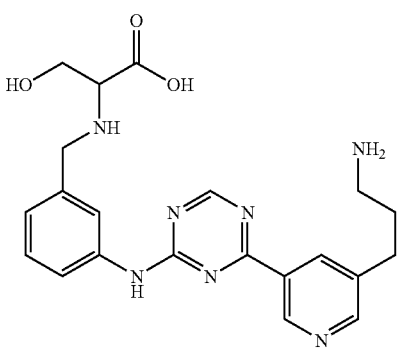 [SMILES: NCCCc1cncc(-c2ncnc(Nc3cccc(CNC(CO)C(=O)O)c3)n2)c1]

Intermediate 96 was added to TFA/CH₂Cl₂/TIS (49/49/2, 500 ml) and then stirred at 40° C. until the crude was consumed. The solvent was evaporated. The crude was used as such in a next reaction step, yielding a racemic mixture as intermediate 97 (TFA salt).

Example A27 a) Preparation of Intermediate 98

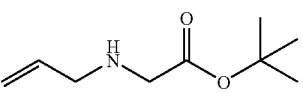

Bromo-1,1-dimethylethyl ester acetic acid (1 mol) dissolved in EtOH (500 ml) was added drop wise to an ice-cooled solution of 2-propen-1-amine (3 mol) and Et₃N (1 mol) in EtOH (1000 ml). The reaction mixture was allowed to warm to room temperature and stirred for 20 hours. The solvent was evaporated and the residue was redissolved in EtOAc. The mixture was re-extracted 2 times with 1N citric acid aqueous solution (500 ml). Na₂CO₃ was added portion wise to the combined separated aqueous layers until pH=10. This mixture was extracted 3 times with EtOAc (500 ml). The combined separated organic layers were dried (Na₂SO₄), filtered and the filtrate's solvent was evaporated. This residue was dissolved in hexane, the precipitate was filtered off and washed with hexane. The filtrate's solvent was evaporated and 1N HCl in 2-propanol (500 ml) was added while cooling on an ice bath. The solvent was partially evaporated and again 1N HCl in 2-propanol (1200 ml) was added while cooling on an ice bath. DIPE (1500 ml) was added to the mixture. The precipitate was filtered off and washed with DIPE, yielding 152.38 g (73%) of intermediate 98 as a hydrochloric acid salt (.HCl).

Example A28 a) Preparation of Intermediate 99

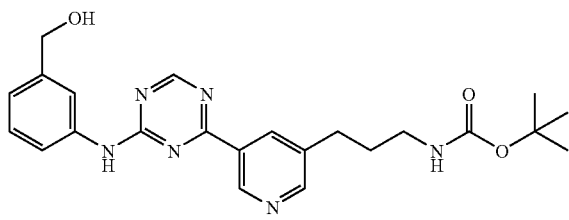 [SMILES: CC(C)(C)OC(=O)NCCCc1cncc(-c2ncnc(Nc3cccc(CO)c3)n2)c1]

Et$_3$N (0.152 mol) was added to a mixture of intermediate 95 (0.015 mol) in EtOH/MeOH (1/1, 75 ml). Pt/C 5% (3 g) was added under N$_2$ flow. The mixture was stirred during the weekend under H$_2$ atmosphere (1 atm). The precipitate was filtered, washed with MeOH (q.s.) and DMF (q.s.). The solvent was evaporated and the above procedure was repeated. The thus obtained residue was purified by column chromatography over silica gel (eluent: EtOAc). The product fractions were collected and the solvent was evaporated, yielding 5.05 g (75%) of intermediate 99.

b) Preparation of Intermediate 100

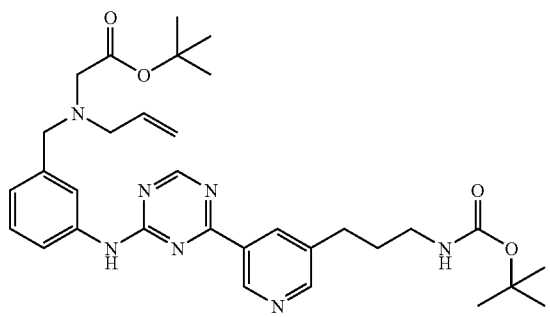 [SMILES: C=CCN(CC(=O)OC(C)(C)C)Cc1cccc(Nc2ncnc(-c3cncc(CCCNC(=O)OC(C)(C)C)c3)n2)c1]

DIPEA (0.012 mol) and then methanesulfonyl chloride (0.00309 mol) were added to a solution of intermediate 99 (0.00206 mol) in DMF (20 ml) and stirred for 5 minutes. Intermediate 98 (0.00619 mol) was added and the reaction mixture was stirred overnight at 65° C. The solvent was evaporated. The residue was dissolved in CH$_2$Cl$_2$ (20 ml). This mixture was washed 3 times with H$_2$O (10 ml) and then washed 2 times with NaHCO$_3$ saturated aqueous solution.

The separated organic layer was dried (Na$_2$SO$_4$), filtered and the solvent was evaporated, yielding intermediate 100 (used as such in next reaction step)

c) Preparation of Intermediate 101

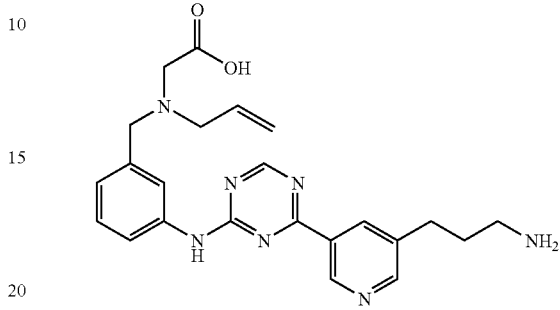

A solution of crude intermediate 100 (0.00206 mol) in TFA/CH$_2$Cl$_2$/TIS (49/49/2, 20 ml) was added shaken for 3 hours at 30° C. The solvent was evaporated. The residue was purified by reversed phase high-performance liquid chromatography (standard gradient elution with NH$_4$HCO$_3$ buffer). The product fractions were collected, the solvent was evaporated and co-evaporated with MeOH, yielding 1.57 g (used as such in next reaction step) of intermediate 101.

d) Preparation of Intermediate 102

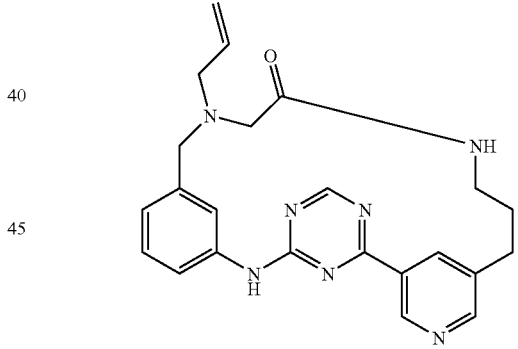

Crude intermediate 101 (0.00206 mol) dissolved in DMF (50 ml) was added drop wise to a solution of HBTU (0.00824 mol) and DIPEA (0.0412 mol) dissolved in DMF (100 ml). NH$_3$ in MeOH 7N (20 ml) was added and the reaction mixture stirred for 15 minutes at room temperature. The solvent was evaporated. The residue was dissolved in MeOH/CH$_2$Cl$_2$ (100 ml, 10/90). NaHCO$_3$ saturated aqueous solution and H$_2$O were added to the mixture and stirred over the weekend at room temperature. The aqueous layer was extracted 3 times with MeOH/CH$_2$Cl$_2$ (50 ml, 10/90) and the combined organic layers were dried (K$_2$CO$_3$ anhydrous), filtered and the solvent was evaporated. The residue was purified by flash column chromatography over silica gel (eluent: CH$_2$Cl$_2$/(7N NH$_3$ in MeOH)/MeOH) 90/5/5). The product fractions were collected and the solvent was evaporated. The residue was crystallized from MeOH, the precipitate was filtered off and dried

Example A29 a) Preparation of Intermediate 103

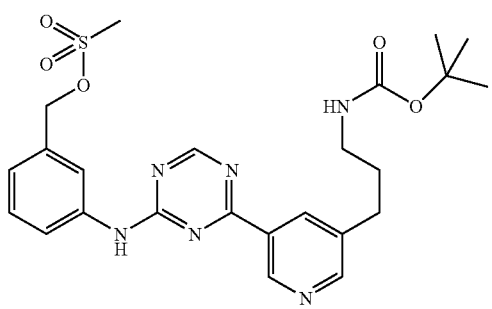 [SMILES: CC(C)(C)OC(=O)NCCCc1cncc(-c2ncnc(Nc3cccc(COS(C)(=O)=O)c3)n2)c1]

Intermediate 99 (0.00425 mol) and DIPEA (0.025 mol) were mixed in DMF (80 ml). Methanesulfonyl chloride (0.00673 mol) was added. The reaction mixture was stirred for 60 minutes at room temperature. The resultant solution was used in next reaction step as intermediate 103, without further purification.

b) Preparation of Intermediate 104

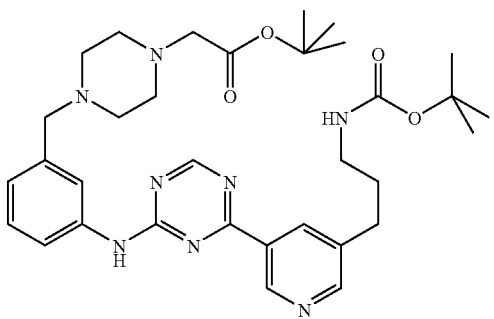 [SMILES: CC(C)(C)OC(=O)CN1CCN(Cc2cccc(Nc3ncnc(-c4cncc(CCCNC(=O)OC(C)(C)C)c4)n3)c2)CC1]

Crude intermediate 103 (max. 0.000250 mol) in DIPEA (max. 0.255 ml) and DMF (4.7 ml) was added to 1,1-dimethylethyl ester 1-piperazineacetic acid (0.0005 mol). The reaction solution was shaken for 24 hours at 65° C. The solvent was evaporated, yielding crude intermediate 104 (used in next reaction step, without further purification).

c) Preparation of Intermediate 105

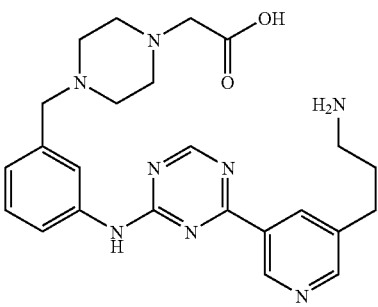 [SMILES: NCCCc1cncc(-c2ncnc(Nc3cccc(CN4CCN(CC(=O)O)CC4)c3)n2)c1]

Intermediate 104 (max. 0.00025 mol; crude residue) was taken up in a mixture of TFA/CH$_2$Cl$_2$/TIS (5 ml; 49/49/2). The reaction mixture was shaken for 24 hours at room temperature. The solvent was evaporated, yielding crude intermediate 105 (TFA salt, used in next reaction step without further purification).

Example A30 a) Preparation of Intermediate 106

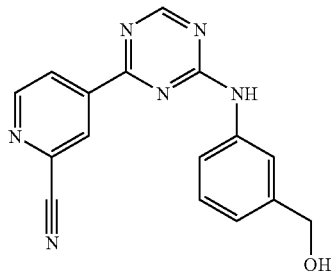 [SMILES: N#Cc1cc(-c2ncnc(Nc3cccc(CO)c3)n2)ccn1]

A mixture of intermediate 1 (0.015 mol), tris[μ-[(1,2-η:4,5-η)-(1E,4E)-1,5-diphenyl-1,4-pentadien-3-one]]di-palladium (0.015 mol), 1,1'-bis(diphenylphosphino)ferrocene (0.015 mol), Zn (catalytic quantity) and Zn(CN)$_2$ (200 ml) in DMA was heated for 2 hours at 80° C. in a microwave. The reaction mixture was poured into H$_2$O. This mixture was extracted with EtOAc. The separated organic layer was washed 3 times H$_2$O, dried (MgSO$_4$), filtered and the solvent was evaporated. The residue was suspended in CH$_3$CN. The b) Preparation of Intermediate 107

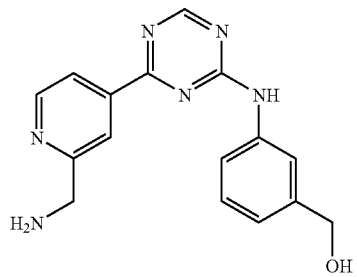 [SMILES: NCc1cc(-c2ncnc(Nc3cccc(CO)c3)n2)ccn1]

A mixture of intermediate 106 (0.0032 mol) in NH$_3$ in MeOH (100 ml) was hydrogenated with Raney Nickel (0.050 g) as a catalyst. After uptake of H$_2$ (2 equiv), the catalyst was filtered off over dicalite and the filtrate was evaporated, yielding 0.970 g (98%, crude was used as such in next reaction step without further purification) of intermediate 107.

c) Preparation of Intermediate 108

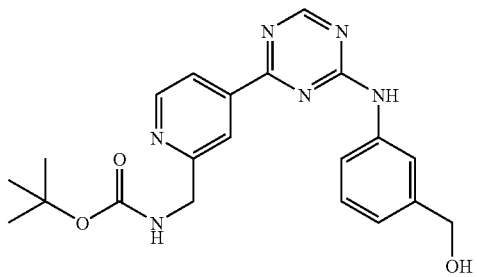 [SMILES: CC(C)(C)OC(=O)NCc1cc(-c2ncnc(Nc3cccc(CO)c3)n2)ccn1]

MeOH (10 ml) and then a 10% Na$_2$CO$_3$ aqueous solution (10 ml) were added to a mixture of intermediate 107 (0.0032 mol) in CH$_2$Cl$_2$ (30 ml). Bis(1,1-dimethylethyl)ester dicarbonic acid (0.0042 mol) in CH$_2$Cl$_2$ (10 ml) was added drop wise to the reaction mixture and stirred for 1 hour at room temperature. CH$_2$Cl$_2$ and H$_2$O were added to the reaction mixture. After extraction, the separated organic layer was dried (MgSO$_4$), filtered and the solvent was evaporated, yielding 0.74 g (57%; M.P.: 167° C. to 169° C.) of intermediate 108.

d) Preparation of Intermediate 109

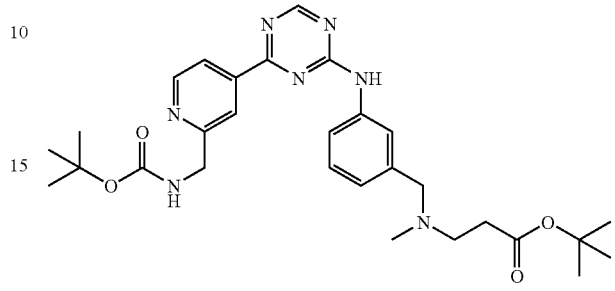

DIPEA (0.0086 mol) was added to a mixture of intermediate 108 (0.00086 mol) in extra dry DMF (50 ml). Methanesulfonyl chloride (0.00325 mol) was added portion wise over 3 hours to the reaction mixture. N-methyl-1,1-dimethylethyl ester β-alanine hydrochloride (0.00258 mol) was added to the reaction mixture and stirred for 24 hours at 60° C. The solvent was evaporated. The concentrate was washed with H$_2$O and then washed 2 times with Na$_2$CO$_3$ 5% aqueous solution. The separated organic layer was dried (MgSO$_4$), filtered and the solvent was evaporated, yielding 0.490 g (crude was used as such in next reaction step without further purification) of intermediate 109.

e) Preparation of Intermediate 110

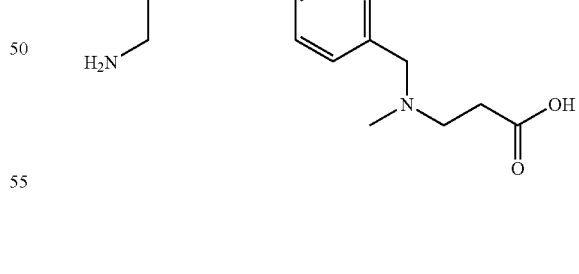

Intermediate 109 (0.00086 mol, crude) in a 50% TFA in CH$_2$Cl$_2$ solution (40 ml) was stirred overnight at room temperature. The solvent was evaporated and co-evaporated 2 times with CH$_3$CN. The residue was purified by reversed-phase high-performance liquid chromatography (standard gradient elution with NH$_4$HCO$_3$ buffer). The product frac- Example A31 a) Preparation of Intermediate 111

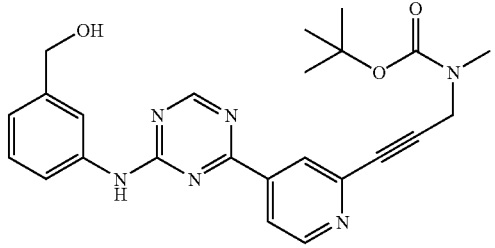 [SMILES: CN(CC#Cc1cc(-c2ncnc(Nc3cccc(CO)c3)n2)ccn1)C(=O)OC(C)(C)C]

A solution of intermediate 1 (0.0125 mol), methyl-2-propynyl-1,1-dimethylethyl ester carbamic acid (0.01875 mol), diethylamine (0.1875 mol), dichlorobis(triphenylphosphine)palladium (0.000625 mol), copper(I) iodide (0.000625 mol) and triphenylphosphine (0.0025 mol) in DMF (125 ml) was prepared. $N_2$-gas was bubbled through the solution for 5 minutes while stirring and then the solution was stirred overnight at 60° C. (nitrogen atmosphere). Then $H_2O$ (10 ml) was added and the solvent was evaporated till dryness. The residue was purified by flash column chromatography (eluent: $CH_2Cl_2$/EtOAc from 100/0 to 0/100). The product fractions were collected and the solvent was evaporated. The residue was dissolved in $CH_3CN$ and the solution was stirred during the weekend (yellow precipitate). The precipitate was filtered off, washed with $CH_3CN$ and dried, yielding 4.25 g (76%) of intermediate 111.

b) Preparation of Intermediate 112

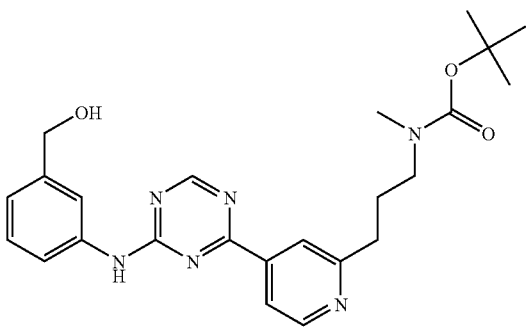 [SMILES: CN(CCCc1cc(-c2ncnc(Nc3cccc(CO)c3)n2)ccn1)C(=O)OC(C)(C)C]

A mixture of intermediate 111 (0.00951 mol) in MeOH (250 ml) was hydrogenated at 50° C. with Pt/C 5% (0.5 g) as a catalyst. After 2 days (uptake of 2 equiv $H_2$), the catalyst was filtered off and the filtrate was evaporated. The mixture was evaporated till dryness and the residue was washed with hexane and dried (vacuum). The residue was dissolved in $CH_3CN$ and the solution was cooled overnight to 0° C. The resulting yellow precipitate was filtered off, yielding 3.9154 g (91%; M.P.: 89.3-91.7° C.). of intermediate 112.

Example A32 a) Preparation of Intermediate 113

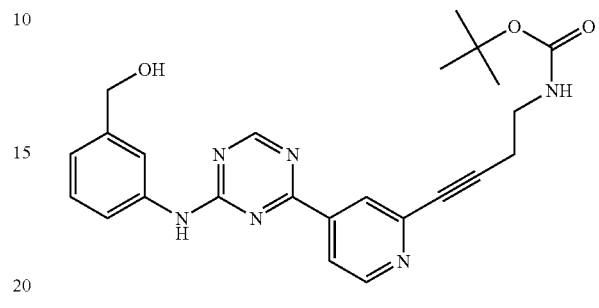

A solution of intermediate 1 (0.0125 mol), 3-butynyl-1,1-dimethylethyl ester carbamic acid (0.01875 mol), diethylamine (0.1875 mol), dichlorobis(triphenylphosphine)palladium (0.000625 mol), copper(I) iodide (0.000625 mol) and triphenylphosphine (0.0025 mol) in DMF (125 ml) was prepared. $N_2$-gas was bubbled through the solution for 5 minutes while stirring and then the solution was stirred overnight at 60° C. (nitrogen atmosphere). Then more 3-butynyl-1,1-dimethylethyl ester carbamic acid (0.001875 mol) was added and the solution was continued stirring at 60° C. (nitrogen atmosphere). Then $H_2O$ (20 ml) was added and the solvent was evaporated till dryness. The residue was triturated over the weekend with MeOH. The precipitate was filtered off (yellow powder), yielding 2.19 g (LCMS: 94% P) of intermediate 113. The solvent of the filtrate was also evaporated and the residue was purified by flash chromatography (eluent: $CH_2Cl_2$/EtOAc from 100/0 to 0/100). The product fractions were collected and the solvent was evaporated. $CH_3CN$ was added to the residue and the mixture was triturated overnight (yellow precipitate). The precipitate was filtered off, yielding another 3.35 g of intermediate 113 (total yield: 99%, M.P. 159.4-160.3° C.).

b) Preparation of Intermediate 114

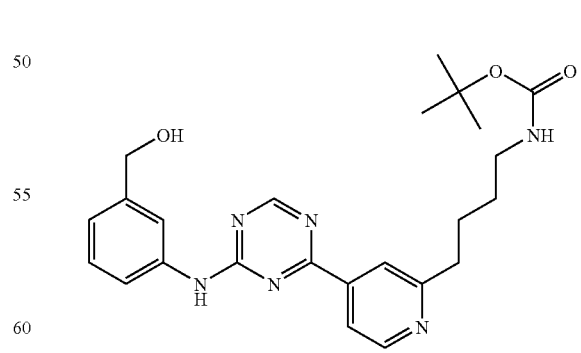

A mixture of intermediate 113 (0.0075 mol) in MeOH (150 ml) was hydrogenated with Pt/C 5% (1 g) as a catalyst in the presence of $H_2$ (375 ml). After 2 days, the catalyst was filtered off and the filtrate was evaporated. $CH_3CN$ was added and this solution was stirred at room temperature. After 24 hours a white precipitate was filtered off and dried, yielding 2.7122 g (80%; white solid; M.P.: 137.3-138.7° C.) of intermediate 114.

B. PREPARATION OF THE COMPOUNDS

Example B1

Preparation of Compounds 1 and 2

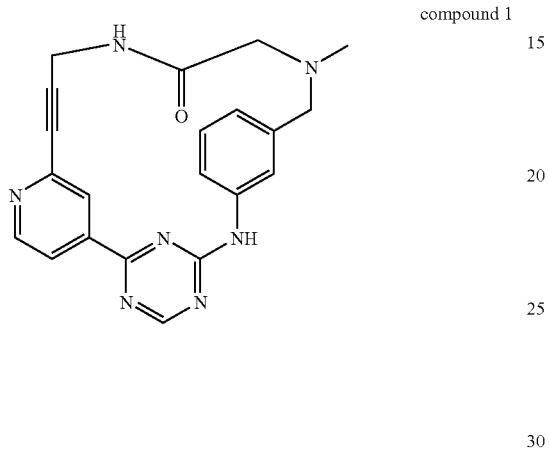

compound 1

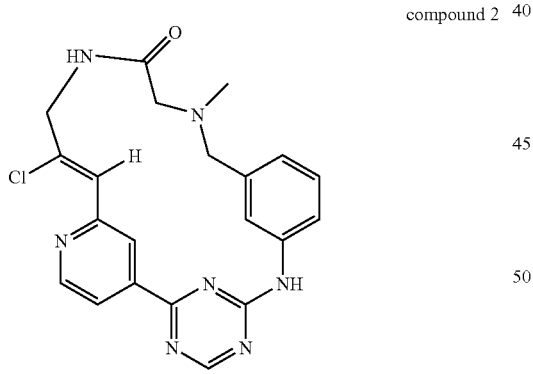

compound 2

To a mixture of crude intermediates 4a and 4b (ratio 70:30 according to LCMS, 0.00075 mol in total) in DMF (20 ml), DIPEA (0.018 mol) was added. This solution was added dropwise to a mixture of HBTU (0.00225 mol) in DMF (10 ml). The solvent was evaporated. A mixture of water and a saturated aqueous sodium carbonate solution (50/50) was added. The mixture was extracted with MeOH/CH$_2$Cl$_2$ (10/90). The organic phase was separated, dried (anhydrous potassium carbonate), filtered and the solvent was evaporated. The residue was purified by reversed-phase high-performance liquid chromatography (ammonium acetate-buffer) providing 0.0038 g of compound 1 (LCMS: 99% P; M.P.: 267.5-269.3° C.) and 0.0031 g of compound 2 (LCMS: 99% P; NMR: (Z)-geometry confirmed).

Example B2

Preparation of Compound 3

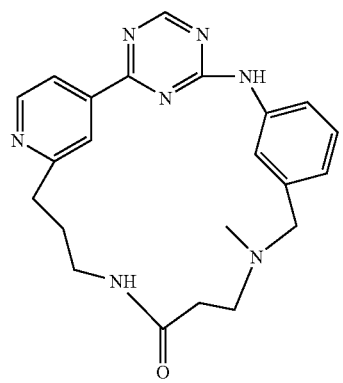 [SMILES: CN1CCC(=O)NCCCc2cc(ccn2)-c2ncnc(n2)Nc2cccc(c2)C1]

DIPEA (10-30 equiv) was added to a solution of intermediate 7 (0.00025 mol) in DMF (10 ml). The solution was added dropwise to HBTU (3 equiv) in DMF (10 ml). Next, the solvent was evaporated and the residue purified by reversed-phase high-performance liquid chromatography (ammonium acetate-buffer) and desalted with TFA buffer, yielding 0.011 g of compound 3 as a TFA salt (.C$_2$HF$_3$O$_2$).

Table F-2 lists the compounds that were prepared according to the above Example. The following abbreviations were used in the tables: .C$_2$HF$_3$O$_2$ stands for the trifluoroacetate salt, .HCl stands for hydrochloric acid salt.

TABLE F-2

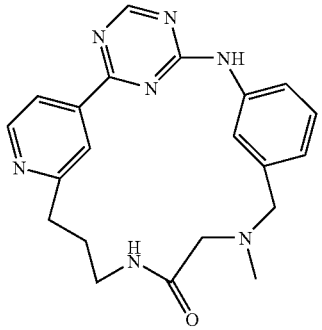 [SMILES: CN1CC(=O)NCCCc2cc(ccn2)-c2ncnc(n2)Nc2cccc(c2)C1]

Co. No. 10; •C$_2$HF$_3$O$_2$; M.P.: 257.3-258.9° C.

TABLE F-2-continued
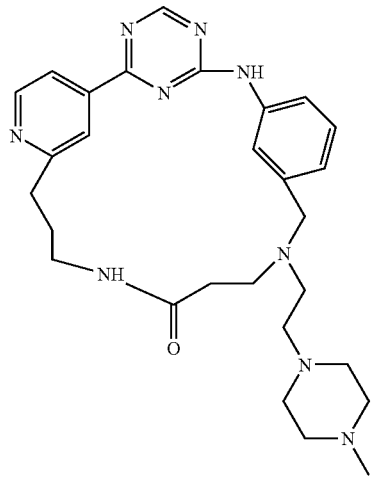 [SMILES: CN1CCN(CCN2CCC(=O)NCCCc3cc(ccn3)-c3ncnc(n3)Nc3cccc(c3)C2)CC1]
Co. No. 11; •C₂HF₃O₂
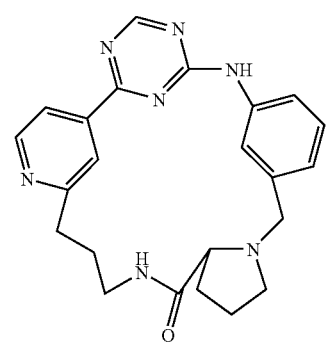 [SMILES: O=C1NCCCc2cc(ccn2)-c2ncnc(n2)Nc2cccc(c2)CN2CCCC12]
Co. No. 12; •C₂HF₃O₂
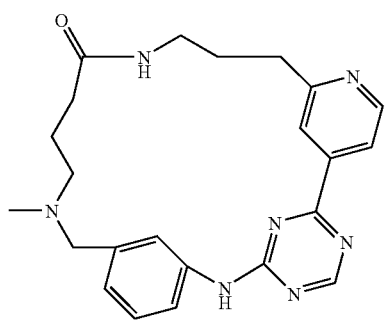 [SMILES: CN1CCCC(=O)NCCCc2cc(ccn2)-c2ncnc(n2)Nc2cccc(c2)C1]
Co. No. 13; •C₂HF₃O₂
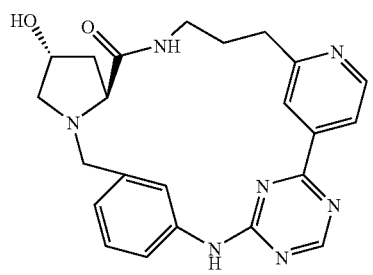 [SMILES: O=C1NCCCc2cc(ccn2)-c2ncnc(n2)Nc2cccc(c2)CN2C[C@H](O)C[C@@H]12]
Co. No. 14; •C₂HF₃O₂
TABLE F-2-continued
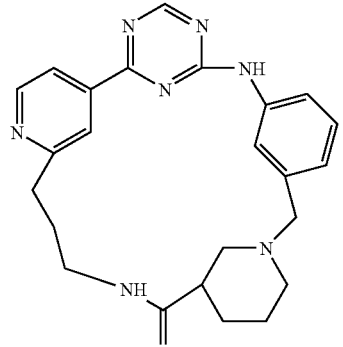
Co. No. 15; •C₂HF₃O₂
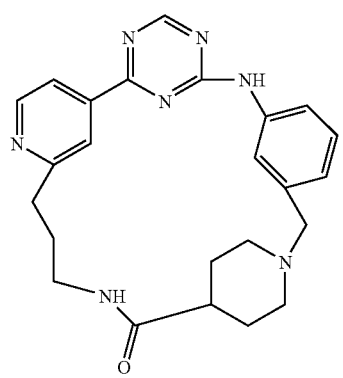 [SMILES: O=C1NCCCc2cc(ccn2)-c2ncnc(n2)Nc2cccc(c2)CN2CCC1CC2]
Co. No. 16; •C₂HF₃O₂
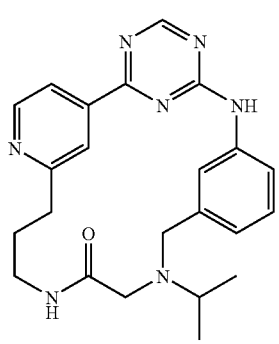 [SMILES: CC(C)N1CC(=O)NCCCc2cc(ccn2)-c2ncnc(n2)Nc2cccc(c2)C1]
Co. No. 65
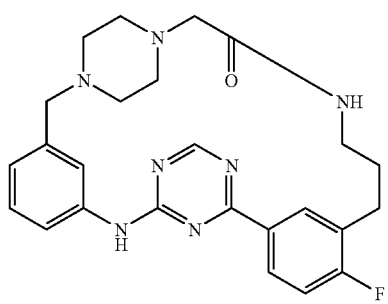 [SMILES: O=C1CN2CCN(CC2)Cc2cccc(c2)Nc2ncnc(n2)-c2ccc(F)c(c2)CCCN1]
Co. No. 66 (from Int. 7a)

TABLE F-2-continued

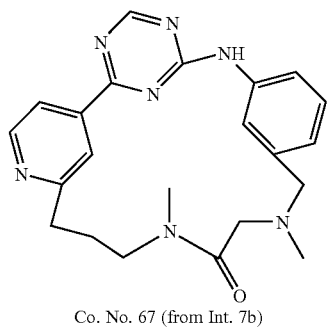

Co. No. 67 (from Int. 7b)

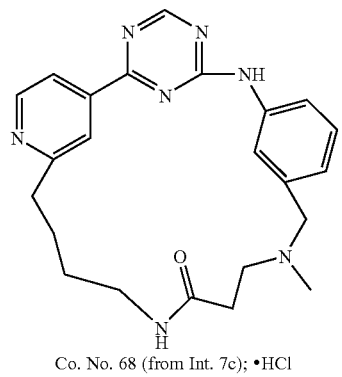

Co. No. 68 (from Int. 7c); •HCl

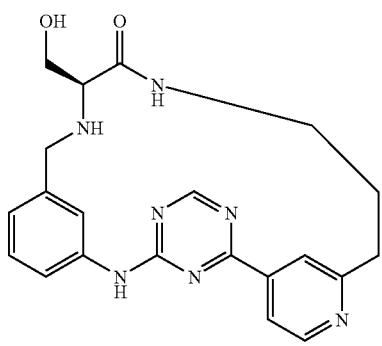 [SMILES: O=C1NCCCc2cc(ccn2)-c2ncnc(n2)Nc2cccc(c2)CN[C@H]1CO]

Co. No. 69

Example B3

Preparation of Compound 4

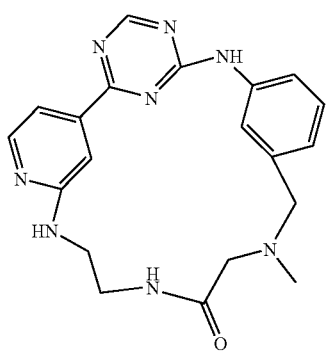 [SMILES: CC(=O)CN(C)Cc1cccc(Nc2ncnc(-c3ccnc(NCCN)c3)n2)c1]

A solution of intermediate 12 (0.000125 mol) in DMF (10 ml) was added dropwise to a solution of HBTU (3 equiv) and DIPEA (30 equiv) in DMF (10 ml). Next, the solvent was evaporated and the residue purified by reversed-phase high-performance liquid chromatography (ammonium acetate-buffer) and desalted with TFA buffer, yielding 0.0003 g of the macrocycle (compound 4) as a TFA salt (.$C_2HF_3O_2$).

Table F-3 lists the compounds that were prepared according to the above Example. The following abbreviations were used in the tables: .$C_2HF_3O_2$ stands for the trifluoroacetate salt.

TABLE F-3

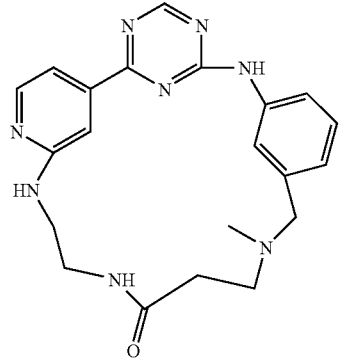 [SMILES: CN1CCC(=O)NCCNc2cc(ccn2)-c2ncnc(n2)Nc2cccc(c2)C1]

Co. No. 17; •$C_2HF_3O_2$

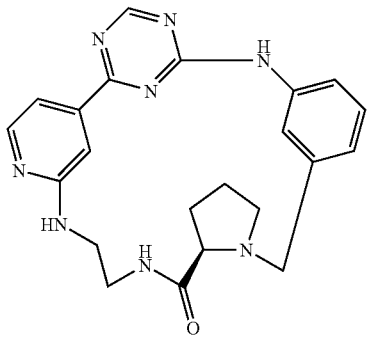 [SMILES: O=C1NCCNc2cc(ccn2)-c2ncnc(n2)Nc2cccc(c2)CN2CCC[C@H]12]

Co. No. 18; •$C_2HF_3O_2$

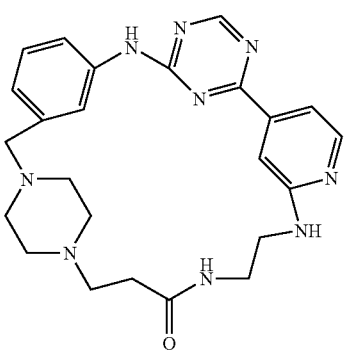 [SMILES: O=C1CCN2CCN(CC2)Cc2cccc(c2)Nc2ncnc(n2)-c2ccnc(c2)NCCN1]

Co. No. 19; •$C_2HF_3O_2$

Example B4

Preparation of Compound 5

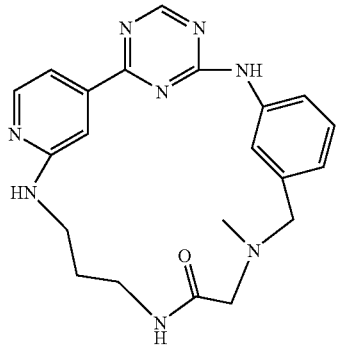 [SMILES: CN1CC(=O)NCCCNc2cc(ccn2)-c2ncnc(n2)Nc2cccc(c2)C1]

A solution of intermediate 16 (0.000125 mol) in DMF (10 ml) was added dropwise to a solution of HBTU (3 equiv) and DIPEA (30 equiv) in DMF (10 ml). Next, the solvent was evaporated and the residue purified by reversed-phase high-performance liquid chromatography (ammonium acetate-buffer) and desalted with TFA buffer, yielding 0.0004 g of the macrocycle (compound 5) as a TFA salt (.$C_2HF_3O_2$).

Table F-4 lists the compounds that were prepared according to the above Example. The following abbreviations were used in the tables: .$C_2HF_3O_2$ stands for the trifluoroacetate salt.

TABLE F-4

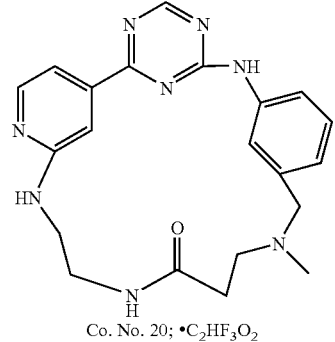

Co. No. 20; •$C_2HF_3O_2$

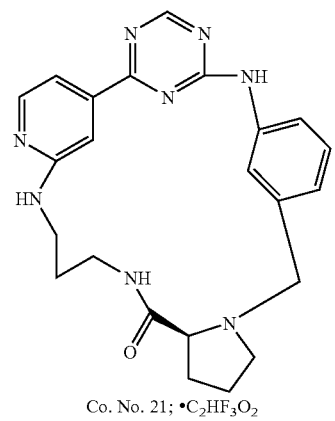

Co. No. 21; •$C_2HF_3O_2$

TABLE F-4-continued

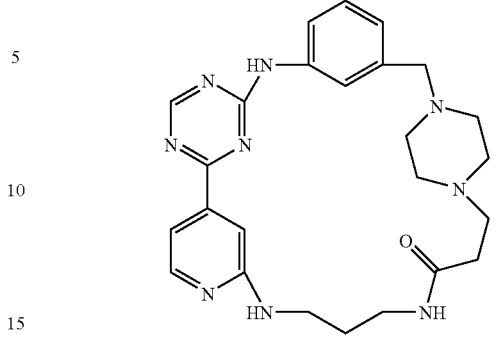

Co. No. 22; •$C_2HF_3O_2$

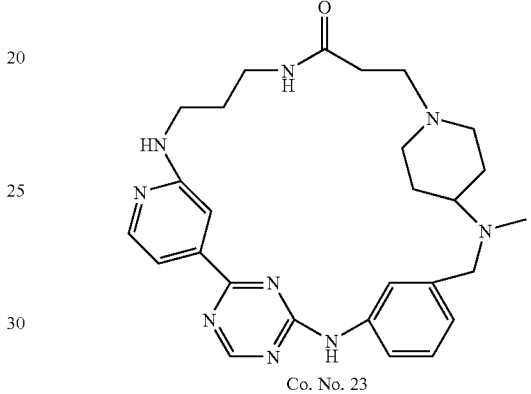

Co. No. 23

Example B5

Preparation of Compound 6

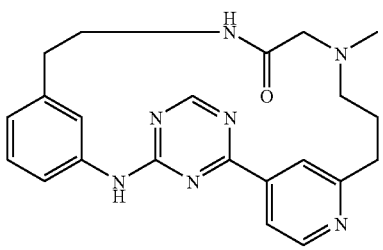 [SMILES: CN1CCCc2cc(ccn2)-c2ncnc(n2)Nc2cccc(c2)CCCNC(=O)C1]

The crude solution of intermediate 21 (0.00025 mol) in DMF (10 ml) was added dropwise to a solution of HBTU (0.00075 mol) and DIPEA (0.0100 mol) in DMF (10 ml). The solvent was evaporated, then this fraction was purified by reversed-phase high-performance liquid chromatography (ammonium acetate-buffer) and desalted with TFA buffer. The product fractions were collected and the solvent was evaporated, yielding 0.0149 g of compound 6 (15%; M.P.: 263.1-264.3° C.).

Table F-5 lists the compounds that were prepared according to the above Example. The following abbreviations were used in the tables: .$C_2HF_3O_2$ stands for the trifluoroacetate salt.

TABLE F-5
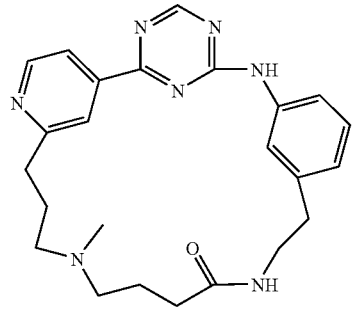 [SMILES: CN1CCCC(=O)NCCc2cccc(c2)Nc2ncnc(n2)-c2ccnc(c2)CCC1]
Co. No. 24
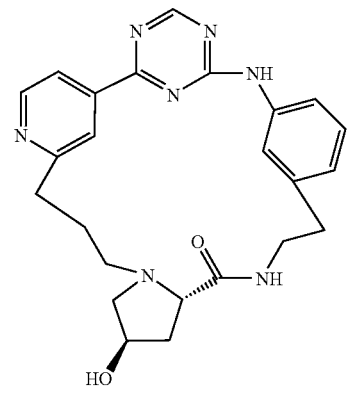 [SMILES: O=C1NCCc2cccc(c2)Nc2ncnc(n2)-c2ccnc(c2)CCCN2C[C@H](O)C[C@@H]12]
Co. No. 25; •C₂HF₃O₂;
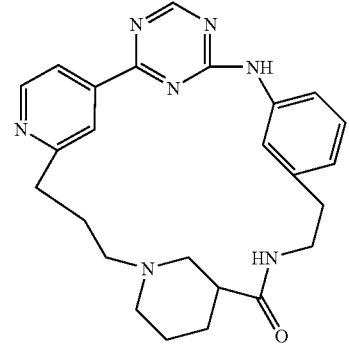 [SMILES: O=C1NCCc2cccc(c2)Nc2ncnc(n2)-c2ccnc(c2)CCCN2CCCC1C2]
Co. No. 26; •C₂HF₃O₂
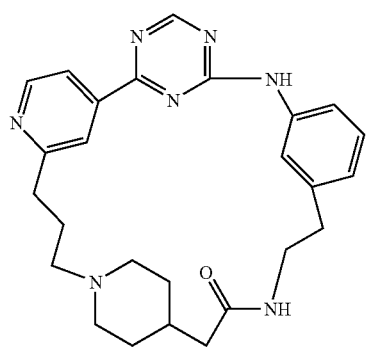 [SMILES: O=C1CC2CCN(CCCc3cc(ccn3)-c3ncnc(n3)Nc3cccc(c3)CCN1)CC2]
Co. No. 27
TABLE F-5-continued
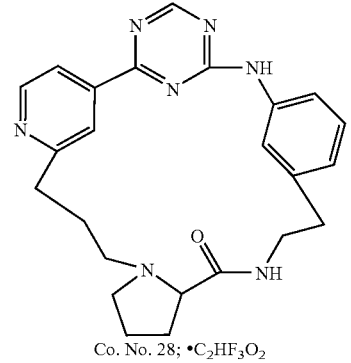
Co. No. 28; •C₂HF₃O₂
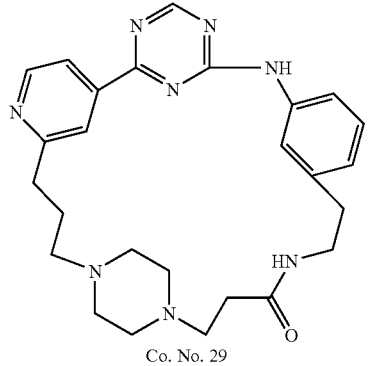
Co. No. 29
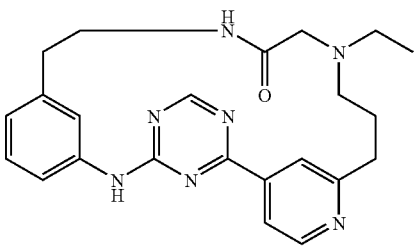 [SMILES: CCN1CCCc2cc(ccn2)-c2ncnc(n2)Nc2cccc(c2)CCNC(=O)C1]
Co. No. 30; •C₂HF₃O₂
Example B6
Preparation of Compound 7
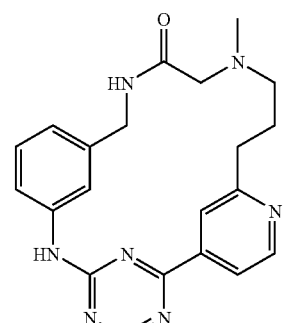
A solution of intermediate 26 (0.00025 mol) in DMF (10 ml) was added dropwise to a solution of HBTU (0.00075 mol) and DIPEA (0.0025 mol) in DMF (10 ml). The solvent was evaporated and the residue was purified by reversed-phase high-performance liquid chromatography (ammonium acetate-buffer). The product fractions were collected and the compound was extracted as a free base, yielding 0.0276 g of compound 7 (28%; M.P.: 201.9-203.3° C.).

TABLE F-5

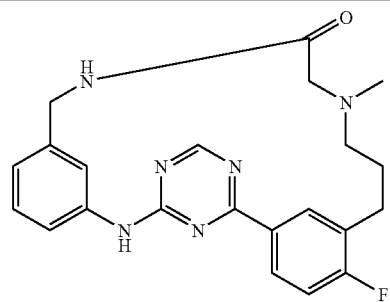 [SMILES: CN1CCCc2cc(ccc2F)-c2ncnc(n2)Nc2cccc(c2)CNC(=O)C1]

Co. No. 70 (from Int. 26a)

Example B7

Preparation of Compound 8

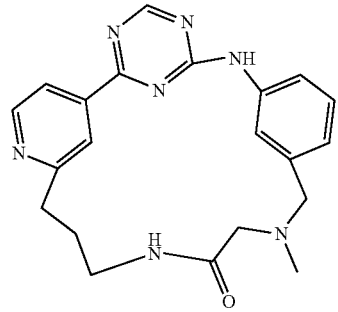 [SMILES: CN1CC(=O)NCCCc2cc(ccn2)-c2ncnc(n2)Nc2cccc(c2)C1]

A solution of intermediate 28 (0.00229 mol) in DMF (100 ml) was added dropwise to a solution of HBTU (0.00458 mol) and DIPEA (0.069 mol) in DMF (200 ml), while stirring vigorously. The reaction was quenched with 7N $NH_3$/MeOH (50 ml) and stirred for 30 minutes at room temperature. Next, the solvent was evaporated. The residue was purified by reversed-phase high-performance liquid chromatography (ammonium acetate-buffer) and subsequently crystallized from $CH_3CN$, yielding 0.328 g (37%; LCMS: 99% P; M.P.: 257.3-258.9° C.) of compound 8.

Table F-6 lists the compounds that were prepared according to the above Example.

TABLE F-6

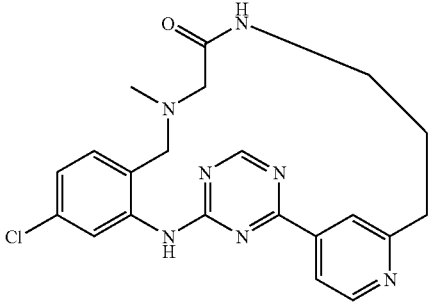 [SMILES: CN1CC(=O)NCCCc2cc(ccn2)-c2ncnc(n2)Nc2cc(Cl)ccc2C1]

Co. No. 31; NMR: OK; CHN: OK; M.P.: 243.8-245.6° C.

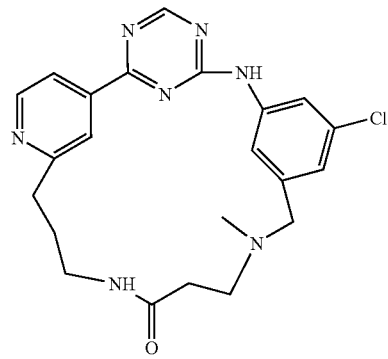 [SMILES: CN1CCC(=O)NCCCc2cc(ccn2)-c2ncnc(n2)Nc2cc(Cl)cc(c2)C1]

Co. No. 32; M.P.: 258.6-259.7° C.

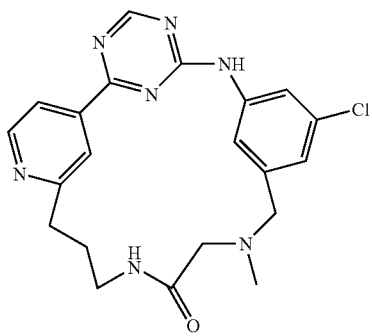 [SMILES: CN1CC(=O)NCCCc2cc(ccn2)-c2ncnc(n2)Nc2cc(Cl)cc(c2)C1]

Co. No. 33; NMR: OK; CHN: OK; M.P.: 283.9-285.6° C.

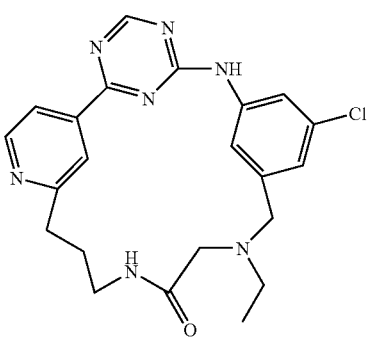 [SMILES: CCN1CC(=O)NCCCc2cc(ccn2)-c2ncnc(n2)Nc2cc(Cl)cc(c2)C1]

Co. No. 34; M.P.: 239.4-240.9° C.

Example B8

Preparation of Compound 9

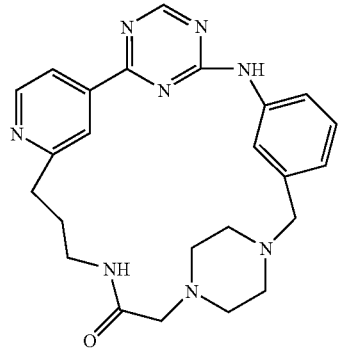 [SMILES: O=C1CN2CCN(CC2)Cc2cccc(c2)Nc2ncnc(n2)-c2ccnc(c2)CCCN1]

A solution of intermediate 30 (0.00229 mol) in DMF (100 ml) was added dropwise to a solution of HBTU (0.00458 mol) and DIPEA (0.069 mol) in DMF (200 ml), while stirring vigorously. The reaction was quenched with 7N $NH_3$/MeOH (50 ml) and stirred for 30 minutes at room temperature. Next, the solvent was evaporated. The residue was purified by reversed-phase high-performance liquid chromatography (ammonium acetate-buffer). The desired fractions were collected and the solvent was evaporated. The aqueous concentrate was extracted with $CH_2Cl_2$. The extract's solvent was evaporated, yielding 0.296 g (29%; yellow crystals; LCMS: 98% P; M.P.: 250.4-252.1° C.) of compound 9.

Table F-7 lists the compounds that were prepared according to the above Example. The following abbreviations were used in the tables: $.C_2HF_3O_2$ stands for the trifluoroacetate salt.

TABLE F-7

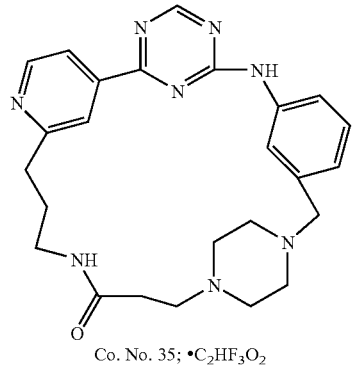

Co. No. 35; •$C_2HF_3O_2$

TABLE F-7-continued

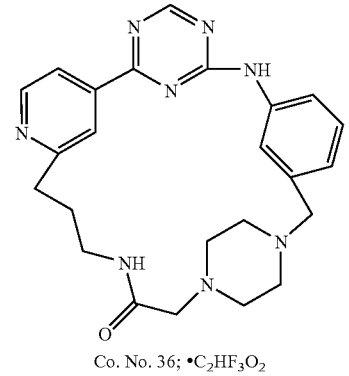

Co. No. 36; •$C_2HF_3O_2$

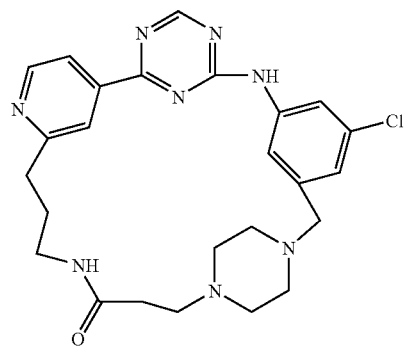 [SMILES: O=C1CCN2CCN(CC2)Cc2cc(Cl)cc(c2)Nc2ncnc(n2)-c2ccnc(c2)CCCN1]

Co. No. 37; M.P.: 295.8-296.7° C.

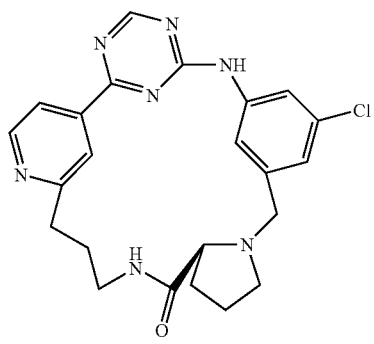 [SMILES: O=C1NCCCc2cc(ccn2)-c2ncnc(n2)Nc2cc(Cl)cc(c2)CN2CCC[C@@H]12]

Co. No. 38; M.P.; 287.6-288.7° C.

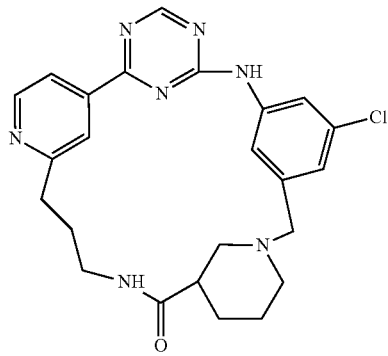 [SMILES: O=C1NCCCc2cc(ccn2)-c2ncnc(n2)Nc2cc(Cl)cc(c2)CN2CCCC1C2]

Co. No. 39; M.P.; 288.7-290.1° C.

TABLE F-7-continued

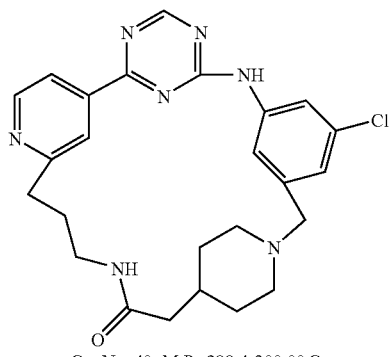

Co. No. 40; M.P.: 298.4-300.0° C.

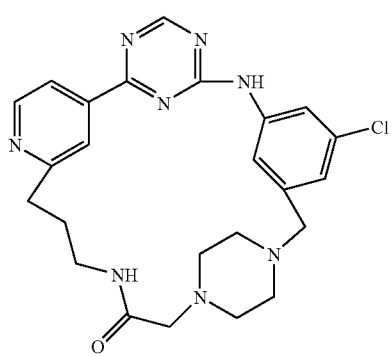 [SMILES: O=C1CC2CCN(CC2)Cc2cc(Cl)cc(c2)Nc2ncnc(n2)-c2ccnc(c2)CCCN1]

Co. No. 41; M.P.: 313.1-314.8° C.

Example B9

Synthesis of Compound 42

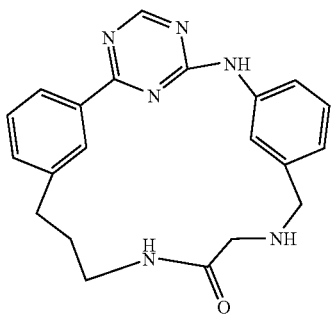 [SMILES: O=C1CNCc2cccc(c2)Nc2ncnc(n2)-c2cccc(c2)CCCN1]

A mixture of intermediate 37 (crude compound) and DIPEA (2.00 mL, 0.012 mol) in 10 mL of DMF was added dropwise to HBTU (0.284 g, 0.00075 mol) in 10 mL DMF. After addition, the solvent was evaporated and the residues redissolved in 10 mL $CH_2Cl_2$/MeOH (9:1). Amberlyst A-26 resin (5.5 g) was added to scavenge acidic components and the mixture was shaken for 24 hours. Filtration gave the crude product, which was purified by column chromatograpy (silica gel, eluent $CH_2Cl_2$/MeOH, 15:1 to 50:1), providing 0.018 g of compound 42 (19% from intermediate 35, LCMS: 91% P).

Table F-8 lists the compounds that were prepared according to the above Example.

TABLE F-8

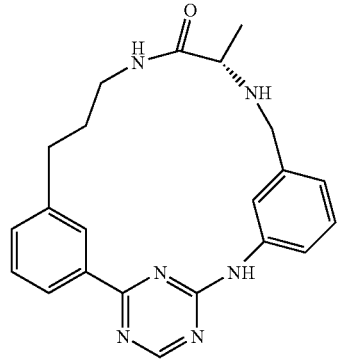 [SMILES: C[C@@H]1NCc2cccc(c2)Nc2ncnc(n2)-c2cccc(c2)CCCNC1=O]

Co. No. 44

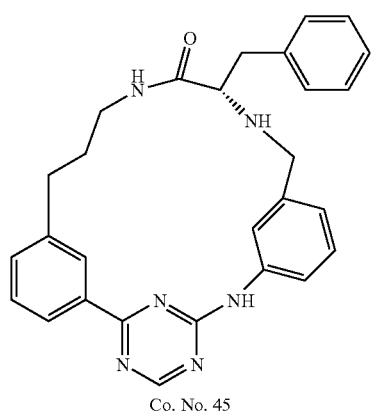

Co. No. 45

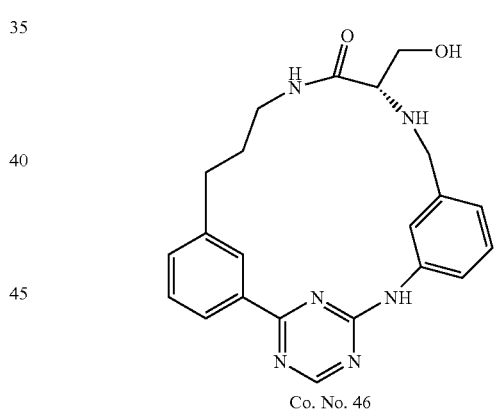

Co. No. 46

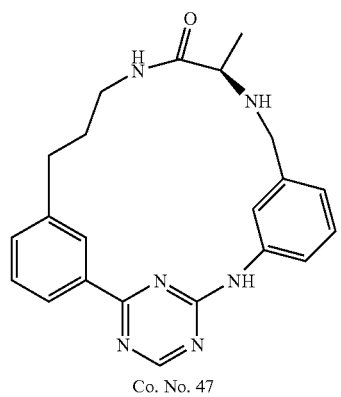

Co. No. 47

TABLE F-8-continued
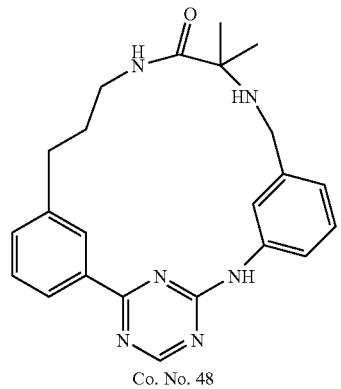
Co. No. 48
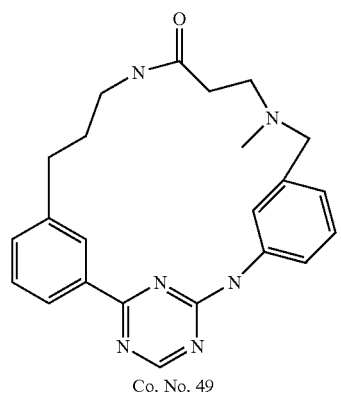
Co. No. 49
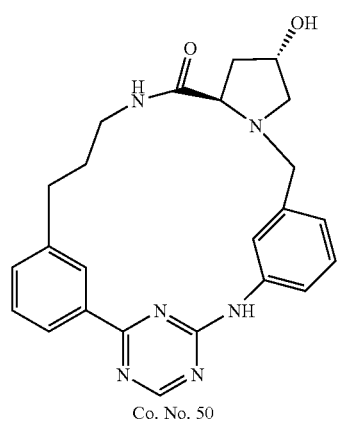
Co. No. 50
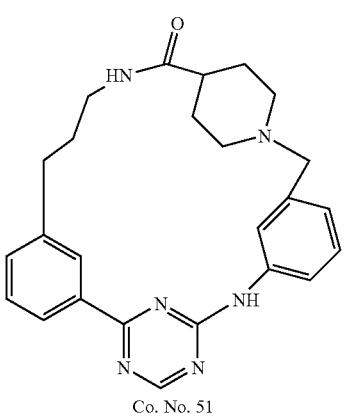
Co. No. 51
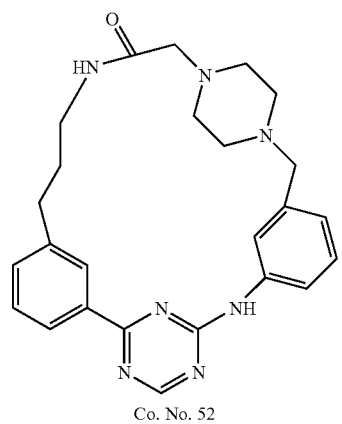
Co. No. 52
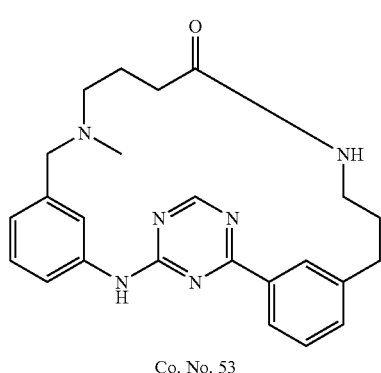
Co. No. 53
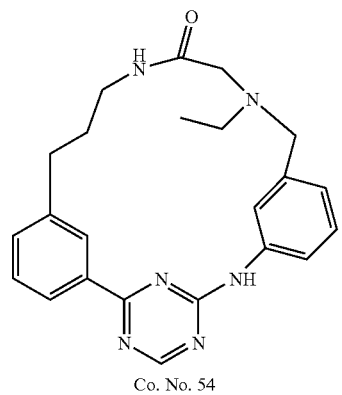
Co. No. 54
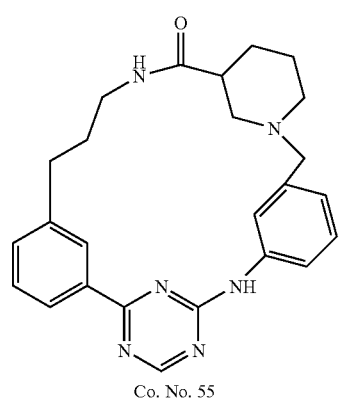
Co. No. 55

TABLE F-8-continued

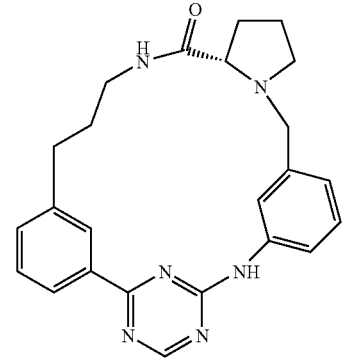 [SMILES: O=C1NCCCc2cccc(c2)-c2ncnc(n2)Nc2cccc(c2)CN2CCC[C@@H]12]

Co. No. 56;

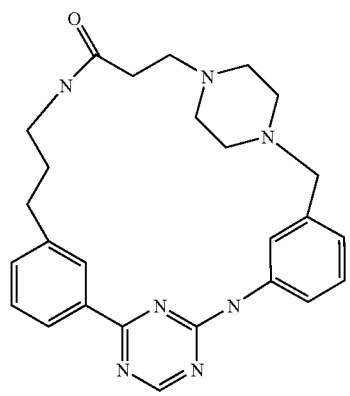 [SMILES: O=C1CCN2CCN(CC2)Cc2cccc(c2)Nc2ncnc(n2)-c2cccc(c2)CCCN1]

Co. No. 57

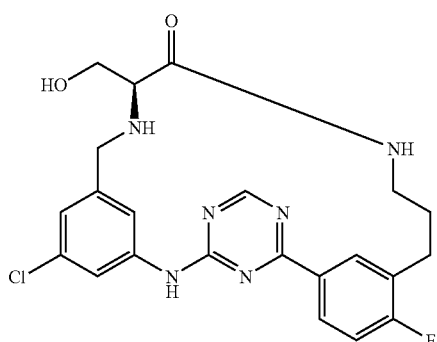

Co. No. 71 (from Int. 37a)

Example B10

Preparation of Compound 43

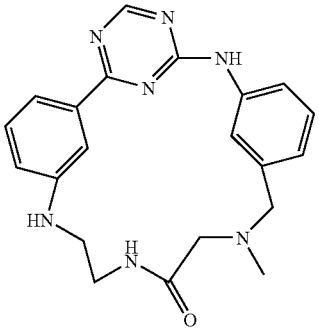 [SMILES: CN1CC(=O)NCCNc2cccc(c2)-c2ncnc(n2)Nc2cccc(c2)C1]

A mixture of intermediate 44 (crude compound) and DIPEA (1.27 mL, 0.0075 mol) in 10 mL of DMF was added dropwise to HBTU (0.284 g, 0.00075 mol) in 20 mL DMF. After addition, the solvent was evaporated and the residues redissolved in 10 mL $CH_2Cl_2$. Amberlyst A-26 resin (5.5 g) was added to scavenge acidic components and the mixture was shaken over the weekend. Filtration gave the crude product, which was purified by column chromatograpy (silica gel, eluent $CH_2Cl_2$/MeOH, 15:1 to 20:1), providing 0.021 g of compound 43 (21% from intermediate 42, LCMS: 90% P).

Table F-9 lists the compounds that were prepared according to the above Example.

TABLE F-9

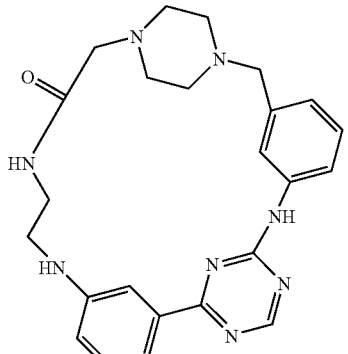

Co. No. 58

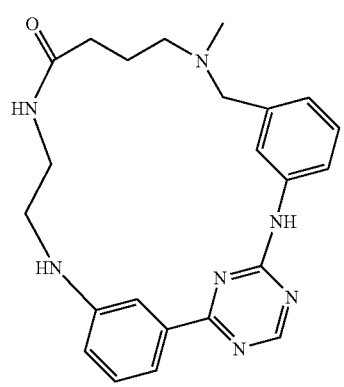 [SMILES: CN1CCCC(=O)NCCNc2cccc(c2)-c2ncnc(n2)Nc2cccc(c2)C1]

Co. No. 59

TABLE F-9-continued

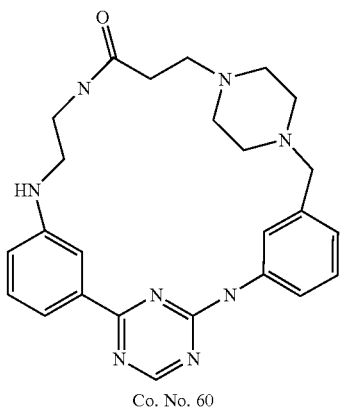

Co. No. 60

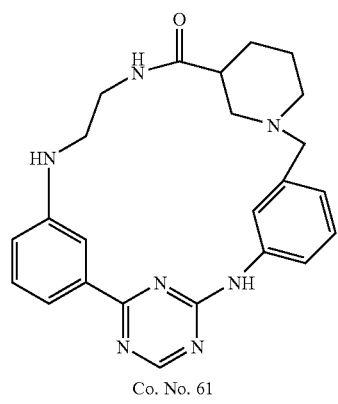

Co. No. 61

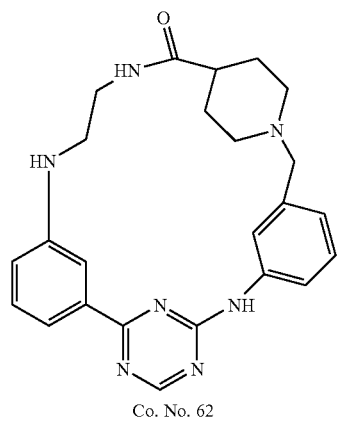

Co. No. 62

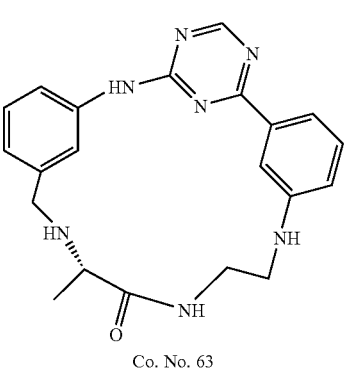

Co. No. 63

TABLE F-9-continued

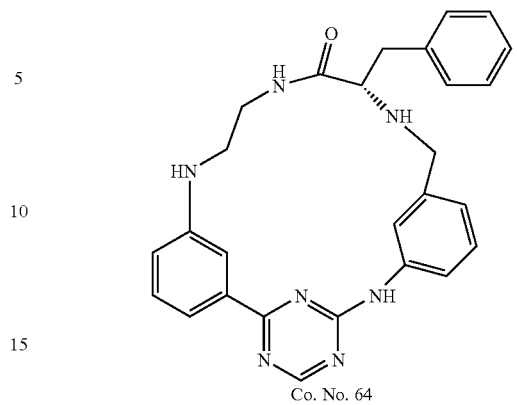

Co. No. 64

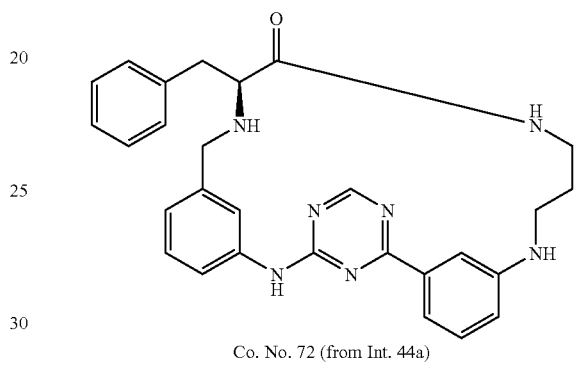

Co. No. 72 (from Int. 44a)

Example B11

Preparation of Compound 73

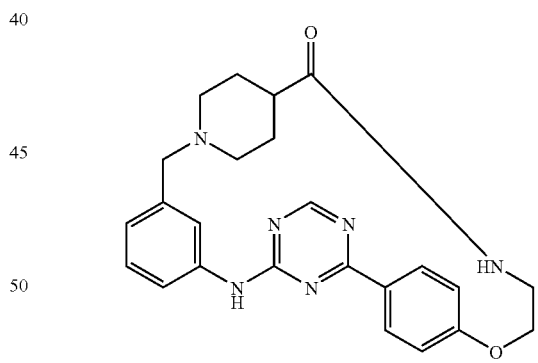

A solution of intermediate (max. 0.00025 mol) in DMF (10 ml) was added dropwise to a solution of HBTU (0.000750 mol) and DIPEA (0.0075 mol) in DMF (10 ml). Upon addition, the reaction mixture was stirred for one hour at room temperature. $Na_2CO_3$ was added and the mixture was stirred for 2 hours at room temperature, then filtered. The filtrate's solvent was evaporated. The residue was taken up into THF (10 ml). Amberlyst™ A26 OH (7 g) was added and the mixture was stirred at room temperature for overnight. The resin was filtered off, washed with a mixture of $CH_2Cl_2$/MeOH 10/1, and the filtrate's solvent was evaporated. The residue was purified by flash column chromatography over silica gel (eluent: $CH_2Cl_2$/MeOH mixture). The product fractions were collected and the solvent was evaporated, yielding 0.0077 g (99% by LCMS) of compound 73.

Example B12

Preparation of Compounds 74 and 75

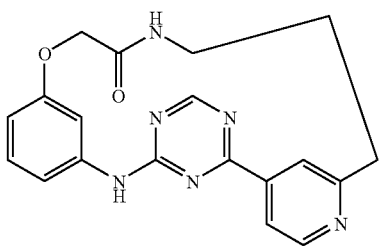
Compound 74

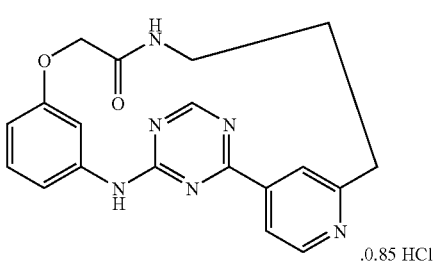
Compound 75
.0.85 HCl

Intermediate (0.002 mol) dissolved in DMF (50 ml) was added drop wise to a mixture of HBTU (0.004 mol) and DIPEA (0.040 mol) in DMF (200 ml). The solvent and DIPEA were evaporated. The residue was triturated under MeOH (50 ml). The precipitate was filtered off and washed with MeOH, H$_2$O and then MeOH again. This filter residue was triturated under NaHCO$_3$ 10% aqueous solution overnight. The precipitate was filtered off and washed with MeOH, H$_2$O and then MeOH again. This residue was dried (vacuo, 65° C.), yielding 0.7343 g (100%; LCMS: 96%; MP: >350° C.) of compound 74. A part of compound (0.050 g) was dissolved in 6N HCl in 2-propanol (15 ml). The mixture was sonicated for 1 hour and then stored overnight in the fridge. The precipitate was filtered off and dried (vacuo, 65° C.), yielding 0.0518 g (85%, LCMS: 95%) LCMS of compound 75 as a hydrochloric acid salt (0.0.85HCl).

Example B13

Preparation of Compound 76

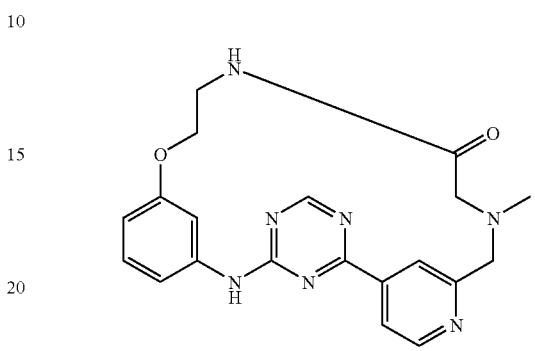

A solution of intermediate (max. 0.00025 mol) in DMF (10 ml) was added dropwise to a solution of HBTU (0.000750 mol) and DIPEA (0.01176 mol) in DMF (10 ml). Upon addition, the reaction mixture was stirred for 30 minutes at room temperature. Na$_2$CO$_3$ (2 g) was added and the mixture was stirred for 2 hours at room temperature, then filtered. The filtrate's solvent was evaporated. The residue was taken up into THF/MeOH 10/1. Amberlyst A26 OH resin was added and the mixture was stirred at room temperature for 24 hours. The resin was filtered off and the filtrate's solvent was evaporated. The residue was purified by reversed-phase high-performance liquid chromatography. The product fractions were collected and the solvent was evaporated, yielding 0.031 g of compound 76.

Example B14

Preparation of Compound 77

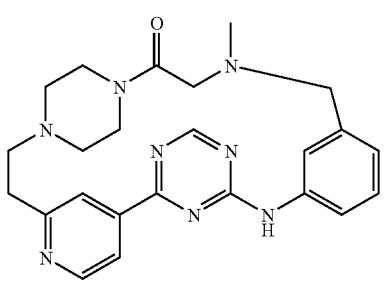 [SMILES: CN1CC(=O)N2CCN(CCc3cc(ccn3)-c3ncnc(n3)Nc3cccc(c3)C1)CC2]

A mixture of intermediate (max. 0.00102 mol) in DMF (50 ml) was added dropwise to a solution of HBTU (0.00306 mol) and DIPEA (0.0306 mol) in DMF (300 ml). The reaction mixture was stirred for 1 hour at room temperature. The reaction mixture was concentrated and the residue was partitioned between CH$_2$Cl$_2$/Na$_2$CO$_3$ solution (2×). The separated organic layer was dried (MgSO$_4$), filtered and the solvent was evaporated. The residue was purified by reversed-phase high-performance liquid chromatography (buffer NH₄HCO₃), yielding 0.060 g (13%; M.P.: 246-249° C.; LCMS: 99%) of compound 77.

Example B15

Preparation of Compound 78

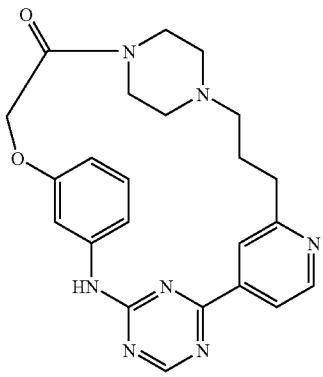 [SMILES: O=C1COc2cccc(c2)Nc2ncnc(n2)-c2ccnc(c2)CCCN2CCN1CC2]

Crude intermediate (0.00053 mol) dissolved in DMF (50 ml) was added drop wise to a mixture of HBTU (0.00106 mol) and DIPEA (0.0053 mol) in DMF (100 ml). 7N NH₃ in MeOH (20 ml) was added to the reaction mixture and stirred for 15 minutes. The solvent was evaporated. The residue was dissolved in CH₂Cl₂, NaHCO₃ saturated aqueous solution was added and then stirred overnight at room temperature. The organic layer was separated and the solvent was evaporated. The residue was purified by flash column chromatography over silica gel (eluent: from 100% CH₂Cl₂ to CH₂Cl₂/MeOH/ 7N NH₃ in MeOH 95/2.5/2.5). The product fractions were collected and the solvent was evaporated. The residue was crystallized from CH₃CN, yielding 0.1513 g (66%; LCMS: 100%; M.P.: 266.9° C. to 268.1° C.; NMR confirmed structure) of compound 78.

Example B16

Preparation of Compound 79

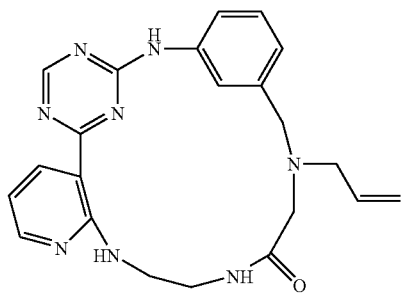 [SMILES: C=CCN1CC(=O)NCCNc2ncccc2-c2ncnc(n2)Nc2cccc(c2)C1]

Crude intermediate 75 (0.00057 mol) dissolved in DMF (10 ml) was added drop wise to a mixture of HBTU (0.000170 mol) and DIPEA (2 ml) in DMF (20 ml). When all intermediate was consumed, the reaction mixture was quenched with NH₃/MeOH saturated solution (5 ml). The solvent was evaporated (vacuo). The residue was purified by reversed phase high-performance liquid chromatography, yielding 0.030 g (NMR confirmed structure) of compound 79.

Example B17

Preparation of Compound 80

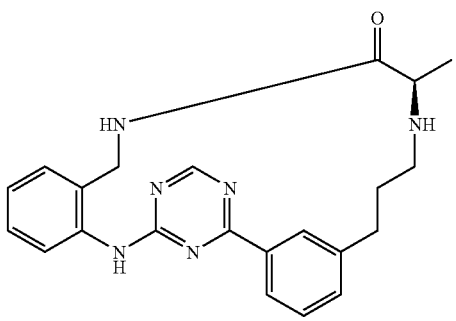 [SMILES: C[C@H]1NCCCc2cccc(c2)-c2ncnc(n2)Nc2ccccc2CNC1=O]

A solution of intermediate (max. 0.00025 mol) in DMF (10 ml) was added dropwise to a solution of HBTU (0.000750 mol) and DIPEA (0.01176 mol) in DMF (10 ml). Upon addition, the reaction mixture was stirred for 30 minutes at room temperature. Na₂CO₃ (2 g) was added and the mixture was stirred overnight at room temperature, then filtered. The filtrate's solvent was evaporated. The residue was taken up into THF/MeOH 9/1 (10-15 ml). Amberlyst™ A26 OH (6-7 g) was added and the mixture was stirred at room temperature for 24 hours. The resin was filtered off and the filtrate's solvent was evaporated. The residue was purified by reversed-phase HPLC. The product fractions were collected and the solvent was evaporated, yielding compound 80 (8 mg; LCMS: 93%).

Example B18

Preparation of Compound 81 and 82

Compound 81

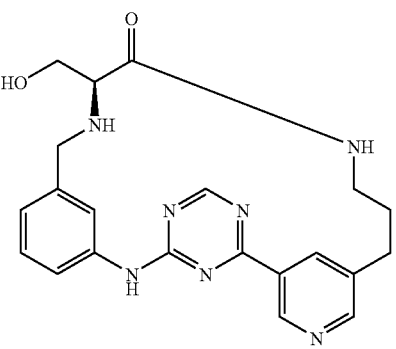

compound 82

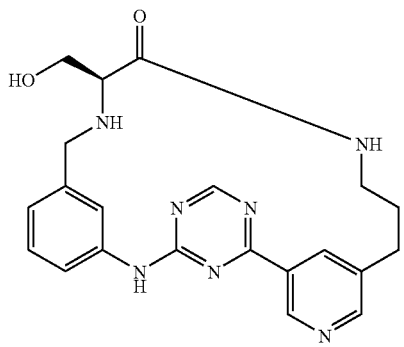

Intermediate as a mixture (0.0118 mol) was suspended in DMF (200 ml). This suspension was added drop wise to a mixture of HBTU (0.0472 mol) and DIPEA (125 ml) in DMF (100 ml). The reaction mixture was quenched with 7N $NH_3$ in MeOH. The solvent was evaporated and the residue was suspended in $H_2O$. The precipitate was filtered off and the filter residue was dissolved in $CH_2Cl_2$/MeOH. Silica was added to the solution and then the solvent was evaporated. The residue was purified by column chromatography over silica gel. The product fractions were collected and the solvent was evaporated. the residue was then purified by chiral reversed phase high-performance liquid chromatography. The 2 product fractions were collected and the solvents were evaporated, yielding 0.560 g of compound 81 (S-configuration) and 0.250 g of compound 82 (R-configuration).

Example B19

Preparation of Compound 83

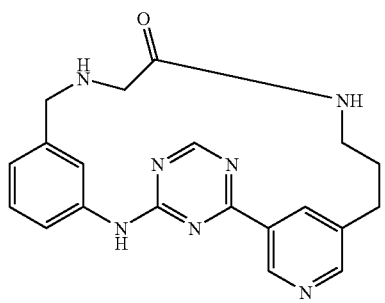 [SMILES: O=C1CNCc2cccc(c2)Nc2ncnc(n2)-c2cncc(c2)CCCN1]

Intermediate (0.0006 mol) was added dissolved in extra dry $CH_2Cl_2$ (20 ml) and degassed with $N_2$ for 5 minutes. 1,3-dimethyl-2,4,6(1H,3H,5H)-pyrimidinetrione (0.0018 mol) and then Pd(PPh$_3$)$_4$ (0.035 g) were added to the reaction mixture and stirred for 24 hours at room temperature ($N_2$ atmosphere). $Na_2CO_3$ 10% aqueous solution and $CH_2Cl_2$/MeOH (90/10) were added to the reaction mixture. The resulting biphasic mixture was filtered and the precipitate was kept. The organic layer of the biphasic filtrate was separated and the aqueous layer was extracted with 3×50 mL $CH_2Cl_2$/MeOH (90/10). The solvent was evaporated and the residue was triturated with $CH_3CN$ at 80° C. for 2 hours. The precipitate was filtered off, combined with the precipitate obtained above and dried, yielding 0.1593 g (70%; LCMS: 96%; M.P.: 306.1° C. to 307.7° C.; NMR confirmed structure) of compound 83.

Example B20

Preparation of Compound 84

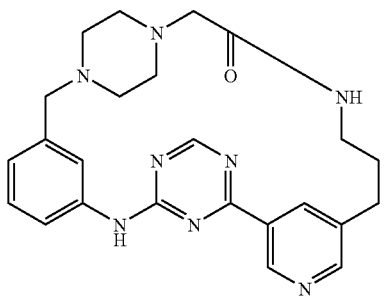 [SMILES: O=C1CN2CCN(CC2)Cc2cccc(c2)Nc2ncnc(n2)-c2cncc(c2)CCCN1]

A solution of intermediate (max. 0.00025 mol) in DMF (10 ml) was stirred. DIPEA (0.011 mol) was added. The resultant solution was added dropwise to a solution of HBTU (0.000750 mol) and DIPEA (0.01176 mol) in DMF (10 ml). After one hour, the solvent was evaporated. The residue was taken up into $CH_2Cl_2$/MeOH 9/1. Amberlyst™ A26 OH (6-7 g) was added and the mixture was stirred overnight at room temperature. The resin was filtered off and the filtrate's solvent was evaporated. The residue was purified by reversed-phase HPLC, yielding 0.030 g (27% over all steps) of compound 84.

Example B21

Preparation of Compound 85

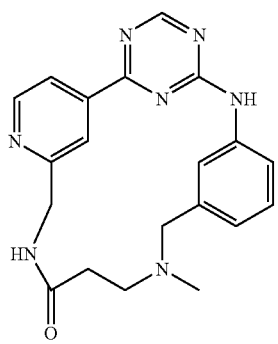 [SMILES: CN1CCC(=O)NCc2cc(ccn2)-c2ncnc(n2)Nc2cccc(c2)C1]

Intermediate (0.00038 mol) in DMF (80 ml) was added drop wise to a solution of HBTU (0.00114 mol) and DIPEA (0.0019 mol) in DMF (80 ml). 7N $NH_3$ in MeOH (50 ml) was added to the reaction mixture. The solvent was evaporated and the residue was purified by reversed-phase high performance liquid chromatography (standard gradient elution with $NH_4OAc$ buffer). The product fractions were collected and the solvent was evaporated. The residue was partitioned between $CH_2Cl_2$ and $Na_2CO_3$ 10% aqueous solution. The separated organic layer was dried ($MgSO_4$), filtered, the solvent was evaporated and co-evaporated with $CH_3CN$. The residue was dried, yielding 0.033 g (23%; LCMS: 99%; M.P.: 240° C. to 241° C.; NMR confirmed structure) of compound 85.

Compound Identification
LCMS-Methods:

The HPLC gradient was supplied by a Waters Alliance HT 2790 system with a quaternary pump with degasser, an autosampler, columnheater set at 40° C. and DAD detector. Flow from the column was split to a Waters 996 photodiode array (PDA) detector and a Waters-Micromass ZQ mass spectrometer with an electrospray ionization source operated in positive and negative ionization mode. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

Method 1:

Reversed phase HPLC was carried out on a Xterra MS C18 column (3.5 mm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 uL was used.

Method 2:

Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 μl was used. Cone voltage was 10 V for positive ionization mode and 20 V for negative ionization mode.

Method 3:

Reversed phase HPLC was carried out on a Xterra MS C18 column (3.5 mm, 4.6×100 mm) with a flow rate of 1.6 ml/min. Two mobile phases (mobile phase A methanol/H2O; mobile phase B 0.1% formic acid) were employed to run a gradient condition from 100% B to 5% B 12 minutes. An injection volume of 10 uL was used.

Method 4:

Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 6.80 minutes.

Method 5: Reversed phase HPLC was carried out on a SB-C18 Crt column (2.1×30 mm, 1.8 μm) with a flow rate of 5 ml/min. A gradient run was used from 95% water and 5% acetonitrile to 95% acetonitrile in 2 minutes.

TABLE retention time (RT in minutes) and molecular weight as the MH+

| Comp. No. | Method LCMS | Rt | MH+ |
|---|---|---|---|
| Int. 2 | 3 | 11.04 | 433 |
| Int. 23 | 1 | 5.38 | 433 |
| 1 | 1 | 4.02 | 386 |
| 2 | 1 | 4.32 | 422 |
| 8 | 1 | 4.73 | 390 |
| 11 | 3 | 5.47 | 516 |
| 13 | 3 | 3.7 | 418 |
| 14 | 3 | 4.32 | 432 |
| 15 | 3 | 3.58 | 430 |
| 16 | 3 | 3.78 | 430 |
| 9 | 1 | 4.63 | 445 |
| 36 | 3 | 3.83 | 445 |
| 7 | 1 | 4.66 | 390 |
| 6 | 1 | 4.86 | 404 |
| 4 | 3 | 4.21 | 391 |
| 17 | 3 | 4.31 | 405 |
| 23 | 1 | 4.09 | 502 |
| 24 | 3 | 8.28 | 432 |
| 25 | 3 | 7.45 | 446 |
| 26 | 3 | 7.63 | 444 |
| 28 | 3 | 7.63 | 430 |
| 30 | 3 | 7.63 | 418 |
| 31 | 3 | 2.07 | 423 |
| 32 | 1 | 4.99 | 438 |
| 37 | 1 | 5.52 | 493 |
| 38 | 1 | 5.79 | 450 |
| 39 | 1 | 5.45 | 464 |
| 40 | 1 | 4.95 | 464 |
| 41 | 1 | 5.32 | 479 |
| 33 | 1 | 5.46 | 424 |
| 34 | 1 | 5.76 | 438 |
| 42 | 4 | 1.976 | 375 |
| 43 | 4 | 1.618 | 390 |
| 44 | 4 | 2.018 | 389 |
| 45 | 4 | 2.346 | 465 |
| 46 | 4 | 1.969 | 405 |
| 47 | 4 | 2.01 | 389 |
| 48 | 4 | 2.091 | 403 |
| 49 | 4 | 1.957 | 403 |
| 50 | 4 | 2.008 | 431 |
| 51 | 4 | 1.932 | 429 |
| 52 | 4 | 1.881 | 444 |
| 53 | 4 | 1.898 | 417 |
| 54 | 4 | 2.007 | 403 |
| 55 | 4 | 1.922 | 429 |
| 56 | 4 | 2.005 | 415 |
| 57 | 4 | 1.895 | 458 |
| 58 | 4 | 1.665 | 445 |
| 59 | 4 | 1.739 | 418 |
| 60 | 4 | 1.717 | 459 |
| 61 | 4 | 1.618 | 430 |
| 62 | 4 | 1.656 | 430 |
| 63 | 4 | 1.663 | 390 |
| 64 | 4 | 2.055 | 466 |
| 73 | 4 | 1.52 | 431 |
| 74 | 3 | 6.42 | 363 |
| 75 | 3 | 6.42 | 363 |
| 76 | 4 | 1.79 | 392 |
| 77 | 1 | 4.32 | 445 |
| 78 | 3 | 4.58 | 432 |
| 79 | 2 | 0.95 | 417 |
| 66 | 5 | 0.571 | 462 |
| 65 | 1 | 5.48 | 418 |
| 70 | 4 | 1.98 | 407 |
| 71 | 3 | 7.64 | 457 |
| 72 | 4 | 2.028 | 481 |
| 80 | 4 | 1.893 | 389 |
| 83 | 1 | 4.08 | 376 |
| 84 | 1 | 4.37 | 445 |
| 81 | 4 | 1.338 | 406 |
| 85 | 1 | 3.86 | 376 |
| 67 | 3 | 4.53 | 404 |
| 68 | 3 | 4.50 | 418 |
| 69 | 1 | 5.20 | 459 |

TABLE retention time (RT in minutes) and molecular weight as the MH−

| Comp. No. | Method LCMS | Rt | MH− |
|---|---|---|---|
| 10 | 3 | 6.63 | 388 |
| 3 | 3 | 6.22 | 402 |
| 35 | 3 | 6.19 | 457 |
| 12 | 3 | 6.78 | 414 |
| 18 | 3 | 4.24 | 415 |
| 19 | 3 | 4.5 | 458 |
| 5 | 3 | 4.95 | 403 |
| 20 | 3 | 5 | 417 |
| 21 | 3 | 5.02 | 429 |
| 22 | 3 | 4.54 | 472 |
| 27 | 3 | 7.23 | 456 |
| 29 | 3 | 7.1 | 471 |

Optical Rotation:

The optical rotation was measured using a polarimeter. $[\alpha]_D^{20}$ indicates the optical rotation measured with light at the wavelength of the D-line (589 nm) of sodium at a temperature of 20° C. Behind the actual value the concentration and solvent of the solution which was used to measure the optical rotation are mentioned.

| Comp. No. | $[\alpha]_D^{20}$ | concentration | solvent |
|---|---|---|---|
| 72 | −12.08° | C = 7.45 mg/5 ml | DMSO |
| 71 | −3.89° | C = 7.71 mg/5 ml | DMF |
| 69 | −17.39° | C = 10.35 mg/5 ml | DMF |

SFC-MS Methods:

Analytical SFC system from Berger Instruments (Newark, Del., USA) consists of a dual pump control module (FCM-1200) for delivery of carbon dioxide ($CO_2$) and modifier, a thermal control module for column heating (TCM2100) with temperature control in the range 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Method 1:

SFC-MS was carried out on a CHIRALCEL OJ-H column (500×4.6 mm) with a flow rate of 3 ml/min. Two mobile phases (mobile phase A: $CO_2$ mobile phase B: 2-propanol containing 0.2% 2-propylamine) were employed to run a gradient condition from 10% B to 40% B in 18 minutes to 50% B in 2 minutes and hold B for 2 minutes. Column temperature was set at 50° C. Backpressure was maintained at 110 bar.

Method 2: SFC-MS was carried out on a CHIRALCEL OJ-H column (500×4.6 mm) with a flow rate of 3 ml/min. Two mobile phases (mobile phase A: $CO_2$ mobile phase B: methanol containing 0.2% 2-propylamine) were employed to run a gradient condition from 10% B to 40% B in 18 minutes to 50% B in 2 minutes and hold B for 2 minutes. Column temperature was set at 50° C. Backpressure was maintained at 110 bar.

| Comp. No. | Method SFC-MS | Rt | Enantiomeric Excess | MH+ |
|---|---|---|---|---|
| 71 | 2 | 13.12 | 98.45 | 457 |
| 80 | 1 | 9.79 | 94.75 | 389 |

C. PHARMACOLOGICAL EXAMPLES

C1. GSK-3 Kinase Assay

In vitro GSK-3 assays were performed at room temperature in a 100 µl reaction volume of 25 mM Tris (pH 7.4) containing 10 mM $MgCl_2.6H_2O$, 1 mM DTT, 0.1 mg/ml BSA, 5% glycerol, 5.7 ng/µl GSK-3β or 0.25 ng/µl GSK-3α, 5 µM biotinylated CREB peptide, 1 µM ATP, 0.85 µCi/ml $^{33}$P-ATP and a suitable amount of a test compound. After one hour, the reaction was terminated by adding 70 µl of Stop mix (0.1 mM ATP, 5 mg/ml streptavidin coated PVT SPA beads, pH 11.0). The beads were allowed to settle overnight and the radioactivity attached to the beads was counted in a microtiter plate scintillation counter and compared with the results obtained in a control experiment (without the presence of a test compound) in order to determine the percentage of GSK-3 inhibition. The $IC_{50}$ value, i.e. the concentration (M) of the test compound at which 50% of GSK-3 is inhibited, was calculated from the dose response curve obtained by performing the above-described GSK-3 assay in the presence of different amounts of the test compound. Score 1=$pIC_{50}$ value<6, Score 2=$pIC_{50}$ value from 6-7, Score 3=$pIC_{50}$ value from 7-8, Score 4=$pIC_{50}$ value>8.

C2. GSK-3 Cellular Assay

Test compounds were tested for their ability to increase the incorporation of $^{14}$C-D-glucose into glycogen in living cells. To do this, Chang cells (360,000 cells/well) were cultured in 0.5 ml of MEM Rega 3 medium supplemented with 10% fetal calf serum, 1% L-glutamine and 2% sodium carbonate. After 3 days, cells were washed with 0.5 ml of phosphate-buffered saline and overlayed with 1 ml of serum- and glucose-free DMEM medium. Then, 2 µl of compound in DMSO and 50 µl substrate (3 mM glucose and 0.5 µCi $^{14}$C-D-glucose were added and the cultures were incubated for 90 min. Cells were then extracted with 0.5 ml of 20% KOH for 60 min at 37° C. and the cell lysates were transferred to 10 ml tubes containing 300 µl of 1 mg/ml glycogen as carrier protein. Following the addition of 2 ml ethanol, total glycogen was precipitated overnight at −20° C. and the precipitates were recovered by centrifugation. Precipitates were then resuspended in 1 ml of water and transferred to scintillation counter vials. and the amount of $^{14}$C-D-glucose incorporation into glycogen was measured by scintillation counting. Scores for the compounds according to the invention, were obtained at a test concentration of $10^{-6}$ M. Score 1=10-30% increase, Score 2=30-60% increase, Score 3=60-80% increase and Score 4=>80% increase in D-glucose incorporation.

The following table provides the scores for the compounds according to the invention obtained in the above mentioned GSK-3 assays.

| Compound No. | C1 Score α | C1 Score β | C2 Score |
|---|---|---|---|
| 1 | 4 | 4 | 3 |
| 2 | 4 | 4 | 4 |
| 10 | 4 | 4 | 4 |
| 8 | 4 | 4 | 4 |
| 3 | 2 | 3 | |
| 35 | 3 | 3 | 4 |
| 11 | 2 | 2 | |
| 12 | 2 | 2 | |
| 13 | 2 | 3 | |
| 14 | 3 | 3 | |
| 15 | 3 | 3 | |
| 16 | 3 | 3 | |
| 36 | 4 | 4 | 4 |
| 9 | 4 | 4 | 4 |
| 7 | 4 | 4 | 3 |
| 6 | 4 | 4 | 4 |
| 4 | 3 | 3 | 4 |
| 17 | 3 | 3 | |
| 18 | 2 | 2 | |
| 19 | 2 | 3 | |
| 5 | 3 | 3 | 4 |
| 20 | 2 | 3 | |
| 21 | 2 | 2 | |
| 22 | 2 | 2 | |
| 23 | 2 | 2 | |
| 24 | 2 | 3 | |
| 25 | 3 | 3 | |
| 26 | 3 | 3 | |
| 27 | 2 | 2 | |
| 28 | 2 | 3 | |
| 29 | 3 | 3 | |
| 30 | 4 | 4 | 4 |
| 31 | 1 | 1 | |
| 32 | 3 | 3 | |
| 37 | 3 | 3 | |
| 38 | 2 | 2 | |
| 39 | 2 | 3 | |
| 40 | 4 | 3 | 4 |
| 41 | 4 | 4 | 4 |
| 33 | 4 | 4 | 4 |
| 34 | 4 | 4 | 4 |
| 42 | 2 | | |
| 43 | 2 | 3 | |
| 44 | 2 | | |
| 45 | 3 | | |
| 46 | 4 | | 4 |
| 47 | 3 | | |
| 48 | 2 | | |
| 49 | 3 | | |
| 50 | 3 | | |
| 51 | 3 | | |
| 52 | 4 | | 4 |
| 53 | 3 | | |
| 54 | 4 | | 4 |
| 55 | 3 | | |
| 59 | 2 | | |
| 57 | 2 | | |
| 58 | 3 | | |
| 59 | 2 | | |
| 60 | 2 | | |
| 61 | 2 | | |
| 62 | 2 | | |
| 63 | 2 | | |
| 64 | 2 | | |
| 73 | 2 | | |
| 74 | 3 | | |
| 75 | 3 | | |
| 76 | 4 | | |
| 77 | 2 | | |
| 78 | 3 | | |
| 79 | 2 | | |
| 66 | 4 | | 4 |
| 65 | 4 | | 3 |
| 70 | 4 | | 4 |
| 71 | 4 | | 4 |
| 72 | 3 | | |
| 80 | 2 | | |
| 83 | 3 | | 4 |
| 84 | 4 | | 3 |
| 81 | 4 | | 4 |
| 88 | 2 | | |
| 67 | 4 | | 4 |
| 68 | 2 | | |
| 69 | 3 | | 2 |

C3 Kinase Profiling

The in vitro inhibition of a panel of kinases was assessed using either the glass-fiber filter technology as described by Davies, S. P. et al., Biochem J. (2000), 351; p. 95-105. In the glass-fiber filter technology the activity of the kinase of interest is measured using an appropriate substrate that is incubated with the aforementioned kinase protein in the presence of ($^{33}$P) radiolabeled ATP. ($^{33}$P) Phosporylation of the substrate is subsequently measured as radioactivity bound on a glassfiber-filter.

DETAILED DESCRIPTION

All kinases are pre-diluted to a 10× working concentration prior to addition into the assay. The composition of the dilution buffer for each kinase is detailed below.

| Buffer Composition | Kinase(s) |
|---|---|
| 20 mM MOPS pH 7.0, 1 mM EDTA, 0.1% β-mercaptoethanol, 0.01% Brij-35, 5% glycerol, 1 mg/ml BSA | Aurora-A, CDK1/cyclinB, CDK2/cyclinA, CDK2/cyclinE, CDK3/cyclinE, CDK5/p35, CDK6/cyclinD3, CDK7/cyclinH/Mat1, cSRC, Yes |

All substrates are dissolved and diluted to working stocks in de-ionised water, apart from histone H1 that is stored in 10× working stock in 20 mM MOPS pH 7.4.

C3.1 Aurora-A Human

In a final reaction volume of 25 µl, Aurora-A (h) (5-10 mU) is incubated with 8 mM MOPS pH 7.0, 0.2 mM EDTA, 200 µM LRRASLG (Kemptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 50 mM phosphoric acid and once in methanol prior to drying and scintillation counting.

C3.2 CDK1/CyclinB Human

In a final reaction volume of 25 µl, CDK1/cyclinB (h) (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.3 CDK2/CyclinA Human

In a final reaction volume of 25 µl, CDK2/cyclinA (h) (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.4 CDK2/CyclinE Human

In a final reaction volume of 25 µl, CDK2/cyclinE (h) (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.5 CDK3/CyclinE Human

In a final reaction volume of 25 µl, CDK3/cyclinE (h) (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.6 CDK5/p35 Human

In a final reaction volume of 25 µl, CDK5/p35 human (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.7 CDK6/CyclinD3 Human

In a final reaction volume of 25 µl, CDK6/cyclinD3 human (5-10 mU) is incubated with 8 mM MOPS pH 7.0, 0.2 mM EDTA, 0.1 mg/ml histone H1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.8 CDK7/CyclinH/MAT1 Human

In a final reaction volume of 25 µl, CDK7/cyclinH/MAT1 (h) (5-10 mU) is incubated with 8 mM MOPS pH 7.0, 0.2 mM EDTA, 500 µM peptide, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a P30 filtermat and washed three times for 5 minutes in 75 mM phosphoric acid and once in methanol prior to drying and scintillation counting.

C3.9 cSRC Human

In a final reaction volume of 25 µl, cSRC (h) (5-10 mU) is incubated with 8 mM MOPS pH 7.0, 0.2 mM EDTA, 250 µM KVEKIGEGTYGVVYK (Cdc2 peptide), 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution.

10 µl of the reaction is then spotted onto a P30 filtermat and washed three times for 5 minutes in 75 mM phosphoric acid and once in methanol prior to drying and scintillation counting.

C3.10 Yes Human

In a final reaction volume of 25 µl, Yes (h) (5-10 mU) is incubated with 8 mM MOPS pH 7.0, 0.2 mM EDTA, 0.1 mg/ml poly(Glu, Tyr) 4:1, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 µl of a 3% phosphoric acid solution. 10 µl of the reaction is then spotted onto a Filtermat A and washed three times for 5 minutes in 75 mM phosphoric acid and once in methanol prior to drying and scintillation counting.

The following tables provides the scores for the compounds according to the invention, obtained at a test concentration of $10^{-6}$ M using the above mentioned kinase assays.

Score 1 = 10-30% inhibition, Score 2 = 30-60% inhibition, Score 3 = 60-80% inhibition and Score 4 = >80% inhibition.

| Cpd. No. | C3.1 | C3.2 | C3.3 | C3.4 | C3.5 | C3.6 | C3.7 | C3.8 | C3.9 | C3.10 |
|---|---|---|---|---|---|---|---|---|---|---|
| 1 | 1 | 4 | 4 | 4 | 4 | 4 | 4 | 4 | 3 | 3 |
| 2 | 2 | 4 | 4 | 4 | 4 | 4 | 4 | 3 | 4 | 4 |
| 10 | 1 | 4 | 4 | 4 | 4 | 4 | 4 | 4 | 2 | 2 |
| 8 |  | 4 | 4 | 4 | 4 | 3 | 2 | 2 |  |  |
| 3 | 1 | 4 | 4 | 4 | 3 | 3 | 2 | 4 | 2 | 2 |
| 35 | 1 | 4 | 4 | 4 | 4 | 4 | 3 | 4 | 2 | 2 |
| 11 | 1 | 1 | 1 | 1 | 1 | 1 | 1 | 1 | 1 | 1 |
| 12 | 1 | 3 | 4 | 4 | 3 | 2 | 1 | 3 | 2 | 2 |
| 13 | 2 | 1 | 2 | 2 | 2 | 1 | 1 | 2 | 2 | 1 |
| 14 | 2 | 2 | 4 | 1 | 2 | 1 | 1 | 2 | 2 | 1 |
| 15 | 1 | 1 | 2 | 2 | 1 | 1 | 1 | 2 | 1 | 1 |

-continued

Score 1 = 10-30% inhibition, Score 2 = 30-60% inhibition, Score 3 = 60-80% inhibition and Score 4 = >80% inhibition.

| Cpd. No. | C3.1 | C3.2 | C3.3 | C3.4 | C3.5 | C3.6 | C3.7 | C3.8 | C3.9 | C3.10 |
|---|---|---|---|---|---|---|---|---|---|---|
| 36 | 1 | 4 | 4 | 4 | 3 | 3 | 1 | 2 | 1 | 1 |
| 9 |   | 4 | 4 | 4 | 3 | 2 | 1 | 2 |   |   |
| 7 | 1 | 4 | 4 | 4 | 4 | 4 | 1 | 2 | 2 | 2 |
| 6 | 4 | 4 | 4 | 4 | 4 | 4 | 2 | 4 | 2 | 1 |
| 17 |   | 4 | 4 | 4 | 4 | 4 | 2 | 3 |   |   |
| 18 |   | 3 | 4 | 4 | 3 | 2 | 1 | 2 |   |   |
| 19 |   | 4 | 4 | 4 | 4 | 3 | 2 | 2 |   |   |
| 20 |   | 3 | 4 | 4 | 4 | 3 | 1 | 2 |   |   |
| 21 |   | 4 | 4 | 4 | 4 | 3 | 1 | 2 |   |   |
| 22 |   | 4 | 4 | 4 | 4 | 2 | 1 | 1 |   |   |
| 23 |   | 2 | 3 | 4 | 3 | 2 | 1 | 1 |   |   |
| 24 |   | 2 | 3 | 3 | 2 | 2 | 1 | 3 |   |   |
| 25 |   | 3 | 4 | 4 | 3 | 2 | 2 | 2 |   |   |
| 26 |   | 1 | 3 | 4 | 3 | 2 | 1 | 2 |   |   |
| 27 |   | 2 | 3 | 2 | 1 | 2 | 1 | 1 |   |   |
| 31 |   | 3 | 2 | 3 | 4 | 4 | 1 | 1 |   |   |
| 30 |   | 4 | 4 | 4 | 4 | 4 | 1 | 3 |   |   |
| 32 |   | 4 | 4 | 4 | 3 | 4 | 1 | 2 |   |   |
| 37 |   | 4 | 4 | 4 | 4 | 4 | 2 | 3 |   |   |
| 38 |   | 4 | 4 | 4 | 3 | 2 |   | 3 |   |   |
| 39 |   | 2 | 3 | 3 | 2 | 1 |   | 3 |   |   |
| 40 |   | 4 | 4 | 4 | 4 | 4 | 2 | 3 |   |   |
| 41 |   | 4 | 4 | 4 | 3 | 3 | 1 | 2 |   |   |
| 33 |   | 4 | 4 | 4 | 4 | 4 | 3 | 3 |   |   |
| 34 |   | 4 | 4 | 4 | 4 | 4 | 2 | 2 |   |   |
| 58 |   | 2 | 3 | 2 | 1 | 2 | 1 |   |   |   |
| 54 |   | 3 | 4 | 4 | 2 | 3 | 1 | 1 | 1 | 2 |
| 52 |   | 4 | 4 | 4 | 2 | 3 |   | 1 |   |   |
| 46 |   | 4 | 4 | 4 | 4 | 4 | 1 | 1 |   |   |
| 65 |   | 2 |   |   |   |   |   |   |   |   |
| 66 |   | 4 | 3 | 4 | 3 | 3 |   | 1 |   | 1 |
| 71 | 2 | 4 | 2 | 4 | 4 | 4 | 2 | 4 | 4 | 4 |
| 83 | 2 |   | 2 |   |   |   |   |   | 2 | 2 |
| 84 |   | 3 | 2 | 3 | 2 | 2 |   | 1 |   |   |
| 81 | 1 | 4 | 3 | 4 | 3 | 3 | 1 | 1 | 1 | 1 |

D. COMPOSITION EXAMPLES

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in DCM (150 ml). Then there were added DCM (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound having the formula (I)

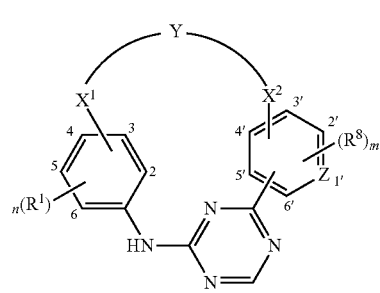

(I)

the N-oxide forms, the pharmaceutically acceptable addition salts and the stereochemically isomeric forms thereof, wherein m represents an integer from 1 to 4; n represents an integer from 1 to 4;

Z represents N or C;

Y represents —$NR^2$—$C_{1-6}$alkyl-CO—$NR^4$—, —$C_{1-4}$alkyl-$NR^9$—$C_{1-4}$alkyl-, $C_{1-6}$alkyl-CO-$Het^{10}$-, -$Het^{11}$-

CO—$C_{1-6}$alkyl-, -Het$^{12}$-$C_{1-6}$alkyl-, —CO-Het$^{13}$-$C_{1-6}$alkyl-, —CO—NR$^{10}$—$C_{1-6}$alkyl-, -Het$^1$-$C_{1-6}$alkyl-CO—NR$^5$—, or -Het$^2$-CO—NR$^6$— wherein the —$C_{1-6}$alkyl-linker in —NR$^2$—$C_{1-6}$alkyl-CO—NR$^4$— or -Het$^1$-$C_{1-6}$alkyl-CO—NR$^5$— is optionally substituted with one or where possible two or more substituents selected from hydroxy, methoxy, aminocarbonyl, halo, phenyl, indolyl, methylsulfide, thiol, hydroxyphenyl, cyanophenyl, amino and hydroxycarbonyl;

X$^1$ represents a direct bond, $C_{1-4}$alkyl, $C_{1-4}$alkyloxy-, $C_{1-4}$alkyl-CO—, $C_{2-4}$alkenyl, $C_{2-4}$alkynyl, or $C_{1-4}$alkyl-NR$^3$—, wherein said $C_{1-4}$alkyl or $C_{2-4}$alkenyl is optionally substituted with one or where possible two or more halo substituents;

X$^2$ represents a direct bond, $C_{1-4}$alkyl, $C_{1-4}$alkyloxy-, $C_{1-4}$alkyl-CO—, $C_{2-4}$alkenyl, $C_{2-4}$alkynyl, or $C_{1-4}$alkyl-NR$^7$—, wherein said $C_{1-4}$alkyl or $C_{2-4}$alkenyl is optionally substituted with one or where possible two or more halo substituents;

R$^1$ and R$^8$ each independently represent hydrogen, Het$^{14}$, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl)amino-sulfonyl, $C_{1-6}$alkoxy- substituted with halo or R$^1$ represents $C_{1-6}$alkyl substituted with one or where possible two or more substituents selected from hydroxy or halo;

R$^2$ and R$^9$ each independently represents hydrogen, $C_{1-4}$alkyl, $C_{2-4}$alkenyl, Het$^3$, Het$^4$-$C_{1-4}$alkyl-, Het$^5$-$C_{1-4}$alkylcarbonyl-, mono- or di($C_{1-4}$alkyl)amino-$C_{1-4}$alkyl-carbonyl- or phenyl optionally substituted with one or where possible two or more substituents selected from hydrogen, hydroxy, amino or $C_{1-4}$alkyloxy-;

R$^3$ and R$^7$ each independently represent hydrogen, $C_{1-4}$alkyl, Het$^6$, Het$^7$-$C_{1-4}$alkyl-, $C_{2-4}$alkenylcarbonyl- optionally substituted with $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

R$^4$, R$^5$, R$^6$ and R$^{10}$ each independently represent hydrogen or $C_{1-4}$alkyl optionally substituted with hydroxy, Het$^9$ or $C_{1-4}$alkyloxy;

Het$^1$ and Het$^2$ each independently represent a heterocycle selected from pyrrolidinyl, piperidinyl, piperazinyl, pyridinyl, pyrimidinyl, pyrazinyl, imidazolidinyl or pyrazolidinyl wherein said Het$^1$ and Het$^2$ are optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

Het$^3$ and Het$^6$ each independently represent a heterocycle selected from pyrrolidinyl or piperidinyl wherein said Het$^3$ and Het$^6$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^4$, Het$^7$ and Het$^9$ each independently represent a heterocycle selected from morpholinyl, pyrrolidinyl, piperazinyl or piperidinyl wherein said Het$^4$, Het$^7$ and Het$^9$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^5$ represents a heterocycle selected from morpholinyl, pyrrolidinyl, piperazinyl or piperidinyl wherein said Het$^5$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{10}$, Het$^{11}$ and Het$^{13}$ each independently represent a heterocycle selected from pyrrolidinyl, piperidinyl, piperazinyl, pyridinyl, pyrimidinyl, pyrazinyl, imidazolidinyl or pyrazolidinyl wherein said Het$^{10}$, Het$^{11}$ and Het$^{13}$ are optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, amino-carbonyl- or mono- or di($C_{1-4}$alkyl)amino-;

Het$^{12}$ represents a heterocycle selected from pyrrolidinyl, piperidinyl, piperazinyl, pyridinyl, pyrimidinyl, pyrazinyl, imidazolidinyl or pyrazolidinyl wherein said Het$^{12}$ is optionally substituted with amino, hydroxy, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-; mono- or di($C_{1-4}$alkyl)amino- or amino-carbonyl-; and Het$^{14}$ represents a heterocycle selected from morpholinyl; pyrrolidinyl; piperazinyl; imidazolyl; pyrrolyl; 2,3,4-triazapyrrolyl; 1,2,3-triazolyl; pyrazolyl; or piperidinyl wherein said Het$^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-.

2. A compound according to claim 1 wherein;

m represents 1; n represents 1; Z represents N or C;

Y represents —NR$^2$—$C_{1-6}$alkyl-CO—NR$^4$—, —$C_{1-4}$alkyl-NR$^9$—$C_{1-4}$alkyl-, $C_{1-6}$alkyl-CO-Het$^{10}$-, -Het$^{11}$-CO—$C_{1-6}$alkyl-, -Het$^{12}$-$C_{1-6}$alkyl-, —CO-Het$^{13}$-$C_{1-6}$alkyl-, —CO—NR$^{10}$—$C_{1-6}$alkyl-, -Het$^1$-$C_{1-6}$alkyl-CO—NR$^5$—, -Het$^2$-CO—NR$^6$— wherein the —$C_{1-6}$alkyl-linker in —NR$^2$—$C_{1-6}$alkyl-CO—NR$^4$— or -Het$^1$-$C_{1-6}$alkyl-CO—NR$^5$— is optionally substituted with one or where possible two or more substituents selected from hydroxy, methoxy, aminocarbonyl, halo, cyanophenyl and phenyl;

X$^1$ represents a direct bond, —$C_{1-4}$alkyl-, $C_{1-4}$alkyloxy- or $C_{1-4}$alkyl-NR$^3$;

X$^2$ represents a direct bond, $C_{1-4}$alkyl, $C_{1-4}$alkyloxy-, $C_{1-4}$alkyl-CO—, $C_{2-4}$alkenyl, $C_{2-4}$alkynyl or $C_{1-4}$alkyl-NR$^7$— wherein said $C_{2-4}$alkenyl is optionally substituted with one or where possible two or more halo substituents;

R$^1$ represents hydrogen, Het$^{14}$ or halo;

R$^2$ represents hydrogen, $C_{1-4}$alkyl, $C_{2-4}$alkenyl or Het$^4$-$C_{1-4}$alkyl-;

R$^3$ and R$^7$ each independently represent hydrogen or $C_{1-4}$alkyl;

R$^8$ represents hydrogen;

R$^9$ represents hydrogen, $C_{1-4}$alkyl, methyl, ethyl or isopropyl;

R$^4$, R$^5$, R$^6$ and R$^{10}$ each independently represent hydrogen or $C_{1-4}$alkyl;

Het$^1$ and Het$^2$ each independently represent pyrrolidinyl, piperidinyl or piperazinyl wherein said Het$^1$ or Het$^2$ is optionally substituted with hydroxy; in particular Het$^1$ represents pyrrolidinyl or piperazinyl and Het$^2$ represents piperidinyl, piperazinyl or pyrrolidinyl wherein said pyrrolidinyl is optionally substituted with hydroxy;

Het$^4$ represents piperazinyl optionally substituted with $C_{1-4}$alkyl;

Het$^{10}$, Het$^{11}$, Het$^{12}$ and Het$^{13}$ each independently represent pyrrolidinyl, piperidinyl or piperazinyl wherein said Het$^{10}$, Het$^{11}$, Het$^{12}$ and Het$^{13}$ are optionally substituted with hydroxy; in particular Het$^{10}$, Het$^{11}$, Het$^{12}$ and Het$^{13}$ represent piperazinyl; and Het$^{14}$ represents morpholinyl; pyrrolidinyl; pyrrolyl; 1,2,3-triazolyl; 2,3,4-triazapyrrolyl; piperidinyl or piperazinyl wherein said Het$^{14}$ is optionally substituted with $C_{1-4}$alkyl.

3. A compound according to claim 1 wherein;
m represents 1; n represents 1; Z represents N or C;
Y represents —NR$^2$—$C_{1-6}$alkyl-CO—NR$^4$—, -Het$^{11}$-CO—$C_{1-6}$alkyl-, —CO-Het$^{13}$-$C_{1-6}$alkyl-, —CO—NR$^{10}$—$C_{1-6}$alkyl-, -Het$^1$-$C_{1-6}$alkyl-CO—NR$^5$—, or -Het$^2$-CO—NR$^6$— wherein the —$C_{1-6}$alkyl-linker in —NR$^2$—$C_{1-6}$alkyl-CO—NR$^4$— or -Het$^1$-$C_{1-6}$alkyl-CO—NR$^5$— is optionally substituted with hydroxy;
X$^1$ represents —$C_{1-4}$alkyl-, $C_{1-4}$alkyloxy- or $C_{1-4}$alkyl-NR$^3$;
X$^2$ represents a direct bond, $C_{1-4}$alkyl, $C_{1-4}$alkyloxy or $C_{1-4}$alkyl-NR$^7$-;
R$^1$ represents hydrogen or halo;
R$^8$ represents hydrogen or halo;
R$^2$ represents hydrogen, $C_{1-4}$alkyl, or Het$^4$-$C_{1-4}$alkyl-;
R$^3$ and R$^7$ each independently represent hydrogen or $C_{1-4}$alkyl;
R$^4$, R$^5$, R$^6$ and R$^{10}$ each independently represent hydrogen or $C_{1-4}$alkyl;
Het$^1$ and Het$^2$ each independently represent pyrrolidinyl, piperidinyl or piperazinyl wherein said Het$^1$or Het$^2$ is optionally substituted with hydroxy;
Het$^4$ represents piperazinyl optionally substituted with $C_{1-4}$alkyl;
Het$^{11}$ represents piperidinyl or piperazinyl; and
Het$^{13}$ represents piperidnyl or piperazinyl.

4. A compound according to claim 1 wherein;
m represents 1; n represents 1; Z represents N or C;
Y represents —$C_{1-4}$alkyl-NR$^9$—$C_{1-4}$alkyl-, —NR$^2$—$C_{1-6}$alkyl-CO—NR$^4$—, —Het$^1$-$C_{1-6}$alkyl-CO—NR$^5$— or Het$^2$-CO—NR$^6$— wherein the $C_{1-6}$alkyl linker in —Y— is optionally substituted with one or where possible two or more substituents selected from hydroxy, halo or phenyl;
X$^1$ represents $C_{1-4}$alkyl, $C_{1-4}$alkyloxy, ethyl or ethoxy;
X$^2$ represents $C_{1-4}$alkyl, $C_{1-4}$alkyloxy, —NR$^7$—$C_{1-4}$alkyl, propyl, —NR$^7$-ethyl- or NR$^7$-propyl-;
R$^1$ represents hydrogen, chloro, fluoro or bromo;
R$^2$ represents hydrogen, $C_{1-4}$alkyl or $C_{2-4}$alkenyl;
R$^4$ represents hydrogen; R$^5$ represents hydrogen or $C_{1-4}$alkyl;
R$^6$ represents hydrogen or $C_{1-4}$alkyl; R$^7$ represents hydrogen or $C_{1-4}$alkyl;
R$^8$ represents hydrogen, chloro, fluoro or bromo;
R$^9$ represents hydrogen or $C_{1-4}$alkyl;
Het$^1$ represents piperazinyl or piperidinyl; and
Het$^2$ represents pyrrolidinyl, piperidinyl or piperazinyl wherein said Het$^2$ is optionally substituted with hydroxy.

5. A compound according to claim 1 wherein said compound is selected from the group consisting of;
14-methyl-3,5,7,14,17,22,27-heptaazatetracyclo[19.3.1.1~2,6~0.1~8,12~]heptacosa-1(25),2(27),3,5,8(26),9,11,21,23-nonaen-19-yn-16-one;
(19Z)-19-chloro-14-methyl-3 ,5,7,14,17,22,27-heptaazatetracyclo[19.3.1.1~2,6~0.1~8,12~]heptacosa-1(25),2(27),3 ,5 ,8(26),9,11,19,21,23-decaen-16-one;
14-methyl-3,5,7,14,17,22,27-heptaazatetracyclo[19.3.1.1~2,6~0.1~8,12]heptacosa-1(25),2(27),3,5,8(26),9,11,21,23-nonaen-16-one;

1,8,10,12,17,22,26,32-octaazapentacyclo[24.2.2.1~3,7~0.1~9,13~0.1~14,18~]tritriaconta-3(33),4,6,9(32),10,12,14(31),15,17-nonaen-23-one;

1,8,10,12,17,22,25,31-octaazapentacyclo[23.2.2.1~3,7~0.1~9,13~0.1~14,18~]dotriaconta-3(32),4,6,9(31),10,12,14(30),15,17-nonaen-23-one;

17-methyl-3,5,7,14,17,22,27-heptaazatetracyclo[19.3.1.1~2,6~0.1~8,12~]heptacosa-1(25),2(27),3,5,8(26),9,11,21,23-nonaen-15-one;

18-methyl-3,5,7,15,18,23,28-heptaazatetracyclo[20.3.1.1~2,6~0.1~8,12~]octacosa-1(26),2(28),3,5,8(27),9,11,22,24-nonaen-16-one;

14-methyl-3,5,7,14,17,20,22,27-octaazatetracyclo[19.3.1.1~2,6~0.1~8,12~]heptacosa-1(25),2(27),3,5,8(26),9,11,21,23-nonaen-16-one;

14-methyl-3,5,7,14,17,21,23,28-octaazatetracyclo[20.3.1.1~2,6~0.1~8,12~]octacosa-1(26),2(28),3,5,8(27),9,11,22,24-nonaen-16-one;

18-ethyl-3,5,7,15,18,23,28-heptaazatetracyclo[20.3.1.1~2,6~0.1~8,12~]octacosa-1(26),2(28),3,5,8(27),9,11,22,24-nonaen-16-one;

5-chloro-1,8,10,12,17,22,30-heptaazapentacyclo[22.2.2.1~3,7~0.1~9,13~0.1~14,18~]hentriaconta-3(31),4,6,9(30),10,12,14(29),15,17-nonaen-23-one;

5-chloro-1,8,10,12,17,22,25,31-octaazapentacyclo[23.2.2.1~3,7~0.1~9,13~0.1-14,18~]dotriaconta-3(32),4,6,9(31),10,12,14(30),15,17-nonaen-23-one;

10-chloro-14-methyl-3,5,7,14,17,22,27-heptaazatetracyclo[19.3.1.1~2,6~0.1~8,12~]heptacosa-1(25),2(27),3,5,8(26),9,11,21,23-nonaen-16-one; and 10-chloro-14-ethyl-3,5,7,14,17,22,27-heptaazatetracyclo[19.3.1.1~2,6~0.1~8,12~]heptacosa-1(25),2(27),3,5,8(26),9,11,21,23-nonaen-16-one;

including the N-oxide forms, the pharmaceutically acceptable addition salts and the stereochemically active forms thereof.

6. A compound according to claim 1 where said compound is selected from the trifluoroacetic acid salts of;

18-ethyl-3,5,7,15,18,23,28-heptaazatetracyclo[20.3.1.1~2,6~0.1~8,12~]octacosa-1(26),2(28),3,5,8(27),9,11,22,24-nonaen-16-one;

14-methyl-3,5,7,14,17,21,23,28-octaazatetracyclo[20.3.1.1~2,6~0.1~8,12~]octacosa-1(26),2(28),3,5,8(27),9,11,22,24-nonaen-16-one;

1,8,10,12,17,22,25,31-octaazapentacyclo[23.2.2.1~3,7~0.1~9,13~0.1~14,18~]dotriaconta-3(32),4,6,9(31),10,12,14(30),15,17-nonaen-23-one;

14-methyl-3,5,7,14,17,20,22,27-octaazatetracyclo[19.3.1.1~2,6~0.1~8,12~]heptacosa-1(25),2(27),3,5,8(26),9,11,21,23-nonaen-16-one;

14-methyl-3,5,7,14,17,22,27-heptaazatetracyclo[19.3.1.1~2,6~0.1~8,12~]heptacosa-1(25),2(27),3,5,8(26),9,11,21,23-nonaen-16-one; or 1,8,10,12,17,22,26,32-octaazapentacyclo[24.2.2.1~3,7~0.1~9,13~0.1~14,18~]tritriaconta-3(33),4,6,9(32),10,12,14(31),15,17-nonaen-23-one.

7. A pharmaceutical composition comprising a compound according claim 1.

8. An intermediate of formula (XI)

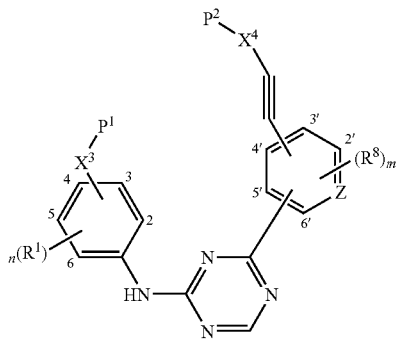

(XI)

the pharmaceutically acceptable addition salts and the stereochemically isomeric forms thereof, wherein n represents an integer from 1 to 4; m represents an integer from 1 to 4;

Z represents N or C;

$P_1$ and $P_2$ each independently represent hydroxy, halo, hydroxycarbonyl-, halocarbonyl-, $C_{1-6}$alkyloxycarbonyl- or $C_{1-6}$alkyloxycarbonyl-$C_{1-4}$alkyl-;

$X^3$ represents $C_{1-6}$alkyl or $C_{1-6}$alkyl-NR$^{20}$;

$X^4$ represents $C_{1-6}$alkyl or $C_{1-6}$alkyl-NR$^{21}$;

$R^1$ and $R^8$ each independently represent hydrogen, cyano, halo, hydroxy, $C_{1-6}$alkoxy-, $C_{1-6}$alkyl-, mono- or di($C_{1-4}$alkyl)amino-carbonyl-, mono- or di($C_{1-4}$alkyl)aminosulfonyl, $C_{1-6}$alkoxy- substituted with halo or $R^1$ represents $C_{1-6}$alkyl substituted with one or where possible two or more substituents selected from hydroxy or halo;

$R^{20}$ and $R^{21}$ each independently represents hydrogen, $C_{1-4}$alkyl, Het$^{20}$, Het$^{21}$-$C_{1-4}$alkyl-, $C_{2-4}$alkenylcarbonyl- optionally substituted with Het$^{22}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

Het$^{20}$ represents a heterocycle selected from morpholinyl, pyrrolidinyl, piperazinyl, or piperidinyl wherein said Het$^{20}$ is optionally substituted with $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-;

Het$^{21}$ represents a heterocycle selected from morpholinyl, pyrrolidinyl, piperazinyl, or piperidinyl wherein said Het$^{21}$ is optionally substituted with $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-;

Het$^{22}$ represent a heterocycle selected from morpholinyl, pyrrolidinyl, piperazinyl, or piperidinyl wherein said Het$^{22}$ is optionally substituted with $C_{1-4}$alkyl, $C_{3-6}$cycloalkyl, hydroxy-$C_{1-4}$allyl-, $C_{1-4}$alkyloxy$C_{1-4}$alkyl or polyhydroxy-$C_{1-4}$alkyl-.

9. An intermediate according to claim 8 wherein, n represents 1; m represents 1; Z represents N or C, in particular N;

$P_1$ and $P_2$ each independently represent hydroxy, $C_{1-6}$alkyloxycarbonyl or $C_{1-6}$alkyloxycarbonyl-$C_{1-4}$alkyl-;

$X^3$ represents —$C_{1-4}$alkyl- or $C_{1-4}$alkyl-NR$^{20}$—;

$X^4$ represents —$C_{1-4}$alkyl- or $C_{1-4}$alkyl-NR$^{21}$—;

$R^1$ represents hydrogen or halo;

$R^8$ represents hydrogen;

$R^{20}$ and $R^{21}$ each independently represents hydrogen or $C_{1-4}$alkyl.

10. A pharmaceutical composition comprising an intermediate according to claim 8.

* * * * *